(12) United States Patent
Goff et al.

(10) Patent No.: US 8,927,564 B2
(45) Date of Patent: Jan. 6, 2015

(54) SYNTHESIS OF POLYCYCLIC ALKALOIDS

(71) Applicant: Rigel Pharmaceuticals, Inc., South San Francisco, CA (US)

(72) Inventors: Dane Goff, Redwood City, CA (US); Donald G. Payan, Hillsborough, CA (US); Sylvia Braselmann, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/789,289

(22) Filed: Mar. 7, 2013

(65) Prior Publication Data
US 2013/0237524 A1    Sep. 12, 2013

Related U.S. Application Data

(60) Provisional application No. 61/607,808, filed on Mar. 7, 2012.

(51) Int. Cl.
| | |
|---|---|
| *C07D 487/14* | (2006.01) |
| *C07D 471/04* | (2006.01) |
| *C07D 471/14* | (2006.01) |
| *C07D 471/22* | (2006.01) |
| *C07D 487/04* | (2006.01) |
| *C07D 491/22* | (2006.01) |
| *A61K 31/437* | (2006.01) |
| *C07D 513/04* | (2006.01) |
| *C07D 491/147* | (2006.01) |
| *C07D 495/14* | (2006.01) |
| *C07D 495/22* | (2006.01) |
| *C07D 498/04* | (2006.01) |
| *C07D 513/14* | (2006.01) |

(52) U.S. Cl.
CPC ............ *C07D 471/04* (2013.01); *C07D 487/04* (2013.01); *C07D 471/14* (2013.01); *C07D 487/14* (2013.01); *C07D 513/04* (2013.01); *C07D 471/22* (2013.01); *C07D 491/147* (2013.01); *C07D 491/22* (2013.01); *C07D 495/14* (2013.01); *C07D 495/22* (2013.01); *C07D 498/04* (2013.01); *C07D 513/14* (2013.01)
USPC ............................................. 514/283; 546/51

(58) Field of Classification Search
USPC ............................................ 546/51; 514/283
See application file for complete search history.

(56) References Cited

U.S. PATENT DOCUMENTS

2009/0054304 A1    2/2009    Herbert et al.

FOREIGN PATENT DOCUMENTS

| EP | 2 322 222 | 5/2011 |
|---|---|---|
| WO | WO 2008/067222 | 6/2008 |
| WO | WO 2008/091540 | 7/2008 |

OTHER PUBLICATIONS

Jida et al. (Green Chemistry (2012), 14(4), 909-911).*
Jida et al. (Green Chemistry (2010), 12(6), 961-964).*
Bentley, "β-Phenylethylamines and the isoquinoline alkaloids," *Nat. Prod. Rep.* 21:395-424, 2004.
Fiorucci et al., "Bile-acid-activated rectors: targeting TGR5 and farnesoid-X-receptor in lipid and glucose disorders," *Trends in Pharmacological Sciences* 30(11):570-580, 2009.
Goff, "Diverse Alkaloid-Like Structures from a Common Building Block," *Tetrahedron* 69(1):242-256, 2013.
Kumar et al., "Synthesis of Natural Product Inspired Compound Collections," *Angew. Chem. Int. Ed.* 48:3224-3242, 2009.
Reimann et al., "A Novel Stereoselective Synthesis of *cis*-Configured Erythrinane and Erythrinane Type Analogues," *Monatshefte für Chemie* 135:959-975, 2004.
Yokoi et al., "ESR Studies on Salicylaldehyde Schiff Base Complexes of Copper(II). III. Dimer Formation on Bis(N-alkylsalicylideneaminato) copper(II) Complexes and Their Derivatives in Toluene," *Bull. Chem. Soc. Jpn.* 63(5):1462-1466, 1990.
Camarero et al., "Stereocontrolled conjugate additions to dihydroindolizinone systems. Synthesis of enantiopure polysubstituted tetrahydropyrrolo[2,1-α]isoquinolones," *Tetrahedron* 65:5787-5798, 2009.
Cassidy et al., "An Aza-Wittig/π-Furan Cyclization Approach Toward the Homoerythrina Alkaloid (±)-Selaginoidine," *Organic Letters* 7(7):1339-1342, 2005.
Collado et al., "Metalation vs Nucleophilic Addition in the Reactions of N-Phenethylimides with Organolithium Reagents. Ready Access to Isoquinoline Derivatives via N-Acyliminium Ions and Parham-Type Cyclizations," *J. Org. Chem.* 62(7):2080-2092, 1997.
Goff, "Diverse alkaloid-like structures from a common building block," *Tetrahedron* 69:42-256, 2013.
Holloway et al., "Direct Enantioselective Brønsted Acid Catalyzed N-Acyliminium Cyclization Cascades of Tryptamines and Ketoacids," *Organic Letters* 12(21):4720-4723, 2010.
Johns et al., "New Histamine Alkaloids from a *Glochidion* Species," *Chemical Communications* pp. 10"312-313, 1966.
Mondon, "Synthetische Arbeiten in der Reihe der aromatischen Erythrina-Alkaloide VIII. Zur Existenz von *trans*-Erythrinanen," *Chem. Ber.* 104:270-278, 1971.

(Continued)

*Primary Examiner* — Bruck Kifle

(74) *Attorney, Agent, or Firm* — Travis Young; Klarquist Sparkman, LLP

(57) ABSTRACT

Disclosed embodiments concern polycyclic alkaloid compounds and methods for their use and synthesis. Particular embodiments concern polycyclic alkaloids having a fused, six-membered ring, while other embodiments concern polycyclic alkaloids having a fused, five-membered ring. Methods for making the polycyclic alkaloids are disclosed, as well as methods for their use as prophylactics or treatments for certain diseases. Also disclosed are pharmaceutical compositions comprising the polycyclic alkaloids and their use.

17 Claims, 1 Drawing Sheet

(56) References Cited

OTHER PUBLICATIONS

Muratore et al., "Enantioselective Brønsted Acid-Catalyzed N-Acyliminium Cyclization Cascades," *J. Am. Chem. Soc.* 131(31):10796-10797, 2009.

Rose et al., "Acid-Promoted Cyclization Reactions of Tetrahydroindolinones. Model Studies for Possible Application in a Synthesis of Selaginoidine," *J. Org. Chem.* 72(2):538-549, 2007.
International Search Report dated Apr. 26, 2013, from International Application No. PCT/US2013/029656.

* cited by examiner

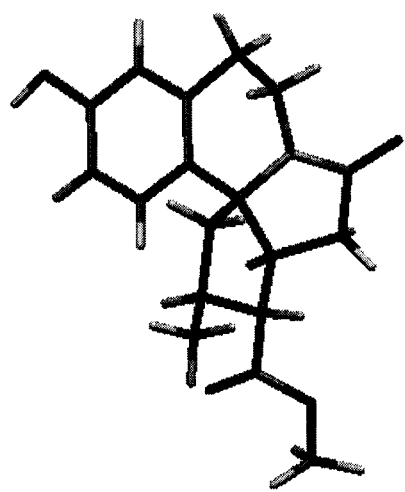

SYNTHESIS OF POLYCYCLIC ALKALOIDS

CROSS REFERENCE TO RELATED APPLICATION

This application claims the benefit of the earlier filing date of U.S. Provisional Application No. 61/607,808, filed Mar. 7, 2012. The entire disclosure of this prior application is incorporated herein by reference.

FIELD

The present disclosure concerns polycyclic alkaloid compounds and embodiments of a method for making and using such compounds.

BACKGROUND

Biological activity is typically conferred by a set of structural features in a molecule that is recognized at a biological target, e.g., a receptor site. These features include structural steric and electronic features, and the set of such features is termed a "pharmacophore." Certain natural products possess potent and selective biological activity, and a mutual interplay exists between natural products and the medicinal and biological sciences, as well as organic chemistry. Isolated natural products have provided a vast source of disease modulating drugs and efficient tools for studying biological phenomenon.

In order to fully explore the effects of various natural products on the increasing number of biological targets, it is necessary to develop synthetic methodologies that provide natural product analogs efficiently and in quantifiable yields.

Recently, there has been a keen interest in developing syntheses of *Erythrina* alkaloids and their analogs. The homologous [6.6.5.6]-erythrinan ring system (illustrated below) exhibits diverse biological activity (Reimann, E. *Prog. Org. Nat. Prod.* 2007, 88, 1; Bentley, K. W. *Nat. Prod. Rep.* 2004, 21, 395).

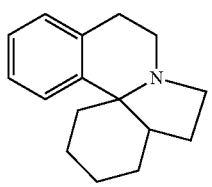

[6.6.5.6]-erythrinan ring system

Bile acids are amphipathic molecules that solubilize dietary lipids and promote the absorption of the lipids into the digestive tract. Bile acids may also act as signaling molecules, which activate signaling networks within the body, such as TGR5 (a G-protein-coupled receptor), and members of the nuclear hormone receptor superfamily (e.g. farnesoid-X-receptor, constitutive androstane receptor, pregnane X receptor, and vitamin D receptor). TGR5 belongs to the rhodopsin-like superfamily of GPCRs that transduces signals through the $G_s$ protein. TGR5 is expressed in gall bladder tissue, ileum tissue, and colon tissue and it has been found to regulate energy expenditure by increasing basal metabolism. In particular, TGR5 ligation may stimulate cAMP synthesis and/or activate the mitogen-activated protein kinase pathway. TGR5 activation causes internalization of the receptor and increased intracellular cAMP, which can then activate protein kinase A. TGR5 may also be involved in regulating glucose homeostasis and regulating intrahepatic microcirculation. Given TGR5's important biological activity, it has emerged as an important target for treating disorders of lipid and glucose homeostasis.

Efforts to develop TGR5 agonists have so far been focused on exploiting the structure of natural ligands, such as LCA, TLCA, and oleanolic acid. In addition, the 23-alkyl-substituted and 6,23-alkyl disubstituted derivatives of CDCA have been shown to be agonists of TGR5. While these compounds can act as TGR5 agonists, these steroidal TGR5 ligands can be toxic and levels of their administration must be carefully monitored to prevent deleterious effects. There also exist semi-synthetic non-steroidal TGR5 agonists, such as 6-methyl-2-oxo-4-thiophen-2-yl-1,2,3,4-tetrahydropyrimidine-5-carboxylic acid benzyl esters, quinazolinones, imidazole[1,2-a][1,2]diazepin, and qinolines. Despite these known agonists, there exists a need in the art for TGR5 agonists that are safe for administration and that effectively target either TGR5 receptors, bile acid receptors, and/or G-protein-coupled receptors.

SUMMARY

Disclosed embodiments concern compounds having a formula

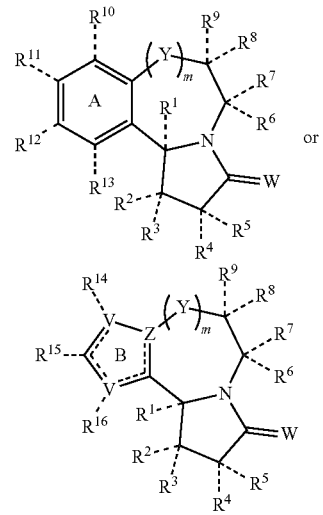

$R^1$ is selected from hydrogen, aliphatic, aryl, a heteroatom-containing moiety, or is bound to either $R^2$ or $R^3$ to form a four-, five-, or seven-membered cyclic aliphatic or a heterocycle;

$R^2$ and $R^3$ independently are selected from hydrogen, aliphatic, aryl, aliphatic and bound to $R^1$, heteroaliphatic and bound to $R^1$, or, where $R^1$ is hydrogen, $R^2$ and $R^3$ are aliphatic and bound together to form a five-, six-, or seven-membered cyclic aliphatic or a heterocycle;

$R^4$, $R^5$, $R^6$, $R^7$, $R^8$, and $R^9$ independently are selected from aliphatic, aryl, halogen, a heteratom-containing moiety, hydrogen, or any combination thereof;

$R^{10}$, $R^{11}$, $R^{12}$, and $R^{13}$ independently are selected from aliphatic, aryl, halogen, a heteroatom-containing moiety, hydrogen, and any combination thereof;

$R^{14}$, $R^{15}$, and $R^{16}$ independently are selected from aliphatic, aryl, halogen, a heteroatom-containing moiety, heteroaliphatic, heteroaryl, and hydrogen; or $R^{14}$ and $R^{15}$ or $R^{15}$ and $R^{16}$ are selected to form, together with the atom to which each is attached, a four-, five-, six-, or seven-membered cyclic alkane or alkene, or a five-, six-, or seven-membered aromatic ring;

W is selected from oxygen, sulfur, and $NR^{17}$ wherein $R^{17}$ is selected from aliphatic, aryl, heteroaliphatic, heteroaryl, and hydrogen;

Y is selected from $-(CH_2)-$, $-(CHR^{17})-$, and $-(CR^{17}R^{18})-$, oxygen, sulfur, any oxidized form of sulfur, and $NR^{17}$ wherein $R^{17}$ is selected from aliphatic, aryl, heteroaliphatic, heteroaryl, and hydrogen;

each V independently is selected from an sp3 or sp2 carbon atom, oxygen, sulfur, nitrogen, and $NR^{17}$ wherein $R^{17}$ is selected from aliphatic, aryl, heteroaliphatic, heteroaryl, and hydrogen, and any combination thereof;

Z is selected from an sp3 or sp2 carbon atom, $(CR^{17})$, or nitrogen; and m is zero or one.

In one embodiment, the oxidized form of sulfur is a sulfonyl or a sulfinyl group.

In one embodiment, $R^1$ is an aliphatic chain bound to either $R^2$ or $R^3$ or a heteroaliphatic chain bound to either $R^2$ or $R^3$.

In one embodiment, $R^4$, $R^5$, $R^6$, $R^7$, $R^8$, and $R^9$ independently are selected from alkane, alkene, alkyne, fluorine, chlorine, bromine, iodine, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are selected from hydrogen, aliphatic, aryl, heteroaliphatic, heteroaryl, and any combination thereof.

In one embodiment, $R^6$ or $R^7$ and at least one of $R^8$ or $R^9$ can be selected to form, together with the atom to which each is attached, a cyclic alkane or alkene, with remaining $R^6$, $R^7$, $R^8$, or $R^9$ substituents being hydrogen.

In one embodiment, $R^7$ and $R^9$ are not present, the carbon atoms bearing $R^6$ and $R^8$ are bound via a double bond, and $R^6$ and $R^8$ are selected to form, together with the atom to which each is attached, a five-, six-, or seven-membered aromatic or heteroaromatic ring. In another embodiment, $R^6$ and $R^8$ are not present, the carbon atoms bearing $R^7$ and $R^9$ are bonded via a double bond, and $R^7$ and $R^9$ are selected to form, together with the atom to which each is attached, a five-, six-, or seven-membered aromatic or heteroaromatic ring.

In one embodiment, $R^{10}$, $R^{11}$, $R^{12}$, and $R^{13}$ independently are selected from alkane, alkene, alkyne, fluorine, chlorine, bromine, iodine, aldehyde, carboxyl, ether, ester, hydroxyl, silyl, silyl ether, phosphate, phosphoryl, phosphodiester, phosphine, thiol, thioether, thioester, sulfonyl, disulfide, sulfoxide, sulfonic, thiocyanate, isothiocyanate, oxazole, oxadiazole, imidazole, triazole, tetrazole, amide, azide, azo, cyanate, isocyanate, nitrile, isonitrile, nitro, nitroso, and $NR^{17}R^{18}$ wherein $R^{17}$ and $R^{18}$ independently are selected from hydrogen, aliphatic, aryl, heteroaliphatic, heteroaryl, and any combination thereof.

In one embodiment, $R^{14}$, $R^{15}$, and $R^{16}$ independently can be selected from alkane, alkene, alkyne, fluorine, chlorine, bromine, iodine, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are selected from hydrogen, aliphatic, aryl, heteroaliphatic, heteroaryl, and any combination thereof.

Particular embodiments concern compounds having the following formulas

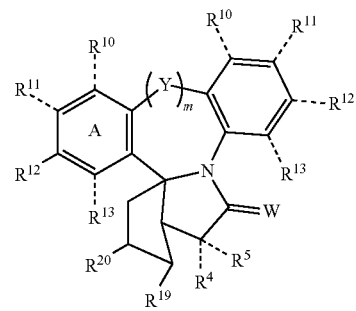

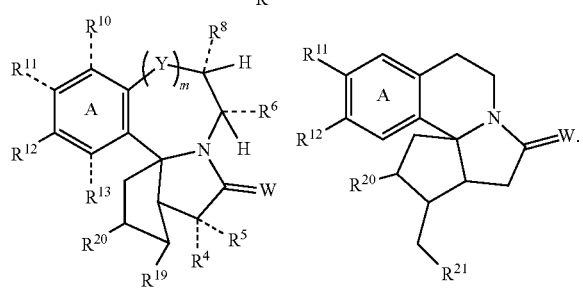

Other embodiments concern compounds having the following formulas

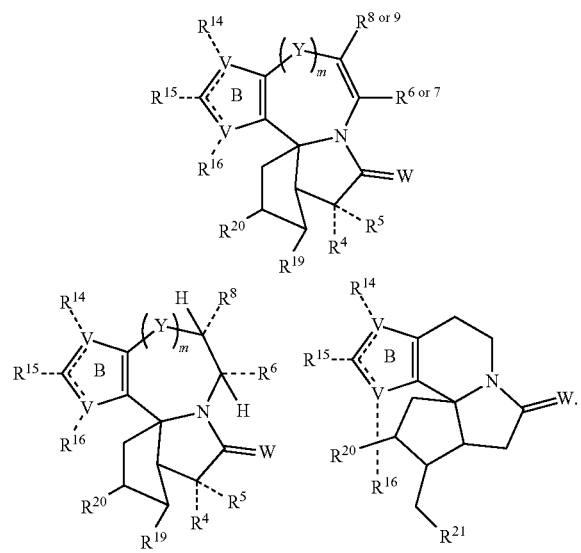

In one embodiment, the V bearing $R^{14}$ is carbon; $R^{14}$ and $R^{15}$ are joined, together with the atom to which they are bound, to form an aromatic ring; and any remaining V is selected from oxygen, sulfur, and nitrogen. In another embodiment, the V bearing $R^{16}$ is carbon, $R^{15}$ and $R^{16}$ are joined, together with the atom to which they are bound, to form an aromatic ring; and any remaining V is selected from oxygen, sulfur, and nitrogen.

In one embodiment, $R^{19}$ is selected from nitromethyl, —$CH_2$—$NH_2$, carboxyl, and amide, and $R^{20}$ is selected from methyl and hydrogen.

In one embodiment, W is oxygen.

In one embodiment, $R^{16}$ is sulfonyl.

In one embodiment, $R^{20}$ is selected from lower alkyl and substituted lower alkyl, wherein substituted lower alkyl is selected from a lower alkyl group substituted with one or more halogen atoms.

In one embodiment, $R^{21}$ is nitro.

Particular embodiments of the disclosed compounds have the stereochemistry illustrated below.

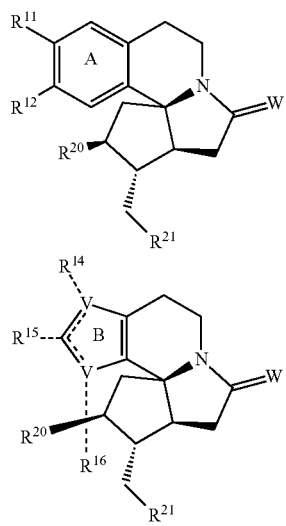

An exemplary compound has the following structure

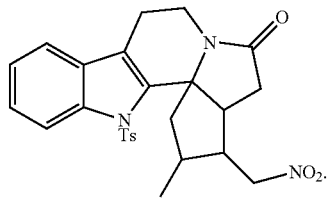 [SMILES: Cc1ccc(S(=O)(=O)n2c3c(c4ccccc42)CCN2C(=O)CC4C(C[N+](=O)[O-])C(C)CC342)cc1]

With reference to this compound, the stereochemistry may be

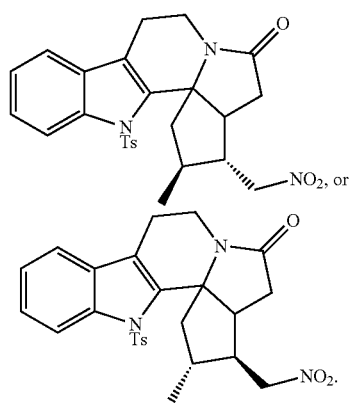

Also disclosed is a method for making the disclosed compounds. The method comprises providing an aromatic amine compound having a formula

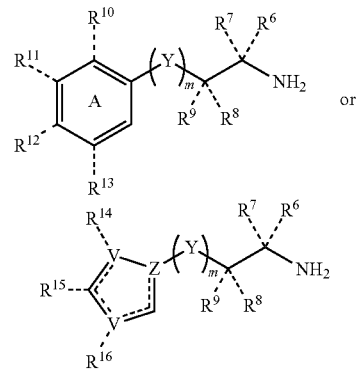

and a carboxylic acid intermediate having a formula

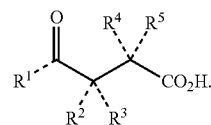

The aromatic amine and carboxylic acid compound are exposed to reaction conditions sufficient to form a hemiaminal intermediate having a formula

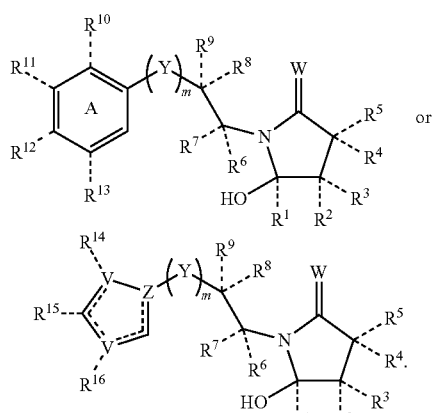

Subsequently, the hemiaminal intermediate is exposed to an acid to form a polycyclic alkaloid having a formula

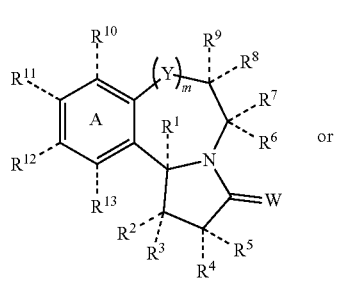

-continued

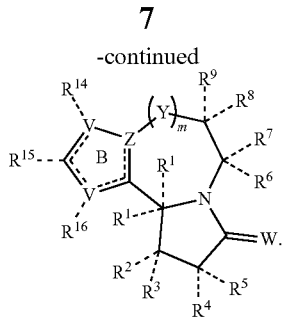

Also disclosed are pharmaceutical compositions comprising a polycyclic alkaloid and a pharmaceutically acceptable carrier, diluent or excipient, the polycyclic alkaloid being a compound having a formula

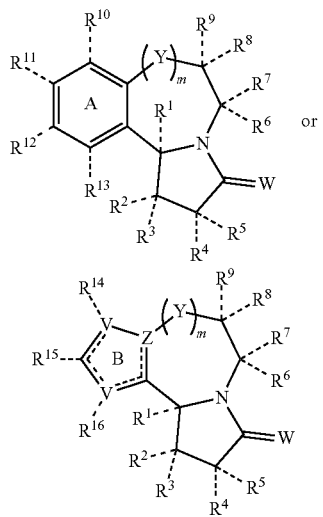

and salts, hydrates, solvates, and prodrugs thereof. The pharmaceutical composition can act as a prophylactic or therapeutic agent in treating hypotension or central nervous system disorders. The pharmaceutical composition may also be used to treat a disease and/or disorder associated with TGR5 receptors, bile acid receptors, and/or G-protein coupled receptors. In particular embodiments, the compound of the pharmaceutical composition is in the form of a pharmaceutically acceptable salt, such as a hydrochloride salt, a hydrogen sulfate salt, a sulfate salt, a phosphate salt, an alkane sulfonate salt, a methane sulfonate salt, an ethane sulfonate salt, or a p-toluene sulfonate salt.

Disclosed embodiments can be used in a method of treating and/or preventing hypotension, a central nervous system disorder, and diseases associated with irregular protein kinase activity, comprising contacting a subject with an amount of the disclosed compounds effective to treat and/or prevent hypotension, the central nervous system disorder, and the disease associated with irregular protein kinase activity. In certain embodiments, the amount of compound ranges from about 0.0001 or 0.001 or 0.01 mg/kg/day to about 100 mg/kg/day. The method can be used for animals and humans. In other embodiments, a pharmaceutical composition comprising the disclosed compounds is used in the method of treating and/or preventing hypotension, a central nervous system disorder, and diseases associated with irregular protein kinase activity. Particular embodiments concern using an amount of the pharmaceutical composition ranging from 0.0001 or 0.001 or 0.01 mg/kg/day to about 100 mg/kg/day. In particular disclosed embodiments, the amount of the polycyclic alkaloid can range from greater than zero to about 99% of the pharmaceutical composition, more typically from about 1% to about 90%, even more typically from about 10% to about 90%.

In particular disclosed embodiments, the disease/disorder associated with TGR5 receptors, bile acid receptors or G-protein coupled receptors is selected from cholelithiasis, cerebrotendinous xanthomatosis, primary biliary cirrhosis, non-alcoholic fatty liver disease, hypertriglyceridaemia, hypercholesterolaemia, skin cancer, lung cancer, colon cancer, metabolic diseases, 3b-hydroxysteroid oxido-reductase deficiency, and combinations thereof.

Also disclosed herein is a method for treating a disease or disorder associated with intestinal motility, comprising administering an effective amount of a compound having any one of the formulas provided herein. The disease or disorder associated with intestinal motility may be selected from diverticulosis, megacolon, intestinal pseudoobstruction, constipation, dyspepsia, gastroparesis, irritable bowel syndrome, and combinations thereof. In particular disclosed embodiments, disease or disorder associated with intestinal motility is selected from small-intestinal diverticula, colonic diverticula, diverticulitis, painful diverticular disease without diverticulitis, hemorrhage from diverticula, aganglionic megacolon, chronic idiopathic megacolon, acquired megacolon, chronic or intermittent secondary pseudoobstruction, idiopathic intestinal pseudoobstruction, acute intestinal pseudoobstruction, and combinations thereof.

Particular embodiments of the disclosed compound may be used as TGR5 receptor agonists, bile acid receptor modulators, and/or G-protein coupled receptor ligands.

The foregoing and other objects, features, and advantages of the invention will become more apparent from the following detailed description, which proceeds with reference to the accompanying figures.

BRIEF DESCRIPTION OF THE DRAWINGS

FIG. 1 is an x-ray structure of a particular embodiment of the disclosed polycyclic alkaloid.

DETAILED DESCRIPTION

I. Introduction

Of particular interest in the scientific community are non-planar ring systems that can be constructed on scale and display varied substituents in three-dimensional space. Particular embodiments of disclosed compounds define a new series of complex polycyclic alkaloid-like molecules with different ring sizes and topologies made by the disclosed method. In certain embodiments, compounds made by the disclosed method undergo functional group manipulation to make various additional, useful analogs.

II. Terms and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise. A wavy line ("〜"), is used to indicate a bond disconnection, and a dashed line ("- - -") is used to illustrate that a bond may optionally be present at a particular position.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Acyliminium Cyclization: A reaction in which an iminium ion is acylated to form an intermediate acyliminium ion, which is an electrophile that will cyclize with aromatic ring systems under mild conditions. An example of an acyliminium cyclization is illustrated below, and is intended only as an illustration of the reaction, not a limitation:

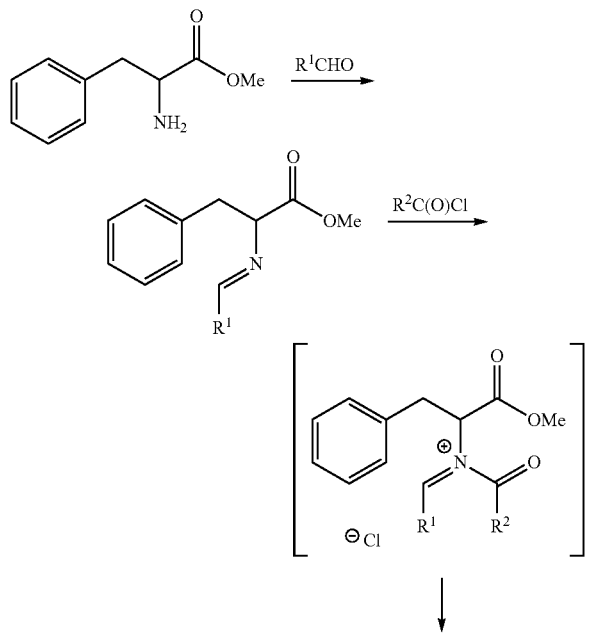

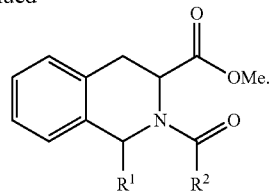

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. This term also encompasses substituted aliphatic compounds.

Alkaloid: A group of chemical compounds, which mostly contain basic nitrogen atoms, but can also include related compounds having neutral or weakly acidic properties.

Alkenyl: Hydrocarbon groups having carbon chains containing one or more double bonds.

Alkyl: A hydrocarbon group having a saturated carbon chain. The chain may be cyclic, branched or unbranched. The term lower alkyl means the chain includes 1-10 carbon atoms.

Alkynyl: Hydrocarbon groups having carbon chains containing one or more triple bonds.

Analog: A molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure-activity relationships (QSAR), with techniques such as those disclosed in Remington (*The Science and Practice of Pharmacology*, 21$^{st}$ Edition (2005), chapter 28).

Aromatic: "Aromatic" compounds typically are unsaturated, cyclic hydrocarbons having alternate single and double bonds. Aromatic encompasses compounds comprising only carbon and hydrogen atoms, and compounds comprising one or more heteroatoms, such as, but not limited to nitrogen, oxygen, sulfur, and any combination thereof. This term also encompasses substituted aromatic.

Aryl: A substantially hydrocarbon-based aromatic compound, or a radical thereof (e.g. $C_6H_5$) as a substituent bonded to another group or groups, particularly other organic groups, and having a ring structure as exemplified by, but not limited to benzene, naphthalene, phenanthrene, anthracene, etc. This term also encompasses substituted aryl compounds.

Arylalkyl: An acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl may be used.

Boc (t-Boc): A tert-butyloxycarbonyl group that functions as a protecting group in synthesis, particularly peptide synthesis. Boc groups can be removed by strong acids, e.g., HCl.

COSY: Correlation Spectroscopy

Cyclic: Designates a substantially hydrocarbon, closed-ring compound, or a radical thereof. Cyclic compounds or substituents also can include one or more sites of unsaturation, but does not include aromatic compounds. One example of a cyclic compound is cyclopentane.

Cycloaddition Reaction: Cycloadditions are characterized by two components' coming together to form two new sigma-bonds, at the ends of both components, joining them together to form a ring, with a reduction in the length of the conjugated system of the conjugated system of orbitals in each component.

DCM: Dichloromethane.

Diastereomers: Optically active isomers containing two or more asymmetric carbons with differing configurations at one or more of the stereocenters and are not mirror images of each other, as exemplified below:

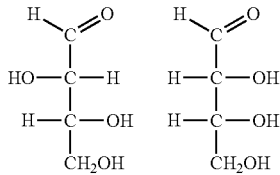

Diastereomers that differ at only one stereocenter are also known as epimers. As indicated herein, the compounds may exist as a single isolated diastereomer, or may exist as a mixture of diastereomers. Accordingly, if a particular stereochemistry is indicated, the particular compound is not limited to that particular stereoisomer.

DMF: Dimethylformamide.

EDC: N-ethyl-N'-(3-dimethylaminopropyl)carbodiimide.

Enantiomers: Optically active isomers containing one or more asymmetric carbons that are non-superimposable mirror images of one another, as exemplified below:

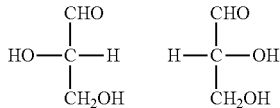

E/Z isomers: Isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond. The E and Z isomers of 2-butene are shown below:

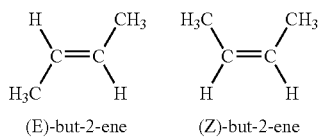

Functional group: A specific group of atoms within a molecule that is responsible for the characteristic chemical reactions of the molecule. Exemplary functional groups include, without limitation, —(CH=CH)—, —(C≡C)—, benzyl ($R^aCH_2Ph$), halo (fluoro, chloro, bromo, iodo), aldehyde ($R^a$-CHO), acyl halide ($R^aC(O)X$) (where X is selected from fluorine, chlorine, bromine, and iodine), carbonate ($R^aOC(O)OR^b$), carboxyl ($R^aC(O)OH$), carboxylate ($R^aCOO^-$), ether ($R^aOR^b$), ester ($R^aC(O)OR^b$), hydroxyl ($R^aOH$), ketone ($R^aC(O)R^b$), silyl ether ($R^aSi(OR^d)R^bR^c$), peroxy ($R^aOOR^b$), hydroperoxy ($R^aOOH$), phosphate ($R^aOP(O)OH_2$), phosphoryl ($R^aP(O)(OH)_2$), phosphodiester [$HOP(O)(OR^a)(OR^b)$], phosphine ($R^aPR^bR^c$), thiol ($R^aSH$), thioether/sulfide ($R^aSR^b$), disulfide ($R^aSSR^b$), sulfinyl ($R^aS(O)R^b$), sulfonyl ($R^aSO_2R^b$), carbonothioyl ($R^aC(S)R^b$ or $R^aC(S)H$), sulfino ($R^aS(O)OH$), sulfo ($R^aSO_3H$), thiocyanate ($R^aSCN$), isothiocyanate ($R^aNCS$), oxazole, oxadiazole, imidazole, triazole, tetrazole, amide ($R^aC(O)NR^bR^c$), azide ($N_3$), azo ($R^aNNR^b$), cyano ($R^aOCN$), isocyanate ($R^aNCO$), imide ($R^aC(O)NR^bC(O)R^c$), nitrile ($R^aCN$), isonitrile ($R^aN^+C^-$), nitro ($R^aNO_2$), nitroso ($R^aNO$), nitromethyl ($R^aCH_2NO_2$), and amine ($NH_2$, $NHR^a$, $NR^aR^b$). With reference to these functional groups, $R^a$ is the atom of the formulas disclosed herein to which the heteroatom-containing moiety is depicted as being attached, and $R^b$, $R^c$, and $R^d$ independently are hydrogen, aliphatic, aryl, heteroaliphatic, heteroaryl, and any combination thereof.

HATU: O-(7-azabenzo-triazol-1-yl)-N,N,N',N'-tetramethyluronium hexafluorophosphate.

Hemiaminal: A functional group or type of chemical compound that has a hydroxyl group and an amine attached to the same carbon atom.

Heteroaliphatic: An aliphatic group, which contains one or more atoms other than carbon and hydrogen, such as, but not limited to, oxygen, sulfur, nitrogen, phosphorus, chlorine, fluorine, bromine, iodine, and selenium. This term also encompasses substituted heteroaliphatic compounds, saturated heteroaliphatic compounds, and unsaturated heteroaliphatic compounds.

Heteroaryl: An aryl group, which contains one or more atoms other than carbon and hydrogen, such as, but not limited to, oxygen, sulfur, nitrogen, phosphorus, silicon, boron, and selenium.

Heteroatom: Any atom that is not carbon or hydrogen. Examples include, but are not limited to, nitrogen, oxygen, sulfur, phosphorus, boron, chlorine, bromine, fluorine, and iodine.

Heteroatom-containing moiety: A moiety present in a molecule that contains at least one atom which is not carbon or hydrogen. Examples include, but are not limited to, aldehyde ($R^aCHO$), acyl halide ($RC(O)X$) (where X is selected from fluorine, chlorine, bromine, and iodine), carbonate ($R^aOC(O)OR^b$), carboxyl ($R^aC(O)OH$), carboxylate ($R^aCOO^-$), ether ($R^aOR^b$), ester ($R^aC(O)OR^b$), hydroxyl ($R^aOH$), ketone ($R^aC(O)R^b$), silyl ether ($R^aR^bR^cSiOR^d$), peroxy ($R^aOOR^b$), hydroperoxy ($R^aOOH$), phosphate ($R^aOP(O)OH_2$), phosphoryl ($R^aP(O)(OH)_2$), phosphodiester [$HOP(O)(OR^a)(OR^b)$], phosphine ($PR^aR^bR^c$), thiol ($R^aSH$), thioether/sulfide ($R^aSR$), disulfide ($R^aSSR^b$), sulfinyl ($R^aS(O)R^b$), sulfonyl ($R^aSO_2R^b$), carbonothioyl ($R^aC(S)R^b$ or $R^aC(S)H$), sulfino ($R^aS(O)OH$), sulfo ($R^aSO_3H$), thiocyanate ($R^aSCN$), isothiocyanate (RNCS), oxazole, oxadiazole, imidazole, triazole, tetrazole, amide ($R^aC(O)NR^bR^C$), azide ($N_3$), azo ($R^aNNR^b$), cyano ($R^aOCN$), isocyanate ($R^aNCO$), imide ($R^aC(O)NR^bC(O)R^c$), nitrile ($R^aCN$), isonitrile ($R^aN^+C^-$), nitro ($R^aNO_2$), nitroso ($R^aNO$), nitromethyl ($R^aCH_2NO_2$), and amine ($NH_2$, $NHR^a$, $NR^aR^b$). With reference to these functional groups, $R^a$ is the atom of the formulas disclosed herein to which the heteroatom-containing moiety is depicted as being attached, and $R^b$, $R^c$, and $R^d$ independently are hydrogen, aliphatic, aryl, heteroaliphatic, heteroaryl, and any combination thereof.

Heterocyclic: Refers to a closed-ring compound or radical thereof as a substituent bonded to another group, particularly other organic groups, where at least one atom in the ring structure is other than carbon, and typically is oxygen, sulfur and/or nitrogen.

HOBt: 1-hydroxybenzotriazole.

Homologous or homologated series: A series of organic compounds in which each successive member has one additional atom, or group of atoms, such as a methylene group (—CH$_2$) in its molecule than the preceding method. For example, methanol (CH$_3$OH), ethanol (CH$_3$CH$_2$OH), and propanol (CH$_3$(CH$_2$)$_2$OH) form a homologous series.

Inhibitor: A compound that blocks or suppresses the rate of a reaction. An enzyme inhibitor binds to an enzyme and decreases or completely blocks the enzyme's activity. A receptor inhibitor binds to a receptor and typically blocks the physiological or pharmacological response associated with the receptor.

Isomer: One of two or more molecules having the same number and kind of atoms, but differing in the arrangement or configuration of the atoms.

MeOH: Methanol.

NMR: Nuclear magnetic resonance.

Olefin: An unsaturated aliphatic hydrocarbon having one or more double bonds. Olefins with one double bond are alkenes; olefins with two double bonds are alkadienes.

Pharmacophore: A set of structural features in a molecule that is recognized at a receptor site and confers biological activity upon the molecule. IUPAC defines a pharmacophore as "an ensemble of steric and electronic features that is necessary to ensure the optimal supramolecular interactions with a specific biological target and to trigger (or block) its biological response." (Wermuth, C. G. et al., "Glossary of terms used in medicinal chemistry," *Pure Appl. Chem.*, 1998).

Polycyclic: A compound having at least 2 rings, such as aromatic rings, heteroaromatic rings, cyclic aliphatic rings, cyclic heteroaliphatic rings, and any combination thereof.

Protecting group: An atom, more particularly a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenyl-methyloxycarbonyl ("FMOC"), nitro-veratryloxycarbonyl ("NVOC"), methanesulfonyl (Ms), p-toluenesulfonyl (Ts), and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups), sulfonyl ethers, such as trifluoromethanesulfonyl (Tf), and allyl ethers.

Racemization: The partial conversion, such as by heat or chemical reaction, of one isomer into a mixture of isomers. Racemization refers particularly to the conversion of enantiomers, or optically active isomers.

Racemic: A sample/compound is racemic if there are equal amounts of two enantiomers present; the sample/compound will have zero net optical rotation.

Reductive Amination: A reaction that involves the conversion of a carbonyl group to an amine via an intermediate imine. The intermediate imine is reduced to the amine using an appropriate reducing agent.

SAR: Structure-activity relationship.

Stereoisomers: Isomers that have the same molecular formula and sequence of bonded atoms, but which differ only in the three-dimensional orientation of the atoms in space.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a hydrocarbon may have a substituent bonded thereto, such as one or more halogens, an aryl group, a cyclic group, a heteroaryl group or a heterocyclic group. Certain substituents recited herein are expressly indicated as being substituted, such as with "substituted aliphatic." However, a substituent that is not expressly recited as being substituted can nevertheless have one or more hydrogen atoms replaced with some other moiety, as will be understood by a person of ordinary skill in the art.

TEA: Triethylamine.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting. All publications, patent applications, patents, and other references mentioned herein are incorporated by reference in their entirety, unless the context clearly indicates otherwise.

III. Overview of Polycyclic Alkaloid Compounds

Particular embodiments concern synthesizing polycyclic alkaloid compounds having a general Formula 1, illustrated below. These polycyclic alkaloids have a fused six-membered aromatic ring A.

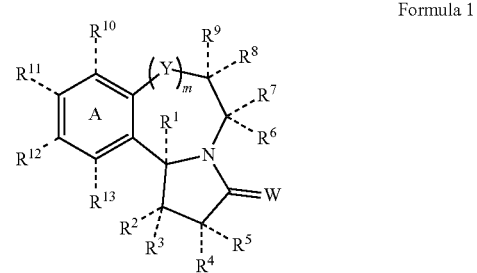

Formula 1

With reference to Formula 1, $R^1$ is selected from hydrogen, aliphatic, aryl, a heteroatom-containing moiety, or is bound to either $R^2$ or $R^3$, to form a four-, five-, six-membered, or seven-membered cyclic aliphatic, such as a cyclic alkane, alkene, a four-, five-, or seven-membered cyclic heterocycle. In particular embodiments, $R^1$ is an aliphatic chain bound to $R^2$ or $R^3$ or a heteroaliphatic chain bound to either $R^2$ or $R^3$.

$R^2$ and $R^3$ independently are selected from hydrogen, aliphatic, aryl, aliphatic and bound to $R^1$, heteroaliphatic and bound to $R^1$, or where $R^1$ is hydrogen, $R^2$ and $R^3$ may be aliphatic and bound together to form a five-, six-, or seven-membered cyclic aliphatic, such as a cyclic alkane or alkene, or heteroaliphatic and bound together to form a five-, six-, or seven-membered heterocycle.

In particular embodiments, $R^4$, $R^5$, $R^6$, $R^7$, $R^8$, and $R^9$ independently are selected from aliphatic, aryl, halogen, a heteroatom-containing moiety, hydrogen, or any $R^5$, $R^6$, $R^7$, $R^8$, and $R^9$ combination thereof. In particular embodiments, $R^4$, independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. In particular embodiments, $R^6$ or $R^7$ and at least one of $R^8$ or $R^9$ can be selected to form, together with the atom to which each is attached, a four-, five-, six-, or seven-membered cyclic aliphatic, such as cyclic alkane or alkene, or a four-, five-, six-, or seven-membered heterocycle. In other embodiments, $R^7$ and $R^9$ are not present in the molecule, the carbon atoms bearing $R^6$ and $R^8$ are bound via a double bond, and $R^6$ and $R^8$ are selected to form, together with the atom to which each is attached, a five-, six-, or seven-membered aromatic or heteroaromatic ring. In other embodiments, $R^6$ and $R^8$ are not present in the molecule, the carbon atoms bearing $R^7$ and $R^9$ are bonded via a double bond, and $R^7$ and $R^9$ are selected to form, together with the atom to which each is attached, a five-, six-, or seven-membered aromatic or heteroaromatic ring.

$R^{10}$, $R^{11}$, $R^{12}$, and $R^{13}$ independently are selected from aliphatic, aryl, halogen, a heteroatom-containing moiety, hydrogen, and any combination thereof. In particular embodiments, $R^{10}$, $R^{11}$, $R^{12}$, and $R^{13}$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. W is selected from oxygen, sulfur, and $NR^{17}$ wherein $R^{17}$ is selected from aliphatic, aryl, heteroaliphatic, heteroaryl, and hydrogen; Y is selected from a heteroatom, such as oxygen, sulfur, and any oxidized form of sulfur, such as (but not limited to) sulfonyl and sulfinyl, $—(CH_2)—$, $—(CHR^{17})—$, and $—(CR^{17}R^{18})—$; and m is zero or one.

Particular embodiments concern polycyclic alkaloids having the general formulas illustrated below.

Formula 2

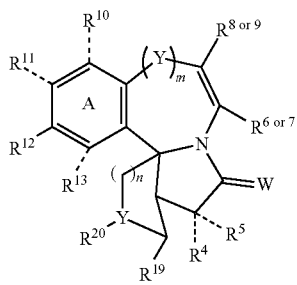

Formula 3

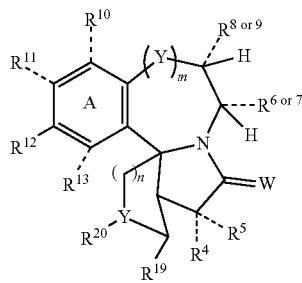

Formula 4

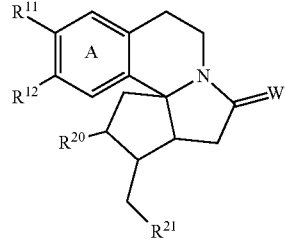

Formula 5

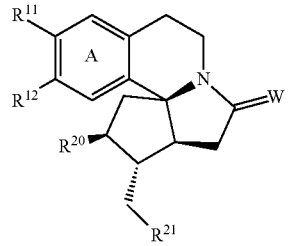

With reference to Formulas 2-5, $R^4$, $R^5$, $R^6$, $R^8$, $R^{10}$, $R^{11}$, $R^{12}$, and $R^{13}$, each Y independently, and W are as previously recited. $R^{19}$, $R^{20}$, and $R^{21}$ independently are selected from aliphatic, aryl, halogen, a heteroatom-containing moiety, and hydrogen. In particular embodiments, $R^{19}$, $R^{20}$, and $R^{21}$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof; and n is 1 or 2.

In particular embodiments, the polycyclic alkaloids have the following structures, wherein $R^6$, $R^8$, $R^{10}$, $R^{11}$, $R^{17}$, and $R^{19}$ are as stated above.

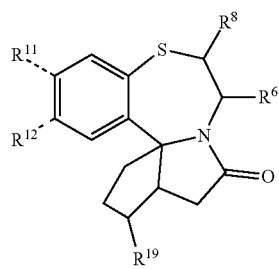

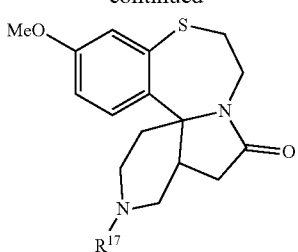
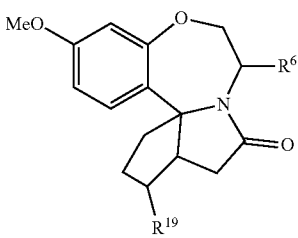
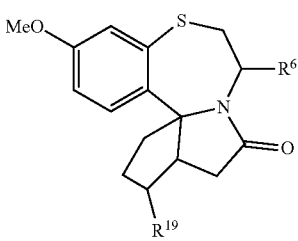
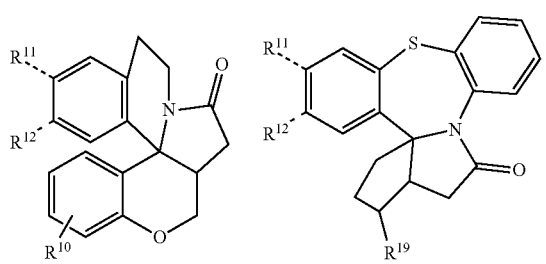
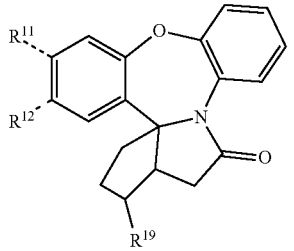
In yet further embodiments, the polycyclic alkaloids have the following structures.
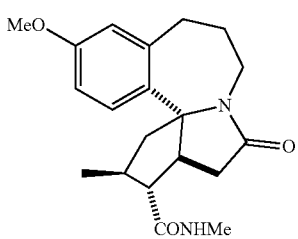
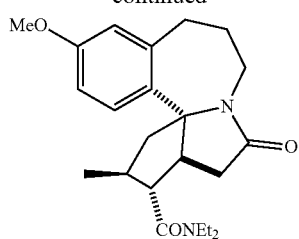
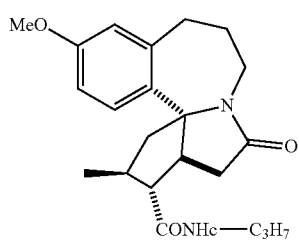
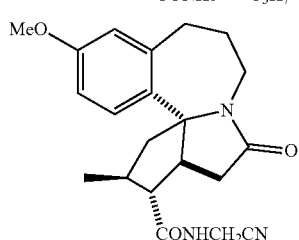
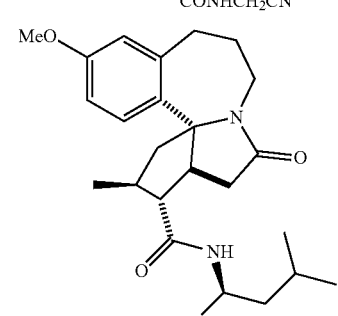
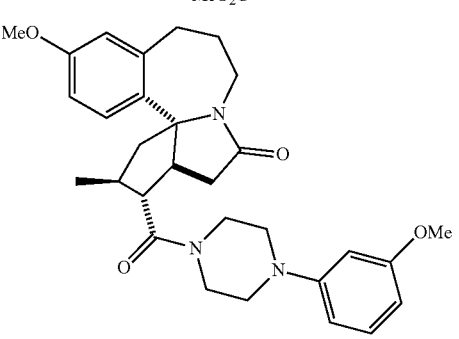
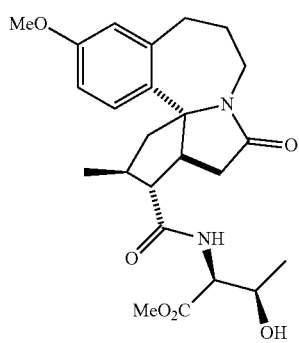

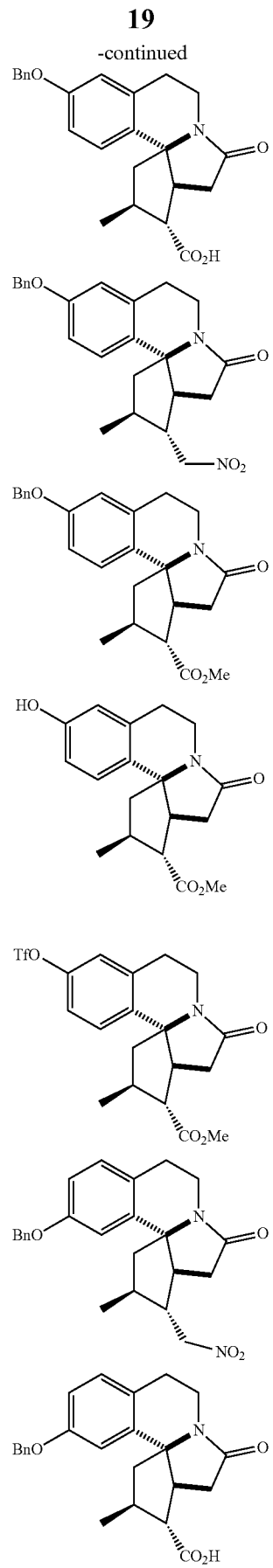
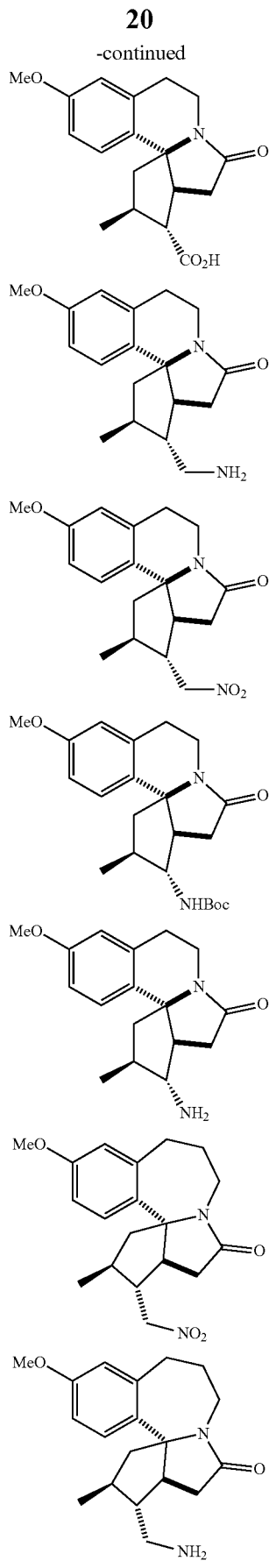

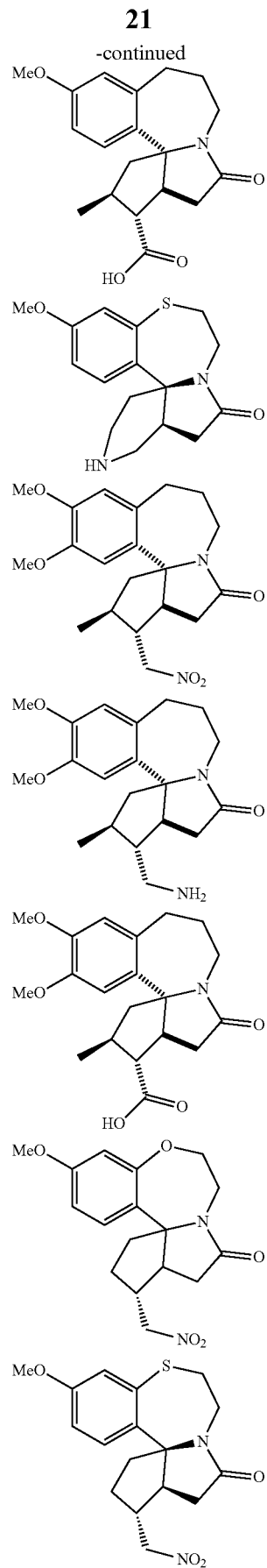
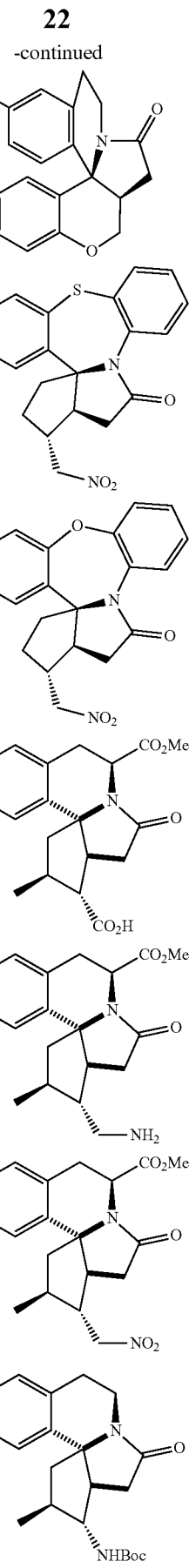

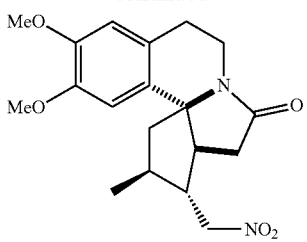
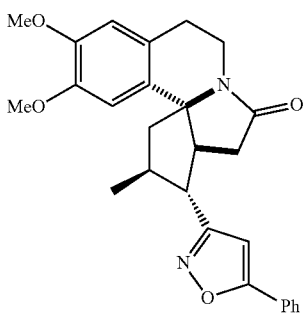
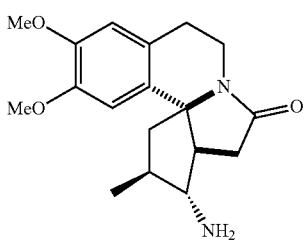
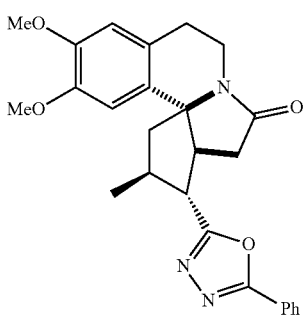
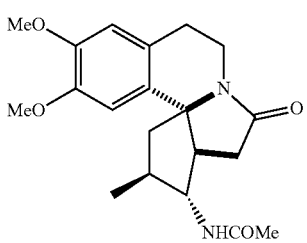
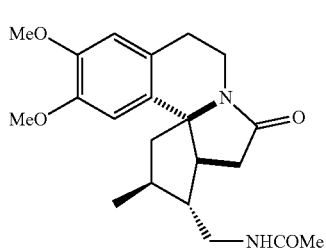
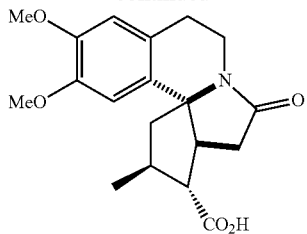
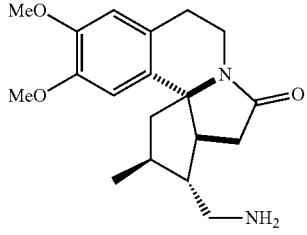
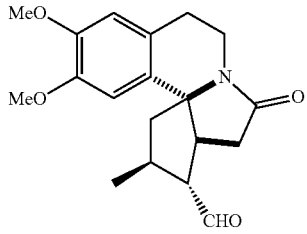
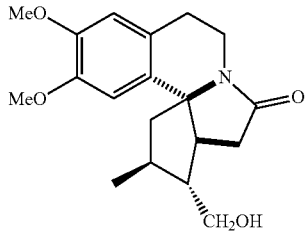
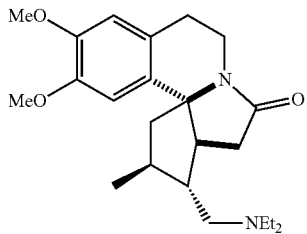
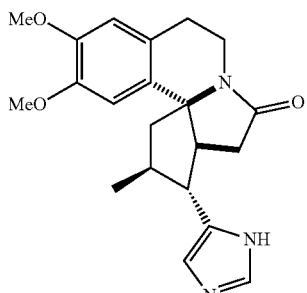
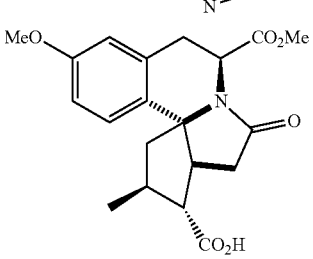

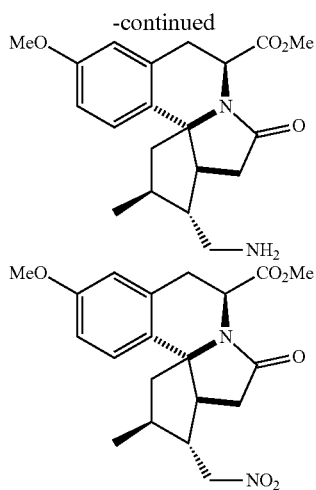

In certain embodiments, the polycyclic alkaloid can have a general Formula 6, illustrated below.

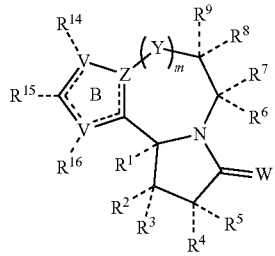

Formula 6

With reference to Formula 6, $R^1$ is selected from hydrogen, aliphatic, aryl, a heteroatom-containing moiety, or is bound to either $R^2$ or $R^3$, to form a four-, five-, or seven-membered cyclic aliphatic, such as a cyclic alkane, alkene, a four-, five-, or seven-membered cyclic heterocycle. In particular embodiments, $R^1$ is an aliphatic chain bound to $R^2$ or $R^3$ or a heteroaliphatic chain bound to either $R^2$ or $R^3$.

$R^2$ and $R^3$ independently are selected from hydrogen, aliphatic, aryl, aliphatic and bound to $R^1$, heteroaliphatic and bound to $R^1$, or, where $R^1$ is hydrogen, $R^2$ and $R^3$ may be aliphatic and bound together to form a five-, six-, or seven-membered cyclic aliphatic, such as a cyclic alkane or alkene, or heteroaliphatic and bound together to form a five-, six-, or seven-membered heterocycle.

In particular embodiments, $R^4$, $R^5$, $R^6$, $R^7$, $R^8$, and $R^9$ independently are selected from aliphatic, aryl, halogen, a heteratom-containing moiety, hydrogen, or any combination thereof. In particular embodiments, $R^4$, $R^5$, $R^6$, $R^7$, $R^8$, and $R^9$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. In particular embodiments, $R^6$ or $R^7$ and at least one of $R^8$ or $R^9$ can be selected to form, together with the atom to which each is attached, a four-, five-, six-, or seven-membered cyclic aliphatic, such as cyclic alkane or alkene, or a four-, five-, six-, or seven-membered heterocycle. In other embodiments, $R^7$ and $R^9$ are not present in the molecule, the carbon atoms bearing $R^6$ and $R^8$ are bound via a double bond, and $R^6$ and $R^8$ are selected to form, together with the atom to which each is attached, a five-, six-, or seven-membered aromatic or heteroaromatic ring. In other embodiments, $R^6$ and $R^8$ are not present in the molecule, the carbon atoms bearing $R^7$ and $R^9$ are bonded via a double bond, and $R^7$ and $R^9$ are selected to form, together with the atom to which each is attached, a five-, six-, or seven-membered aromatic or heteroaromatic ring.

$R^{14}$, $R^{15}$, and $R^{16}$ independently can be selected from aliphatic, aryl, halogen, a heteroatom-containing moiety, heteroaliphatic, heteroaryl, and hydrogen; and m is zero or one. In particular embodiments, $R^{14}$, $R^{15}$, and $R^{16}$ independently can be selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. In particular embodiments, $R^{14}$ and $R^{15}$ together can be selected to form, together with the atom to which each is attached, a four-, five-, six-, or seven-membered cyclic aliphatic, such as a cyclic alkane or alkene, a four-, five-, six-, or seven-membered heterocycle, or a five-, six-, or seven-membered aromatic or heteroaromatic ring. In other embodiments, $R^{15}$ and $R^{16}$ together can be selected to form, together with the atom to which each is attached, a four-, five-, six-, or seven-membered cyclic aliphatic, such as a cyclic alkane or alkene, a four-, five-, six-, or seven-membered heterocycle, or a five-, six-, or seven-membered aromatic or heteroaromatic ring.

W is selected from oxygen, sulfur, and $NR^{17}$ wherein $R^{17}$ is selected from aliphatic, aryl, heteroaliphatic, heteroaryl, and hydrogen; Y is selected from —(CH$_2$)—, —(CHR$^{17}$)—, and —(CR$^{17}$R$^{18}$)—, oxygen, sulfur, any oxidized form of sulfur, such as (but not limited to) sulfonyl and sulfinyl, and $NR^{17}$ wherein $R^{17}$ is selected from aliphatic, aryl, heteroaliphatic, heteroaryl, and hydrogen, V independently is selected from an sp3 or sp2 carbon atom, oxygen, sulfur, nitrogen, and $NR^{17}$ wherein $R^{17}$ is selected from aliphatic, aryl, heteroaliphatic, heteroaryl, and hydrogen, and any combination thereof; Z is selected from an sp3 or sp2 carbon atom, (CR$^{17}$), or nitrogen; and m is zero or one.

Particular embodiments of polycyclic alkaloids having a fused five-membered ring B are illustrated in Formulas 7-10.

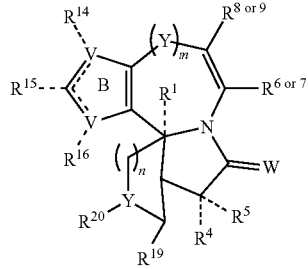

Formula 7

Formula 8

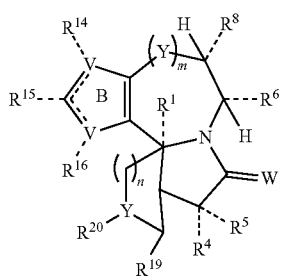

Formula 9

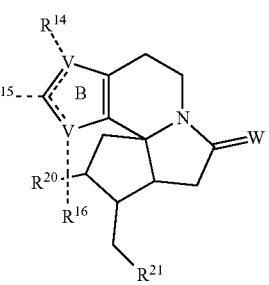

Formula 10

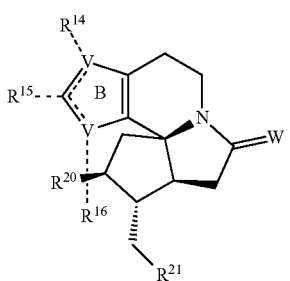

With reference to Formulas 7-10, $R^4$, $R^5$, $R^6$, $R^8$, $R^{14}$, $R^{15}$, $R^{16}$, W, each Y independently, V, n, and m are as previously recited. $R^{19}$, $R^{20}$, and $R^{21}$ independently are selected from aliphatic, aryl, halogen, a heteroatom-containing moiety, and hydrogen. In particular embodiments, $R^{19}$, $R^{20}$, and $R^{21}$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof.

Particular embodiments of polycyclic alkaloids having a five-membered aromatic ring B have the following structures.

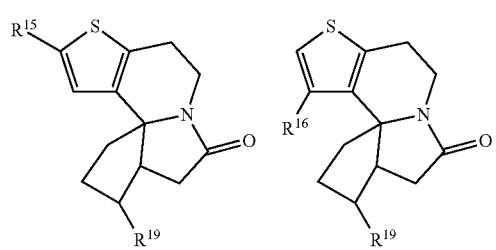

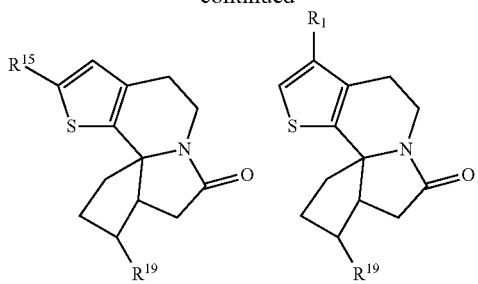

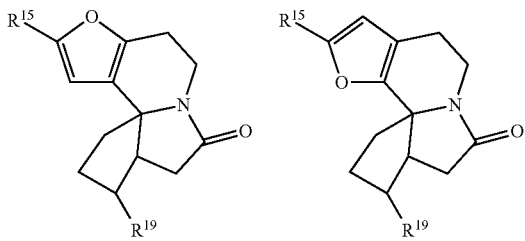

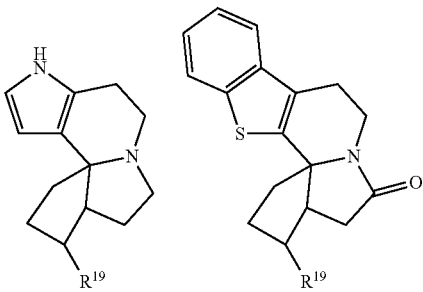

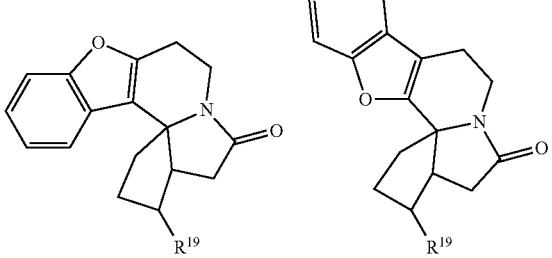

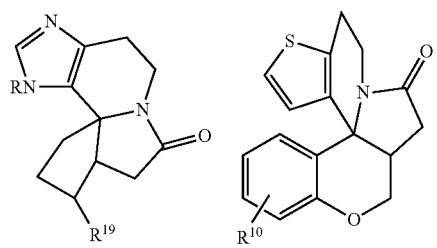

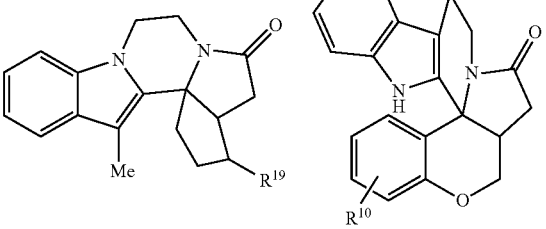

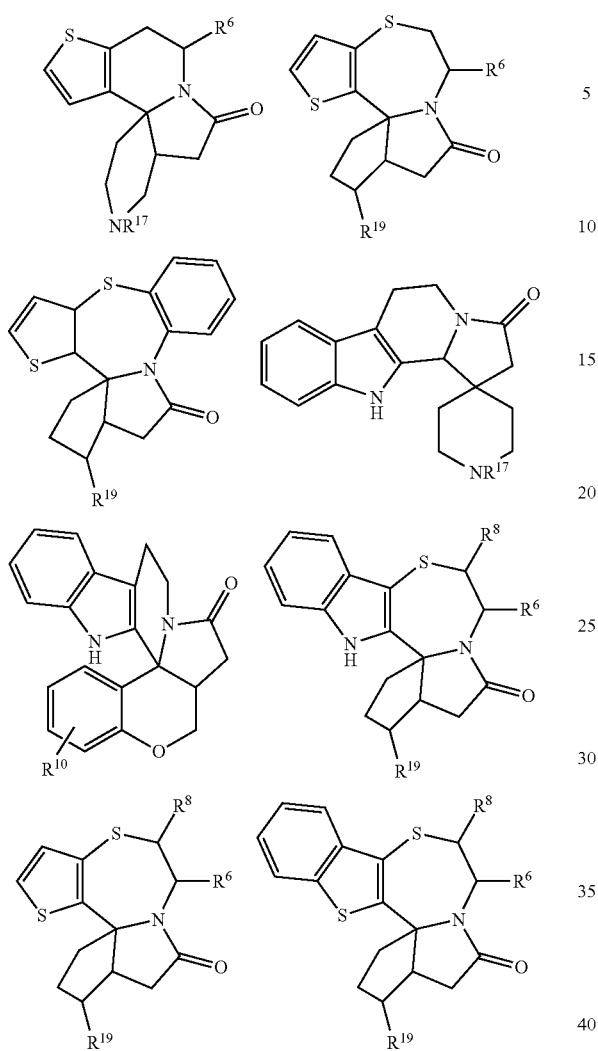
Particular working embodiments have the following structures.
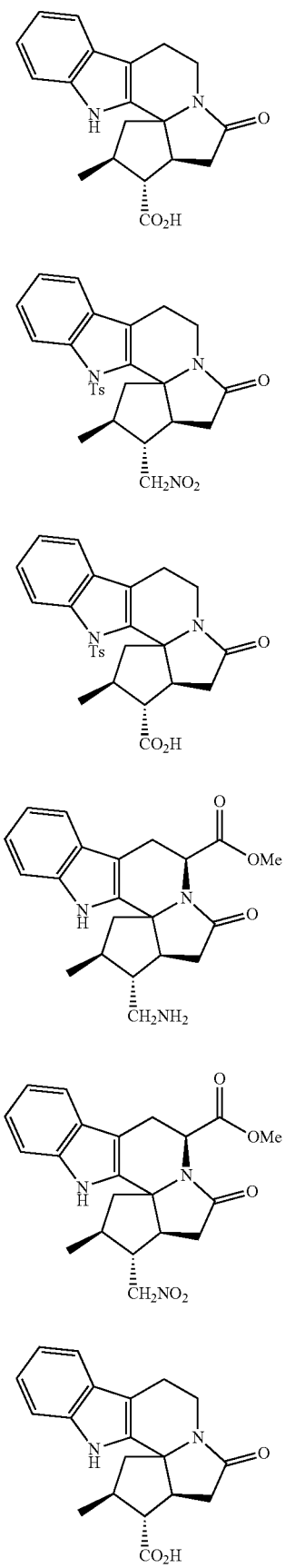

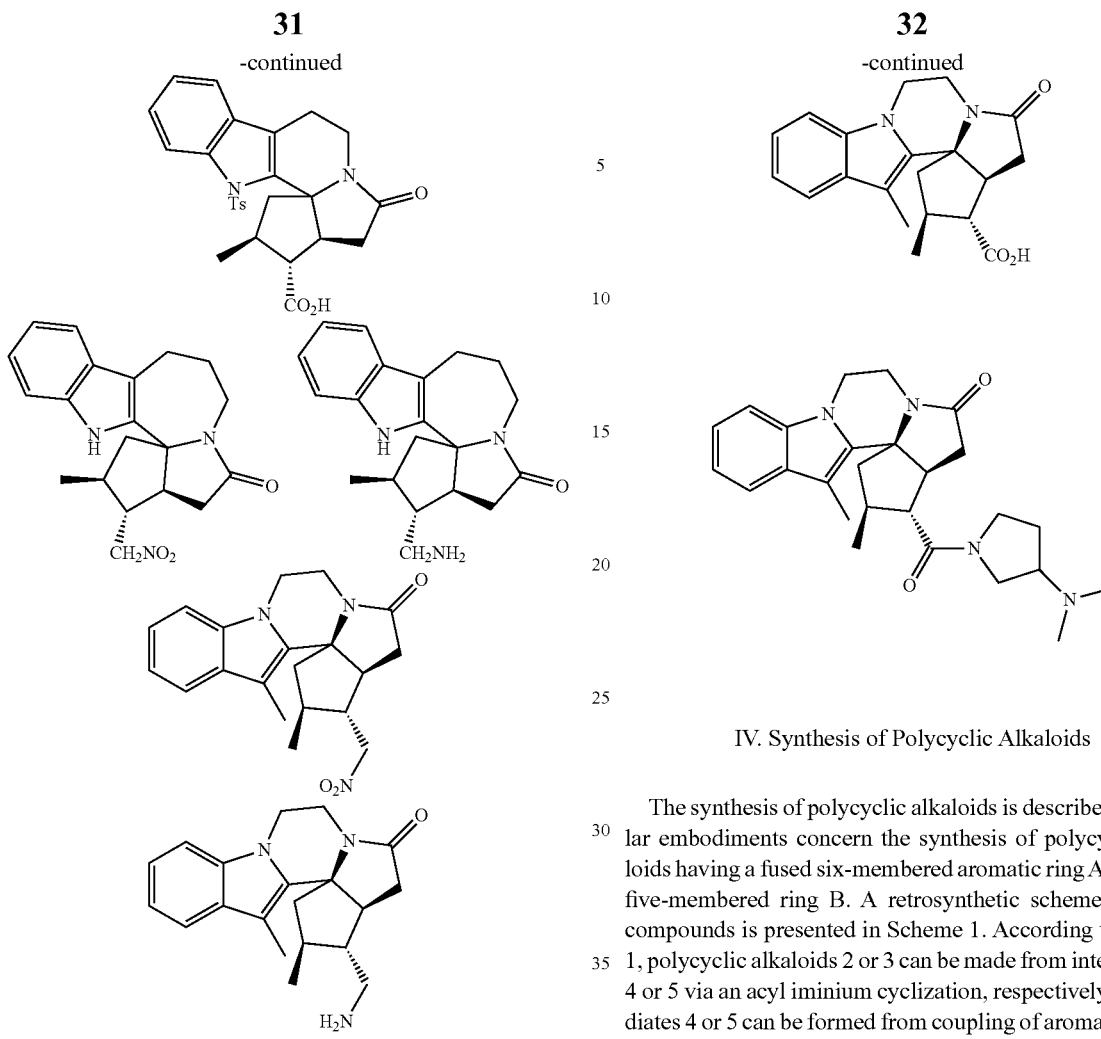

IV. Synthesis of Polycyclic Alkaloids

The synthesis of polycyclic alkaloids is described. Particular embodiments concern the synthesis of polycyclic alkaloids having a fused six-membered aromatic ring A or a fused five-membered ring B. A retrosynthetic scheme for these compounds is presented in Scheme 1. According to Scheme 1, polycyclic alkaloids 2 or 3 can be made from intermediates 4 or 5 via an acyl iminium cyclization, respectively. Intermediates 4 or 5 can be formed from coupling of aromatic amines 6 or 7, respectively, with carboxylic acid 8.

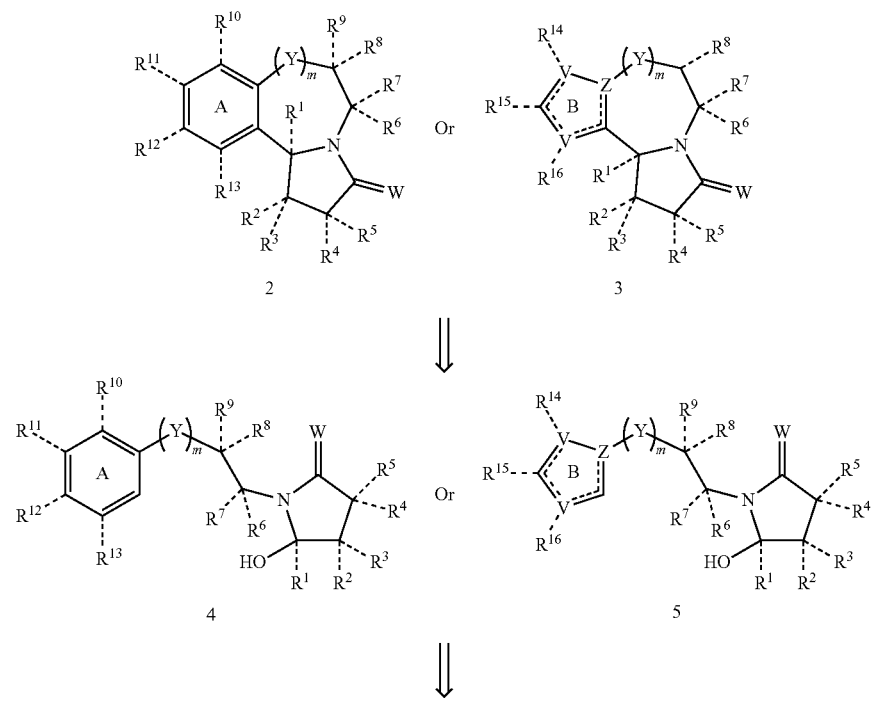

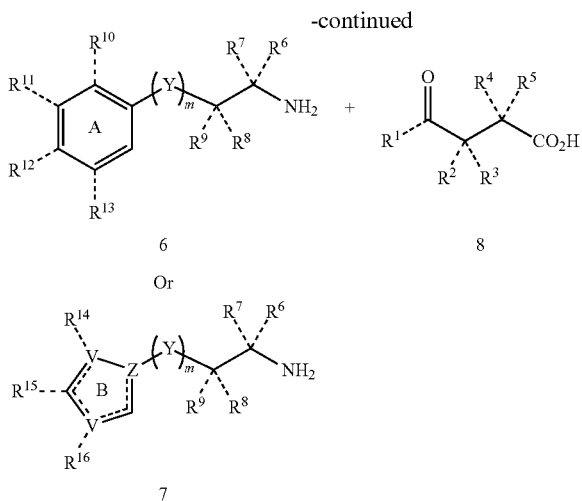

With reference to Scheme 1, $R^1$ is selected from hydrogen, aliphatic, aryl, a heteroatom-containing moiety, or is bound to either $R^2$ or $R^3$, to form a four-, five-, or seven-membered cyclic aliphatic, such as a cyclic alkane, alkene, a four-, five-, or seven-membered cyclic heterocycle. In particular embodiments, $R^1$ is an aliphatic chain bound to $R^2$ or $R^3$ or a heteroaliphatic chain bound to either $R^2$ or $R^3$.

$R^2$ and $R^3$ independently are selected from hydrogen, aliphatic, aryl, aliphatic and bound to $R^1$, heteroaliphatic and bound to $R^1$, or, where $R^1$ is hydrogen, $R^2$ and $R^3$ may be aliphatic and bound together to form a five-, six-, or seven-membered cyclic aliphatic, such as a cyclic alkane or alkene, or heteroaliphatic and bound together to form a five-, six-, or seven-membered heterocycle.

In particular embodiments, $R^4$, $R^5$, $R^6$, $R^7$, $R^8$, and $R^9$ independently are selected from aliphatic, aryl, halogen, a heteroatom-containing moiety, hydrogen, or any combination thereof. In particular embodiments, $R^4$, $R^5$, $R^6$, $R^7$, $R^8$, and $R^9$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. In particular embodiments, $R^6$ or $R^7$ and at least one of $R^8$ or $R^9$ can be selected to form, together with the atom to which each is attached, a four-, five-, six-, or seven-membered cyclic aliphatic, such as cyclic alkane or alkene, or a four-, five-, six-, or seven-membered heterocycle. In other embodiments, $R^7$ and $R^9$ are not present in the molecule, the carbon atoms bearing $R^6$ and $R^8$ are bound via a double bond, and $R^6$ and $R^8$ are selected to form, together with the atom to which each is attached, a five-, six-, or seven-membered aromatic or heteroaromatic ring. In other embodiments, $R^6$ and $R^8$ are not present in the molecule, the carbon atoms bearing $R^7$ and $R^9$ are bonded via a double bond, and $R^7$ and $R^9$ are selected to form, together with the atom to which each is attached, a five-, six-, or seven-membered aromatic or heteroaromatic ring.

$R^{10}$, $R^{11}$, $R^{12}$, and $R^{13}$ independently are selected from aliphatic, aryl, halogen, a heteroatom-containing moiety, hydrogen, and any combination thereof. In particular embodiments, $R^{10}$, $R^{11}$, $R^{12}$, and $R^{13}$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof.

$R^{14}$, $R^{15}$, and $R^{16}$ independently can be selected from aliphatic, aryl, halogen, a heteroatom-containing moiety, heteroaliphatic, heteroaryl, and hydrogen; and m is zero or one. In particular embodiments, $R^{14}$, $R^{15}$, and $R^{16}$ independently can be selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. In particular embodiments, $R^{14}$ and $R^{15}$ together can be selected to form, together with the atom to which each is attached, a four-, five-, six-, or seven-membered cyclic aliphatic, such as a cyclic alkane or alkene, a four-, five-, six-, or seven-membered heterocycle, or a five-, six-, or seven-membered aromatic or heteroaromatic ring. In other embodiments, $R^{15}$ and $R^{16}$ together can be selected to form, together with the atom to which each is attached, a four-, five-, six-, or seven-membered cyclic aliphatic, such as a cyclic alkane or alkene, a four-, five-, six-, or seven-membered heterocycle, or a five-, six-, or seven-membered aromatic or heteroaromatic ring.

W is selected from oxygen, sulfur, and $NR^{17}$ wherein $R^{17}$ is selected from aliphatic, aryl, heteroaliphatic, heteroaryl, and hydrogen; Y is selected from $—(CH_2)—$, $—(CHR^{17})—$, and $—(CR^{17}R^{18})—$, oxygen, sulfur, any oxidized form of sulfur, such as (but not limited to) sulfonyl and sulfinyl, and $NR^{17}$ wherein $R^{17}$ is selected from aliphatic, aryl, heteroaliphatic, heteroaryl, and hydrogen, V independently is selected from an sp3 or sp2 carbon atom, oxygen, sulfur, nitrogen, and $NR^{17}$ wherein $R^{17}$ is selected from aliphatic, aryl, heteroaliphatic, heteroaryl, and hydrogen, and any combination thereof; Z is selected from an sp3 or sp2 carbon atom, $(CR^{17})$, or nitrogen; and m is zero or one.

The retrosynthetic scheme for polycyclic alkaloids having a fused six-membered ring A is illustrated in Scheme 2, where the substituents are as recited above.

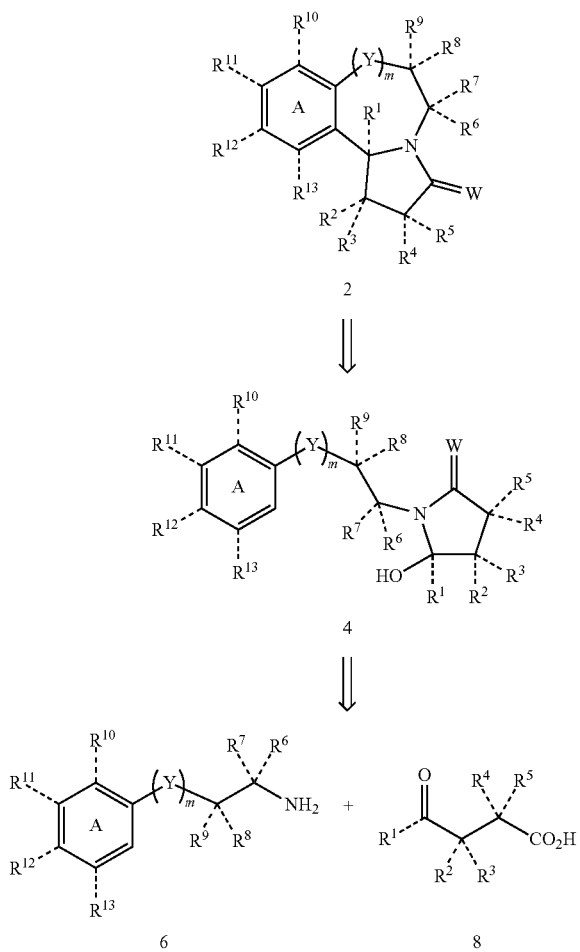

An exemplary retrosynthesis of particular embodiments is illustrated in Scheme 3. A person of ordinary skill in the art will recognize that compounds 10, 12, and 16 can either be racemic or diastereomerically pure.

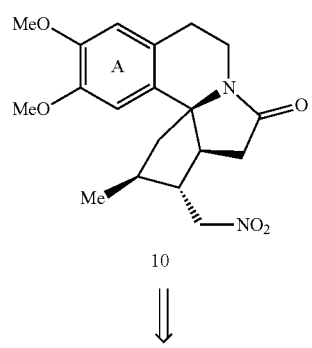

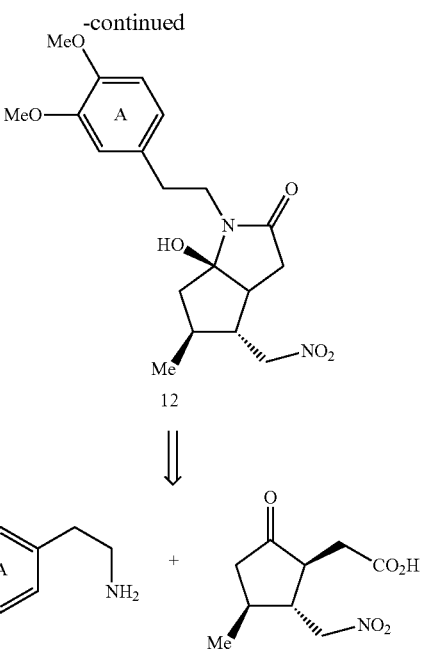

The forward synthesis of the polycyclic alkaloids having a fused six-membered aromatic ring A begins with the formation of a hemiaminal intermediate 4, as illustrated in Scheme 4. This conversion concerns coupling amine 6 with carboxylic acid 8 using any reagent known to a person of ordinary skill in the art to activate the carboxylic acid moiety present in carboxylic acid 8, including, but not limited to, N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-azabenzotriazole (HOAt), and o-(7-azabenzotriazol-1-yl)-N,N,N',N'-tetramethyluronium hexafluorophosphate (HATU), or any combination thereof. The coupling reaction also utilizes a base useful for amide bond formation including, but not limited to, aliphatic amines, such as triethylamine, 1,8-diazabicycloundec-7-ene, 1,4-diazabicyclo[2.2.2]octane, and diisopropylethylamine. Following amide formation, the molecule can undergo intramolecular hemiaminal formation providing in hemiaminal intermediate 4. A person of ordinary skill in the art will recognize that amine 6, carboxylic acid 8 and hemiaminal intermediate 4 can be diastereomerically pure or racemic. A person of ordinary skill in the art will recognize that the hemiaminal intermediate may be isolated, but need not be in order for subsequent reactions to be carried out.

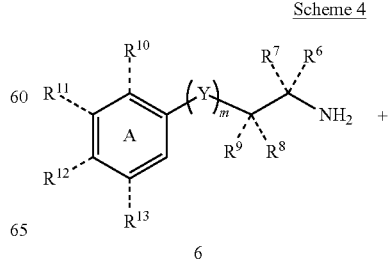

-continued

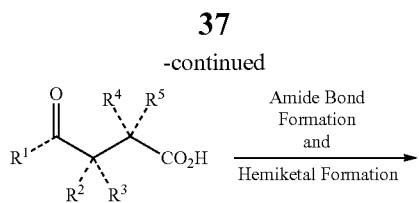

8

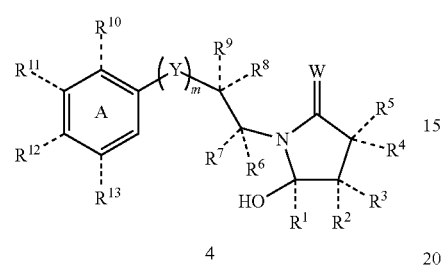

4

In particular embodiments, the amide bond formation and hemiaminal formation were performed with amine 14, 18, 22, 26, and 30 and carboxylic acid 16 to form any one of hemiaminals 12, 20, 24, 28, and 32 (Scheme 5). Particular embodiments concern using EDC, HOBt, and Et₃N in dichloromethane to carry out the reactions. A person of ordinary skill in the art will recognize that even though a particular stereochemistry is illustrated in Scheme 5, other stereoisomers of carboxylic acid 16 can be utilized in the current reaction. In particular embodiments, hemiaminal formation resulted in forming a cis-fused ring system, as illustrated in Scheme 4.

Scheme 5

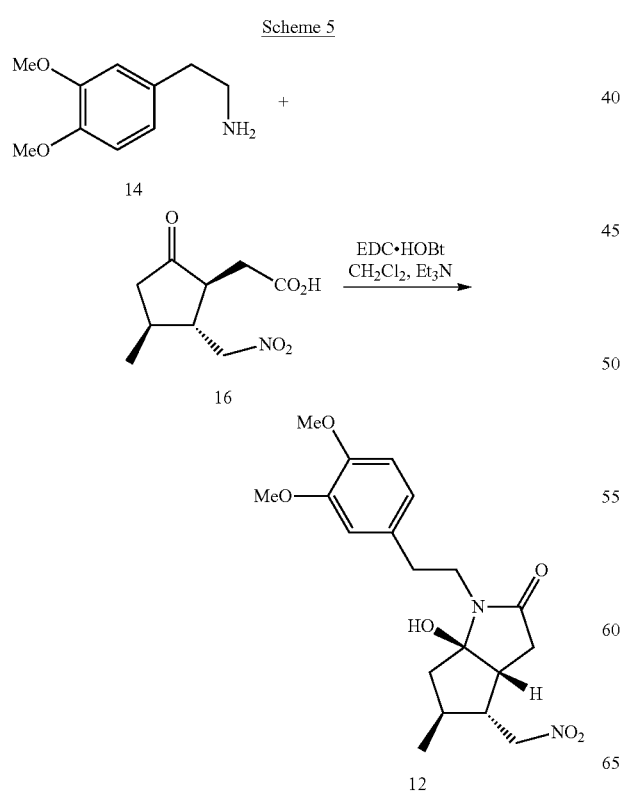

Scheme 5

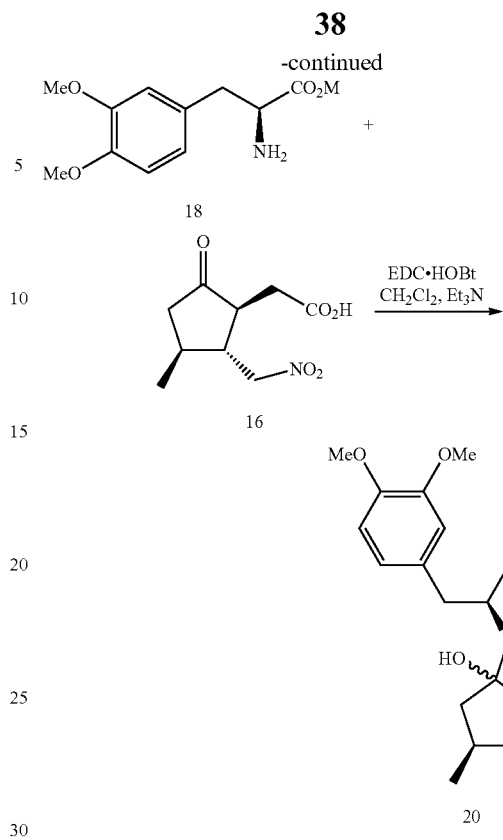

-continued

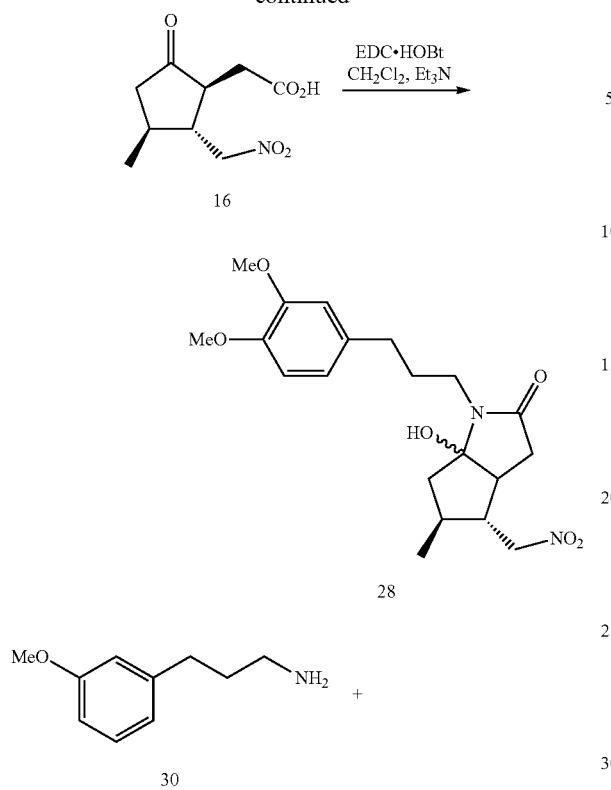

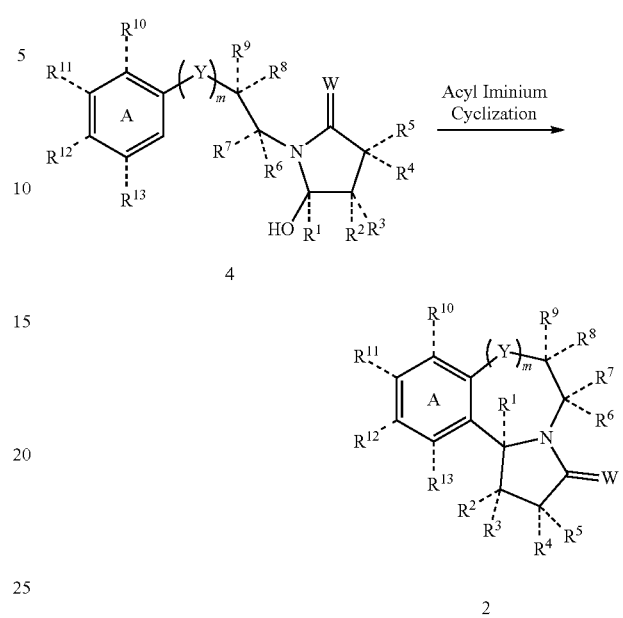

Scheme 6

In particular embodiments, the acyl iminium cyclization was carried out using TFA in dichloromethane at room temperature, or p-TsOH in toluene at refluxing temperature (Scheme 7). Both reagents and reaction conditions resulted in forming polycyclic alkaloids 10, 34, 36, 38, and 40. A person of ordinary skill in the art will recognize that compounds 12, 20, 24, 28, 32, 10, 34, 36, 38, and 40 can have the particular stereochemistry illustrated in Scheme 7, any combination of diastereomers, or they can be racemic.

Scheme 7

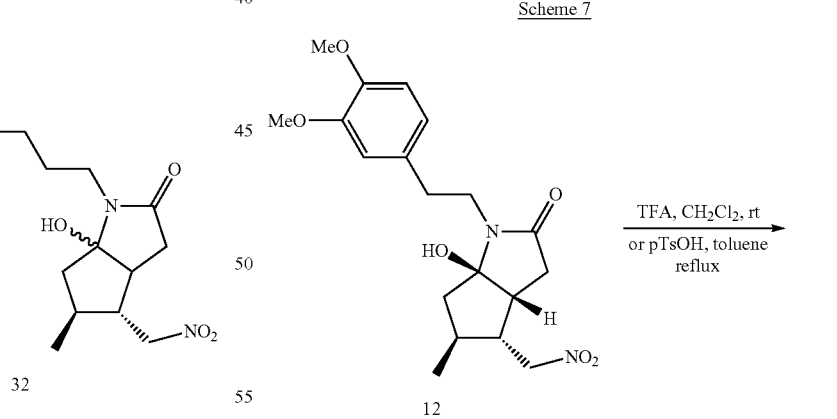

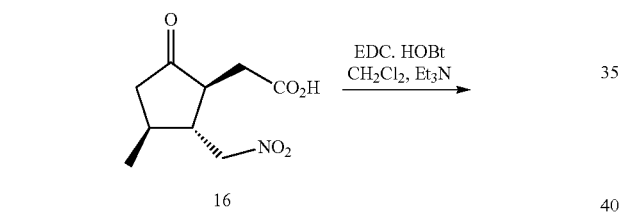

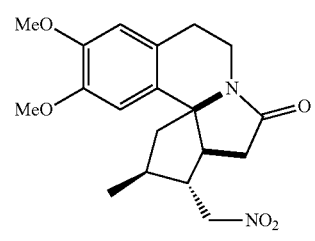

Once hemiaminal intermediate 4 is formed, it can be subjected to reaction conditions effective in promoting an acyl iminium cyclization (Scheme 6). Conditions suitable for promoting an acyl iminium cyclization can include using an acid, particularly an organic acid, such as, but not limited to, trifluoroacetic acid, p-toluenesulfonic acid, and camphorsulfonic acid. Treating a hemiaminal with an appropriate acid forms the desired polycyclic alkaloid 2. $R^1$, $R^2$, $R^3$, $R^4$, $R^5$, $R^6$, $R^7$, $R^8$, $R^9$, $R^{10}$, $R^{11}$, $R^{12}$, $R^{13}$, Y, W, and m are as previously described.

-continued

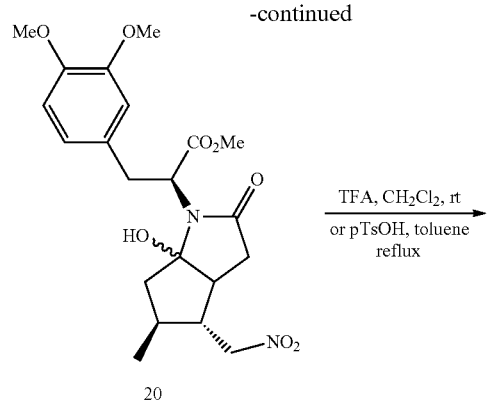
20

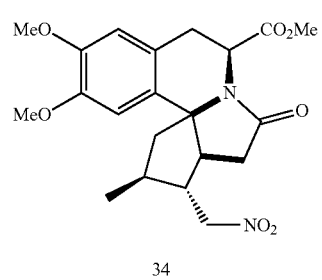
34

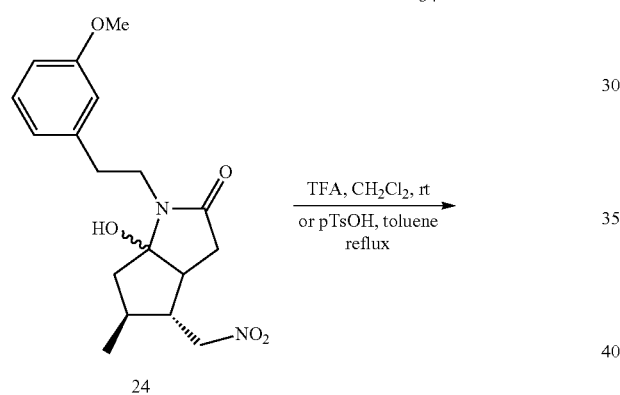
24

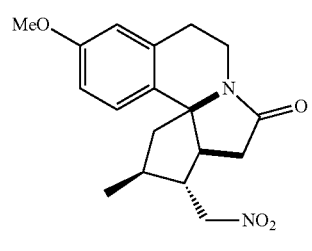
36

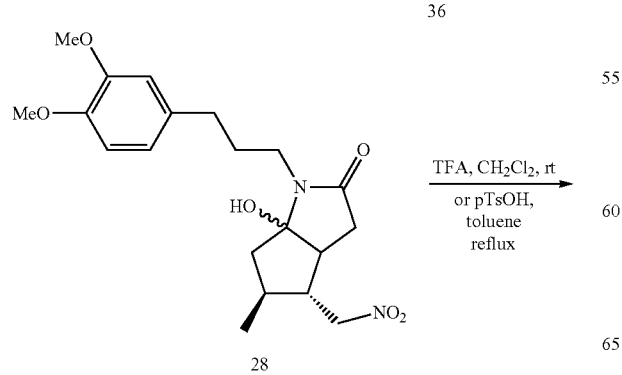
28

-continued

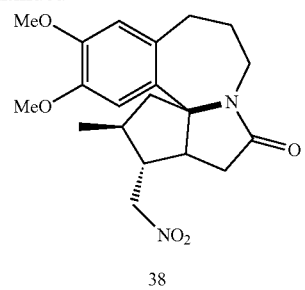
38

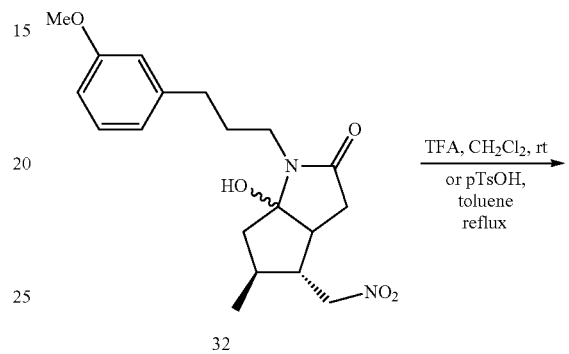
32

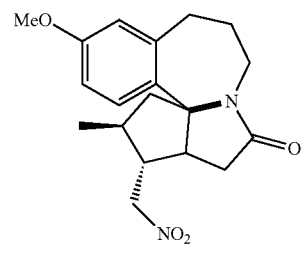
40

Particular embodiments concern the synthesis of polycyclic alkaloids having a fused five-membered aromatic ring B. A retrosynthetic scheme for these compounds is presented in Scheme 8. According to Scheme 8, polycyclic alkaloid 3 can be formed from hemiaminal intermediate 5 via an acyl iminium cyclization. Hemiaminal intermediate 5 can be formed by coupling aromatic amines 7 with carboxylic acid 8.

Scheme 8

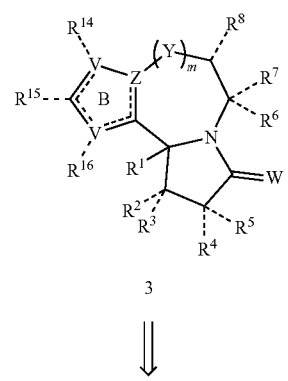
3

⇓

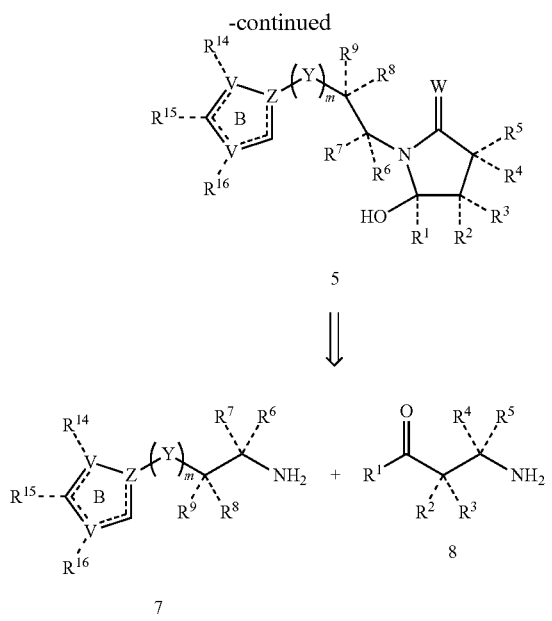

With reference to Scheme 8, $R^1$ is selected from hydrogen, aliphatic, aryl, a heteroatom-containing moiety, or is bound to either $R^2$ or $R^3$, to form a four-, five-, or seven-membered cyclic aliphatic, such as a cyclic alkane, alkene, a four-, five-, or seven-membered cyclic heterocycle. In particular embodiments, $R^1$ is an aliphatic chain bound to $R^2$ or $R^3$ or a heteroaliphatic chain bound to either $R^2$ or $R^3$. $R^2$ and $R^3$ independently are selected from hydrogen, aliphatic, aryl, aliphatic and bound to $R^1$, heteroaliphatic and bound to $R^1$, or, where $R^1$ is hydrogen, $R^2$ and $R^3$ may be aliphatic and bound together to form a five-, six-, or seven-membered cyclic aliphatic, such as a cyclic alkane or alkene, or heteroaliphatic and bound together to form a five-, six-, or seven-membered heterocycle.

In particular embodiments, $R^4$, $R^5$, $R^6$, $R^7$, $R^8$, and $R^9$ independently are selected from aliphatic, aryl, halogen, a heteroatom-containing moiety, hydrogen, or any combination thereof. In particular embodiments, $R^4$, $R^5$, $R^6$, $R^7$, $R^8$, and $R^9$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. In particular embodiments, $R^6$ or $R^7$ and at least one of $R^8$ or $R^9$ can be selected to form, together with the atom to which each is attached, a four-, five-, six-, or seven-membered cyclic aliphatic, such as cyclic alkane or alkene, or a four-, five-, six-, or seven-membered heterocycle. In other embodiments, $R^7$ and $R^9$ are not present in the molecule, the carbon atoms bearing $R^6$ and $R^8$ are bound via a double bond, and $R^6$ and $R^8$ are selected to form, together with the atom to which each is attached, a five-, six-, or seven-membered aromatic or heteroaromatic ring. In other embodiments, $R^6$ and $R^8$ are not present in the molecule, the carbon atoms bearing $R^7$ and $R^9$ are bonded via a double bond, and $R^7$ and $R^9$ are selected to form, together with the atom to which each is attached, a five-, six-, or seven-membered aromatic or heteroaromatic ring.

$R^{14}$, $R^{15}$, and $R^{16}$ independently can be selected from aliphatic, aryl, halogen, a heteroatom-containing moiety, heteroaliphatic, heteroaryl, and hydrogen; and m is zero or one. In particular embodiments, $R^{14}$, $R^{15}$, and $R^{16}$ independently can be selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof. In particular embodiments, $R^{14}$ and $R^{15}$ together can be selected to form, together with the atom to which each is attached, a four-, five-, six-, or seven-membered cyclic aliphatic, such as a cyclic alkane or alkene, a four-, five-, six-, or seven-membered heterocycle, or a five-, six-, or seven-membered aromatic or heteroaromatic ring. In other embodiments, $R^{15}$ and $R^{16}$ together can be selected to form, together with the atom to which each is attached, a four-, five-, six-, or seven-membered cyclic aliphatic, such as a cyclic alkane or alkene, a four-, five-, six-, or seven-membered heterocycle, or a five-, six-, or seven-membered aromatic or heteroaromatic ring. W is selected from oxygen, sulfur, and $NR^{17}$ wherein $R^{17}$ is selected from aliphatic, aryl, heteroaliphatic, heteroaryl, and hydrogen; Y is selected from —$(CH_2)$—, —$(CHR^{17})$—, and —$(CR^{17}R^{18})$—, oxygen, sulfur, any oxidized form of sulfur, such as (but not limited to) sulfonyl and sulfinyl, and $NR^{17}$ wherein $R^{17}$ is selected from aliphatic, aryl, heteroaliphatic, heteroaryl, and hydrogen, V independently is selected from an sp3 or sp2 carbon atom, oxygen, sulfur, nitrogen, and $NR^{17}$ wherein $R^{17}$ is selected from aliphatic, aryl, heteroaliphatic, heteroaryl, and hydrogen, and any combination thereof; Z is selected from an sp3 or sp2 carbon atom, $(CR^{17})$, or nitrogen; and m is zero or one.

An exemplary retrosynthesis of particular embodiments is illustrated in Scheme 9. A person of ordinary skill in the art will recognize that compounds 48, 50, and 16 can possess the stereochemistry as illustrated or any combination thereof.

Scheme 9

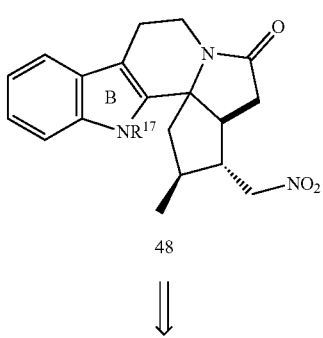

48

-continued

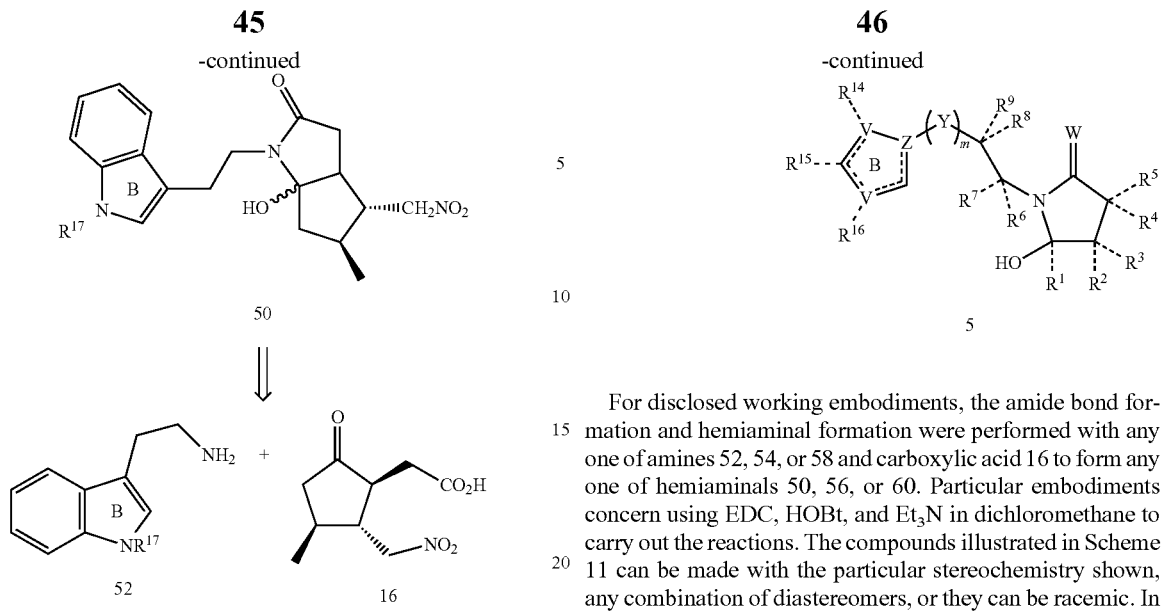

50

The forward synthesis of the polycyclic alkaloids having a fused five-membered aromatic ring B begins by making a hemiaminal intermediate 5 (Scheme 10). This conversion concerns coupling amine 7 with carboxylic acid 8 using any reagent known to a person of ordinary skill in the art to activate the carboxylic acid moiety present in carboxylic acid 8, including, but not limited to, N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-aza-benzotriazole (HOAt), and o-(7-azabenzotriazol-1-yl)-N,N,N',N'-tetramethyluronium hexafluorophosphate (HATU), or any combination thereof. The coupling reaction also utilizes a base useful for amide bond formation including, but not limited to, aliphatic amines, such as triethylamine, 1,8-diazabicycloundec-7-ene, 1,4-diazabicyclo[2.2.2]octane, and diisopropylethylamine. Following amide formation, the molecule can undergo intramolecular hemiaminal formation resulting in hemiaminal intermediate 5. A person of ordinary skill in the art will recognize that amine 7, carboxylic acid 8 and hemiaminal intermediate 5 can be diastereomerically pure or racemic.

For disclosed working embodiments, the amide bond formation and hemiaminal formation were performed with any one of amines 52, 54, or 58 and carboxylic acid 16 to form any one of hemiaminals 50, 56, or 60. Particular embodiments concern using EDC, HOBt, and Et$_3$N in dichloromethane to carry out the reactions. The compounds illustrated in Scheme 11 can be made with the particular stereochemistry shown, any combination of diastereomers, or they can be racemic. In particular embodiments, hemiaminal formation resulted in forming a cis-fused ring system.

Scheme 11

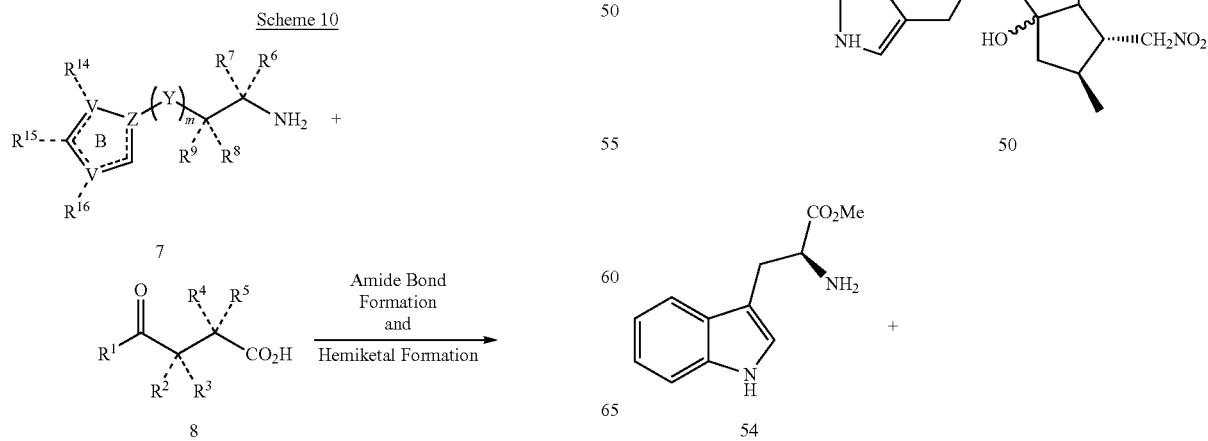

-continued

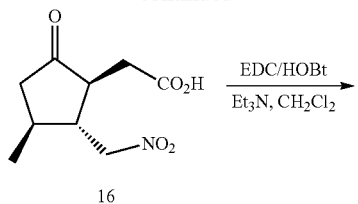
16

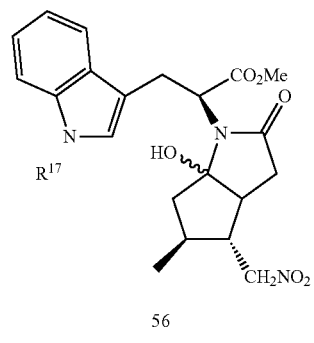
56

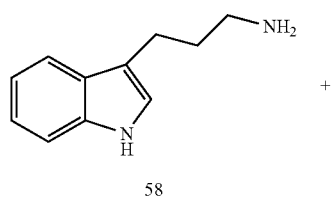
58

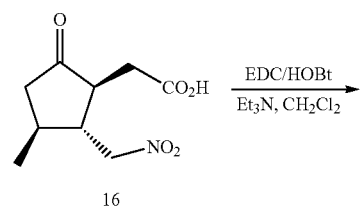
16

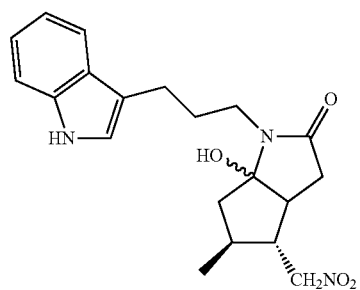
60

Once hemiaminal intermediate 5 is formed, it can be subjected to reaction conditions effective in promoting an acyl iminium cyclization (Scheme 12). Conditions suitable for promoting an acyl iminium cyclization can include using an acid, particularly an organic acid, such as (but not limited to) trifluoroacetic acid (TFA), p-toluenesulfonic acid (p-TsOH), and camphorsulfonic acid (CSA). Treating the hemiaminal with an appropriate acid can form the desired polycyclic alkaloid 3. $R^1$-$R^{16}$, Y, Z, V, W, and m are as previously described.

Scheme 12

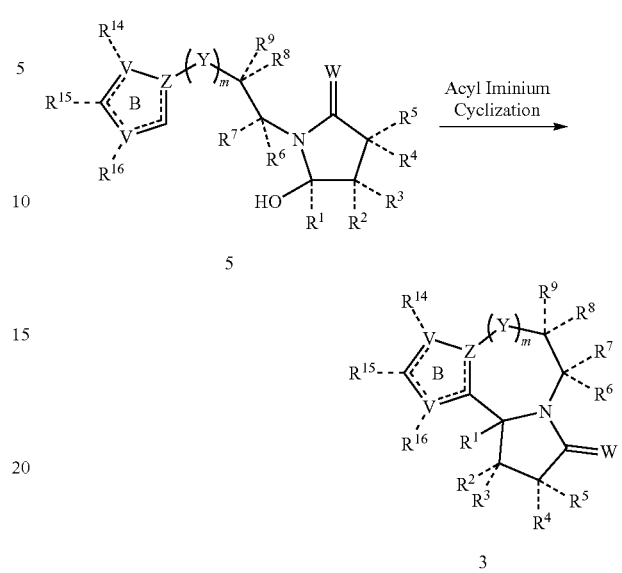

In particular embodiments, the acyl iminium cyclization was carried out using TFA in dichloromethane at room temperature, or p-TsOH in toluene at reflux. Both reagents and reaction conditions converted hemiaminal intermediates 50, 56, or 60 to the respective polycyclic alkaloids, such as 62, 64, and 66. A person of ordinary skill in the art will recognize that the compounds illustrated in Scheme 13 can have the particular stereochemistry shown, any combination of diastereomers, or they can be racemic.

Scheme 13

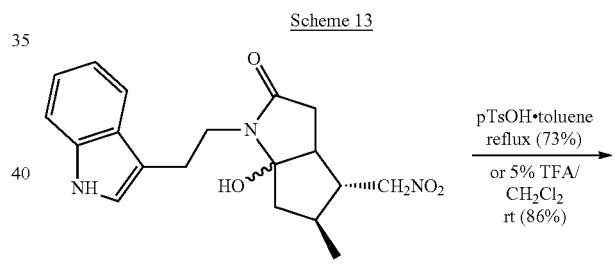
50

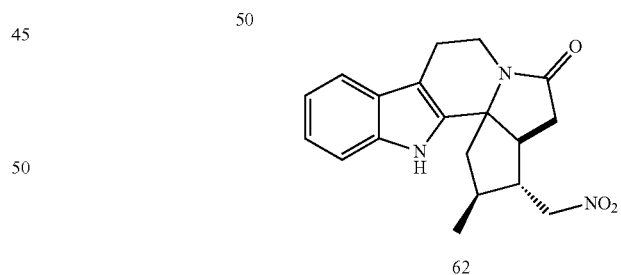
62

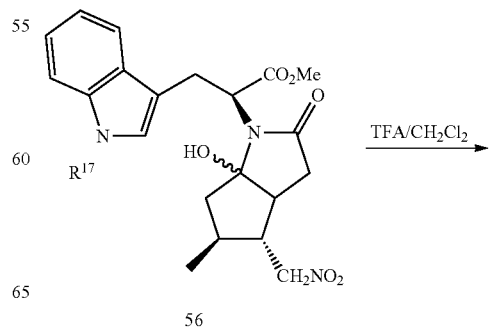
56

V. Further Structural Modifications of Polycyclic Alkaloids

The chemical structures of the disclosed polycyclic alkaloids made according to the exemplary syntheses described above can be further modified to produce additional analogs. Certain embodiments of structurally-modified polycyclic can be made from intermediate 67, as illustrated in Scheme 14. For example, polycyclic alkaloid 67 can be converted to derivative 68, wherein $R^{21}$ has been converted to $R^{22}$. In other embodiments, polycyclic alkaloid 67 can be converted to derivative 70. A person of ordinary skill in the art will recognize that the conditions used to further modify the chemical structures of the polycyclic analogs will depend on the type of transformation that is desired and the identity of the $R^{21}$ substituent. With respect to Scheme 14, $R^1$, $R^2$, $R^3$, $R^4$, $R^5$, $R^6$, $R^7$, $R^8$, $R^9$, $R^{10}$, $R^{11}$, $R^{12}$, $R^{13}$, Y, W, and m are as previously described. $R^{19}$, $R^{20}$, $R^{21}$, $R^{22}$ can be selected from aliphatic, aryl, halogen, a heteroatom-containing moiety, and hydrogen. In particular embodiments, $R^{19}$, $R^{20}$, and $R^{21}$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and $NR^{17}R^{18}$ wherein $R^{17}$ and $R^{18}$ independently are hydrogen, aliphatic, aryl, heteroaliphatic, heteroaryl, and any combination thereof.

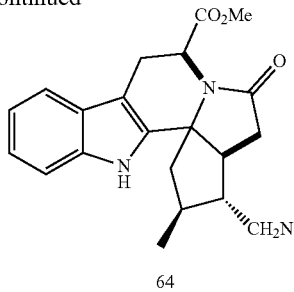

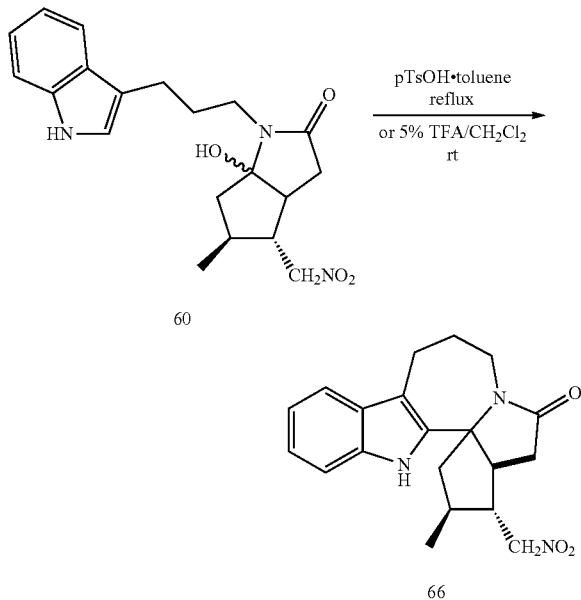

Scheme 14

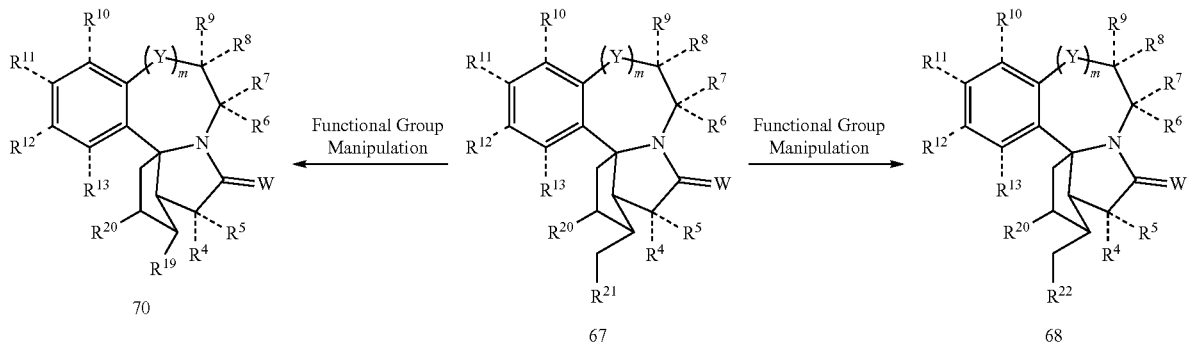

Exemplary examples of particular embodiments are illustrated in Scheme 15.

Scheme 15

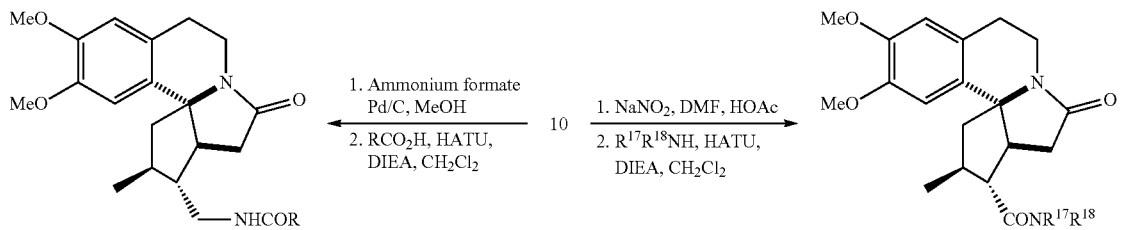

-continued
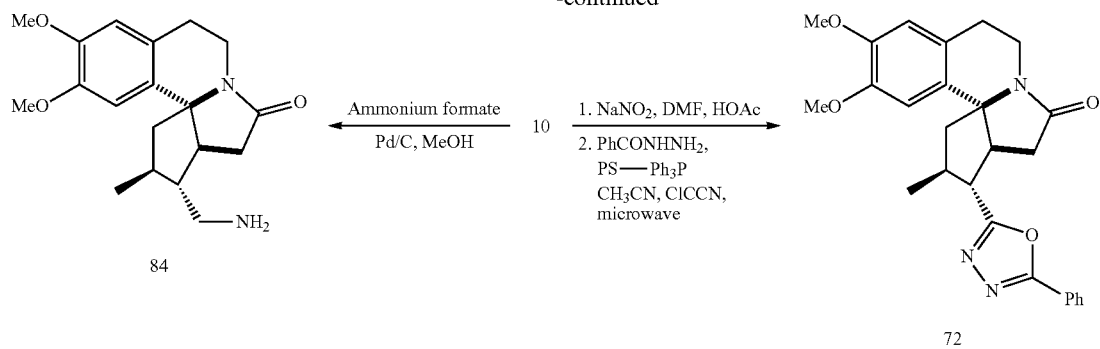
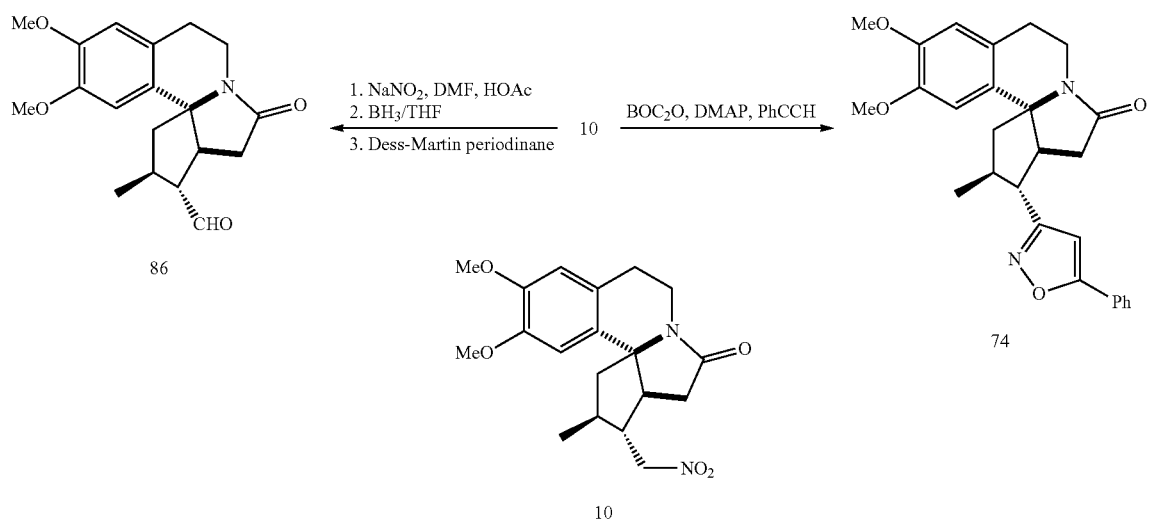
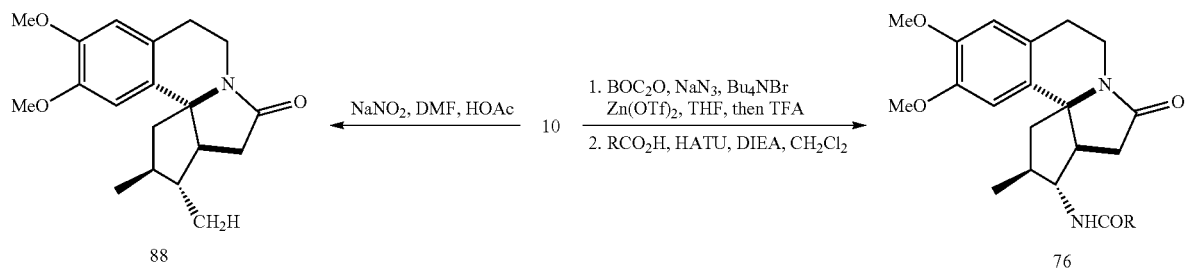
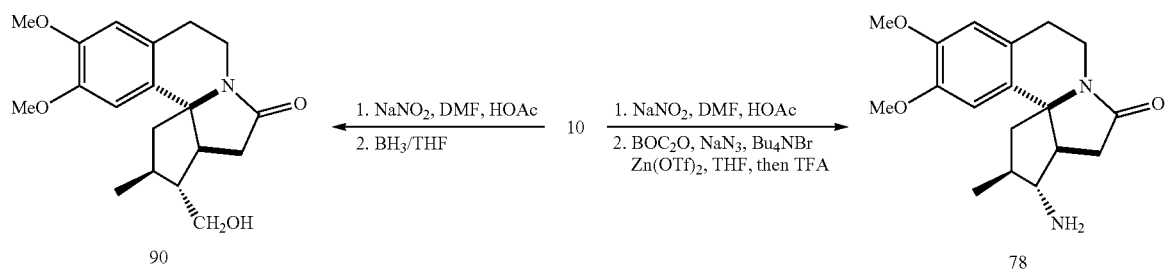

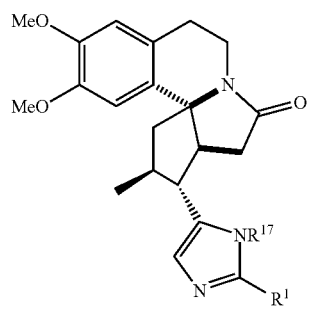

92

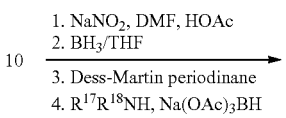

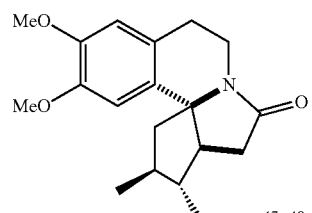

80

With reference to Scheme 15, the nitromethyl group was transformed to make additional analogs. Amine 84 was prepared by catalytic transfer hydrogenation according to the method of Deprez (Deprez-Poulain, R.; et al. *Tetrahedron Lett.* 2004, 45, 5287; Deprez-Poulain, R., et al. *Green Chem.* 2010, 12, 961). The nitromethyl group of 10 was also transformed into carboxylic acid 88 using sodium nitrite in a mixture of dimethylformamide (DMF) and acetic acid (using the method according to Mineno, T.; Miller, M. J. *J. Org. Chem.* 2003, 68, 6591). Acid 88 was reduced to alcohol 90 and then re-oxidized to aldehyde 86 with Dess-Martin periodinane. In addition, acid 88 was transformed using a Curtius rearrangement to yield a Boc-protected amine, followed by conversion to free amine 78 (Leogane, O.; Lebel, H. *Org. Synth.* 2009, 86, 113). Amides were prepared from either acid 88 or free amine 78 under standard conditions, while aldehyde 86 was subjected to reductive amination. The nitromethyl group itself also served as a nitrile oxide precursor, which was then subjected to [3+2] cycloaddition reactions (Basel, Y.; Hassner, A. *Synthesis,* 1997, 309). These newly generated aldehyde and carboxylic acid allow additional analogs to be made. For example, acid 88 was converted to oxadiazole 72 by microwave radiation (Wang, Y., et al. *Tetrahedron Lett.*, 2006, 47, 105) while 10 was converted to isoxazole 74. A person of ordinary skill in the art will recognize that all compounds in Scheme 14 can have the particular stereochemistry illustrated, any combination of diastereomers, or they can be racemic.

Acid 94 was coupled with various amines, as illustrated in Scheme 16. In particular embodiments, these reactions were carried out as previously described with the disclosed coupling reagents. Alkyl-substituted amides (96 and 98), cyclopropyl-substituted amides (100), asymmetric amides (102 and 108), nitrile-containing amides (104), and piperazine-substituted amides (106) were formed using this method.

Scheme 16

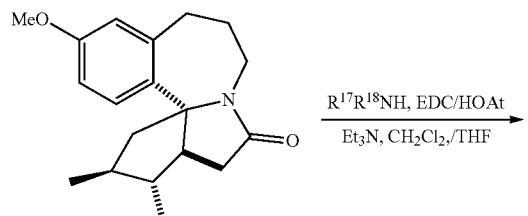

94

-continued

MeO $CONR^{17}R^{18}$

96 $R^{17}$ = H; $R^{18}$ = Me

98 $R^{17}$ = $R^{18}$ = ET

100 $R^{17}$ = H; $R^{18}$ = c-$C_3H_7$

102 $R^{17}$ = H; $R^{18}$ =

104 $R^{17}$ = H; $R^{18}$ = $CH_2CN$

106 $R^{17}$ = H; $R^{18}$ =

108 $R^{17}$ = H; $R^{18}$ =

Other embodiments concern synthesizing polycyclic phenols using, for example, the reaction sequence illustrated in Scheme 17. In these embodiments, the aromatic ring of amine 110 was monosubstituted with a benzyl group at either the meta (114) or para position (112). A person of ordinary skill in the art will recognize that the present method is not limited to only meta- or para-substituted phenyl rings. The previously described coupling reaction and subsequent cyclization were carried out to make a monobenzylated polycyclic compound 112 (or 114). Compound 112 (or 114) was converted to a carboxylic acid (116 and 118, respectively), which was subsequently alkylated, such as by methylation, forming an ester. The benzyl protecting group was then removed by hydrogenation to provide a free phenol. The free phenol was further modified to provide a functionalized compound, such as triflate 126. In particular embodiments, triflate 126 was formed by treating phenol 124 with triflic anhydride ($Tf_2O$).

Scheme 17

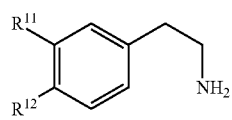
110

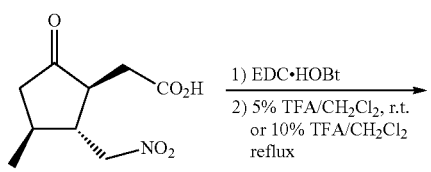
16

1) EDC·HOBt
2) 5% TFA/CH$_2$Cl$_2$, r.t.
or 10% TFA/CH$_2$Cl$_2$
reflux

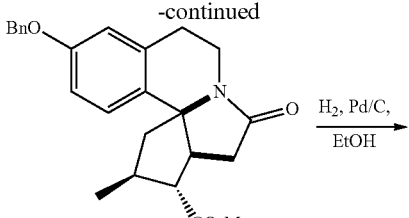
120

H$_2$, Pd/C,
EtOH

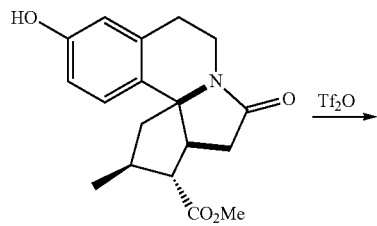
124

Tf$_2$O

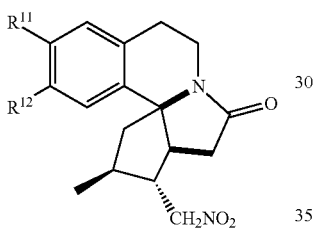

112 R$^{11}$ = H, R$^{12}$ = OBn (55%)
114 R$^{11}$ = OBn, R$^{12}$ = H (43%)

NaNO$_2$, HOAc
DMF,
50 degrees C.

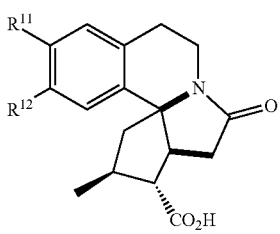

116 R$^{11}$ = H, R$^{12}$ = OBn
118 R$^{11}$ = OBn, R$^{12}$ = H

118 TMS-diazomethane →

126

Particular embodiments concern polycyclic alkaloids comprising a fused five-membered ring B having the general formula illustrated in Scheme 18. In particular embodiments, polycyclic alkaloid 128 can be converted to derivative 130, wherein R$^{21}$ has been converted to R$^{22}$. In other embodiments, polycyclic alkaloid 128 can be converted to derivative 132. A person of ordinary skill in the art will recognize that the conditions used for with these functional group manipulations will depend on the type of transformation that is desired and the identity of the R$^{21}$ substituent. R$^4$, R$^5$, R$^6$, R$^8$, R$^{14}$, R$^{15}$, R$^{16}$, V, W, and m are as previously described. R$^{19}$, R$^{20}$, R$^{21}$, R$^{22}$ can be selected from aliphatic, aryl, halogen, a heteroatom-containing moiety, and hydrogen. In particular embodiments, R$^{19}$, R$^{20}$, and R$^{21}$ independently are selected from alkane, alkene, alkyne, benzyl, phenyl, bromo, chloro, fluoro, iodo, aldehyde, acyl halide, carbonate, carboxyl, carboxylate, ether, ester, hydroxyl, ketone, silyl ether, peroxy, hydroperoxy, phosphate, phosphoryl, phosphodiester, phosphine, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amide, azide, azo, cyano, isocyanate, imide, nitrile, isonitrile, nitro, nitroso, nitromethyl, and NR$^{17}$R$^{18}$ wherein R$^{17}$ and R$^{18}$ independently are hydrogen, aliphatic, aryl, heteroaliphatic, heteroaryl, and any combination thereof.

Scheme 18

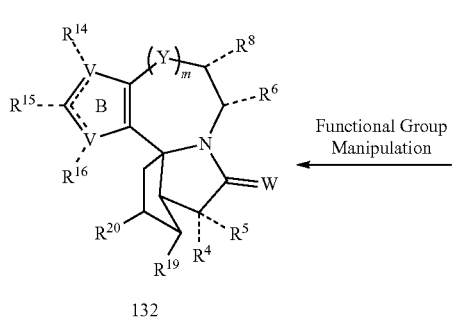
132

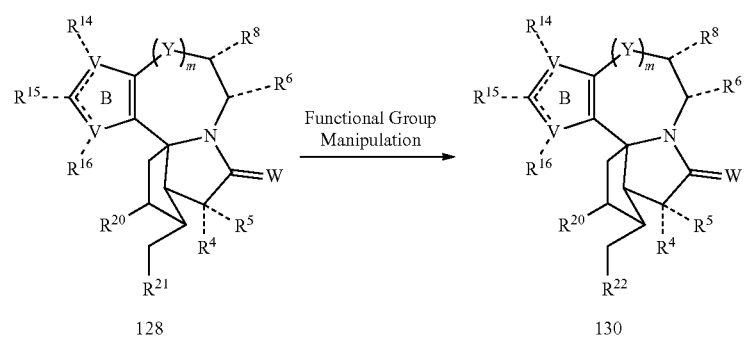
128    130

In particular embodiments, polycyclic alkaloids comprising a benzopyrrole can undergo functional group manipulation. For example, Scheme 19 illustrates converting the nitromethyl moiety of polycyclic alkaloid 134 to carboxylic acid 136 using sodium nitrite in acetic acid and dimethylformamide. The pyrrole protecting group was removed subsequently by treating acid 136 with cesium carbonate in methanol and tetrahydrofuran, to make polycyclic alkaloid 138. A further embodiment is illustrated in Scheme 20 wherein similar transformations are performed. As indicated herein, the compounds illustrated in Schemes 19 and 20 may have the particular stereochemistry shown, any combination of diastereomers, or they can be racemic.

VI. Biological Applications

*Erythrina* alkaloids and their homologues, such as Schelhammerane, B-Homoerythrinane, A-Norerythrinane, and A-Norschelhammerane are biologically active compounds. The disclosed compounds, therefore, can exhibit a similar variety of pharmacological activities. These pharmacological activities include, but are not limited to, curare-like, sedative, hypotensive, or central nervous system depressant properties. These compounds may be antagonists of the nicotinic acetylcholine receptor (nACh-R), which is involved in neuronal excitation of skeletal muscle. The planar disposition of dis-

Scheme 19

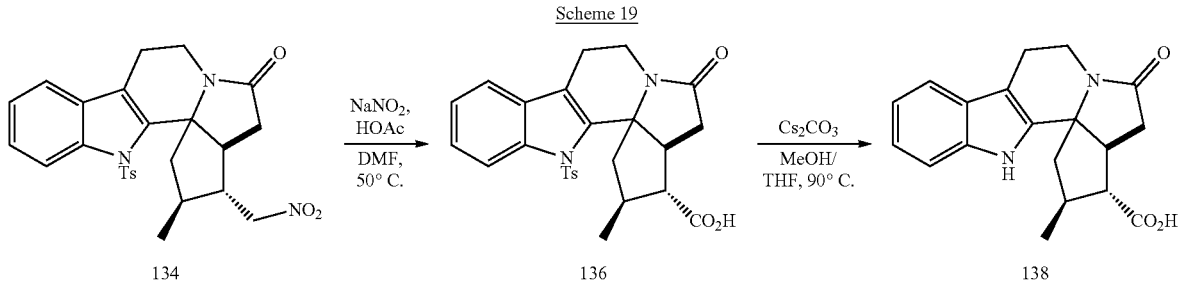

134    136    138

Scheme 20

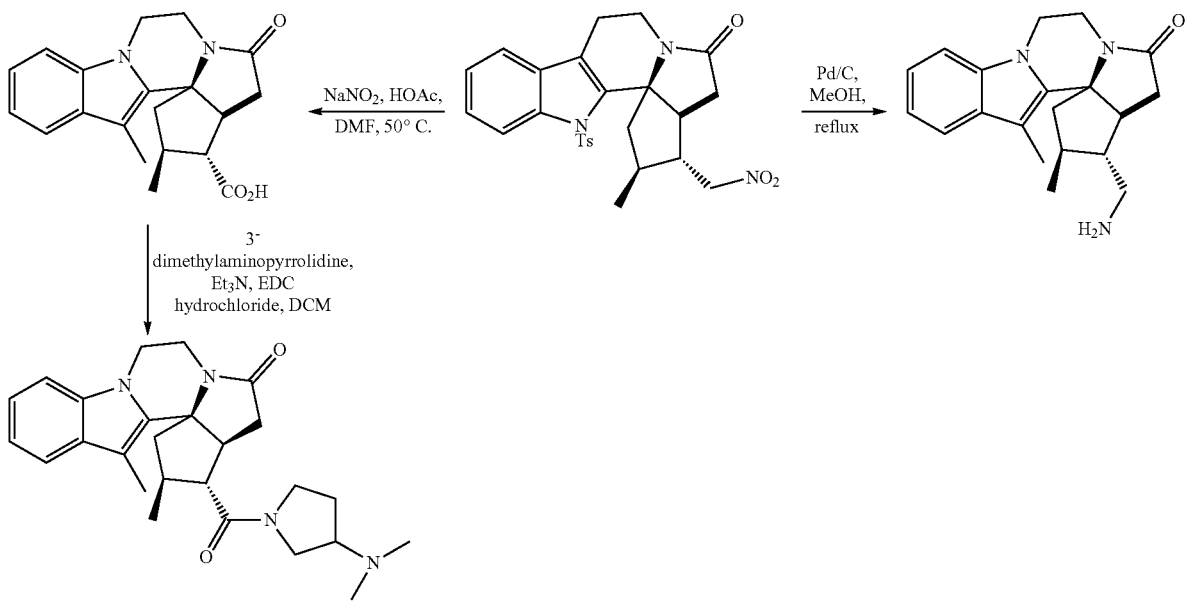

closed compounds also allows intercalation between base pairs of DNA. In addition, these compounds may be protein kinase inhibitors. In particular disclosed embodiments, the compounds may be used as TGR5 agonists, TGR5 antagonists, bile acid receptor modulators, and/or G-protein coupled receptor ligands. The compounds disclosed herein are capable of acting as TGR5 agonists, TGR5 antagonists, thereby modulating TGR5, which is involved in several biological processes within the body, including energy and/or glucose homeostasis, neurotransmission and inflammatory signaling. Exemplary disclosed compounds are effective TGR5 agonists and may be used to treat lipid and glucose disorders.

Embodiments of the compound disclosed herein may be used to treat and/or prevent diseases/disorders associated with bile acid receptor activity. In particular disclosed embodiments, the compound improves insulin sensitivity, reduces hepatosteatosis, lowers hepatic lipids, LDL-C, TG levels, and serum cholesterol, and also may increase energy expenditure. As such, the presently disclosed compound is useful for treating type II diabetes. Further, the compound, as a bile acid receptor modulator, can be used to treat and/or prevent one or more of the following disorders/diseases: cholelithiasis, cholestatic liver disease, cholestatic pruritus, cerebrotendinous xanthomatosis, primary biliary cirrhosis, non-alcoholic fatty liver disease, hypertriglyceridaemia, hypercholesterolaemia, various cancers (e.g., skin, lung, colon), metabolic diseases, and 3b-hydroxysteroid oxido-reductase deficiency. The compound also modulates neurotransmission and/or sensation, and thus have utility as analgesics or antipruritics.

Embodiments of the compound disclosed herein can be used to treat an intestinal motility disorder. An intestinal motility disorder, as referred to herein, concerns diseases and/or disorders of the upper intestinal tract, the lower intestinal tract, and combinations thereof. TGR5 deficiency leads to a loss of intestinal motility causing, for example, constipation. In particular disclosed embodiments, the present compound can be used to treat an intestinal motility disorder such as diverticulosis (small-intestinal diverticula, colonic diverticula, diverticulitis, painful diverticular disease without diverticulitis, and hemorrhage from diverticula); megacolon (e.g., aganglionic megacolon, chronic idiopathic megacolon, and acquired megacolon); intestinal pseudoobstruction (e.g., chronic or intermittent secondary pseudoobstruction, idiopathic intestinal pseudoobstruction, and acute intestinal pseudoobstruction); constipation; dyspepsia; gastroparesis; irritable bowel syndrome; and combinations thereof.

In addition to the disorders above, the present compounds include TGR5 receptor agonists, which reduce IL-1α, IL-1β, IL-6, IL-8 and/or TNFα signaling and consequently are useful as anti-inflammatory agents.

VII. Pharmaceutical Compositions

Embodiments of the disclosed polycyclic alkaloids may be used in in vitro, in vivo and/or ex vivo contexts as a sedative, for treating hypotension, and otherwise interacting with the central nervous system. The disclosed compounds may also be used in a pharmaceutical composition for activating and/or modulating a TGR5 receptor, a bile acid receptor, and/or a G-protein coupled receptor. In particular disclosed embodiments, the disclosed pharmaceutical composition may be used to treat an intestinal motility disorder, such as diseases and/or disorders of the upper intestinal tract, the lower intestinal tract, and combinations thereof. In particular disclosed embodiments, the intestinal motility disorder may be selected from diverticulosis (small-intestinal diverticula, colonic diverticula, diverticulitis, painful diverticular disease without diverticulitis, and hemorrhage from diverticula); megacolon (e.g., aganglionic megacolon, chronic idiopathic megacolon, and acquired megacolon); intestinal pseudoobstruction (e.g., chronic or intermittent secondary pseudoobstruction, idiopathic intestinal pseudoobstruction, and acute intestinal pseudoobstruction); constipation; dyspepsia; gastroparesis; irritable bowel syndrome; and combinations thereof.

The polycyclic alkaloids may be administered singly, as mixtures of one or more polycyclic alkaloids or in a mixture or combination with other agents useful for treating a particular condition and/or the symptoms associated with such conditions. The polycyclic alkaloids may also be administered in mixture or in combination with agents useful to treat other disorders or maladies. In some embodiments, the polycyclic alkaloids are administered as pharmaceutical compositions.

In particular disclosed embodiments, the amount of the polycyclic alkaloid present in the composition can range from greater than zero to about 99% of the pharmaceutical composition, more typically from about 1% to about 90%, even more typically from about 10% to about 90%.

Pharmaceutical compositions comprising embodiments of the disclosed polycyclic alkaloids may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the polycyclic alkaloids into preparations which can be used pharmaceutically.

The polycyclic alkaloids may be used to form a pharmaceutical composition. The pharmaceutical composition may comprise the polycyclic alkaloid itself. Alternatively, the polycyclic alkaloid may be a prodrug, hydrate, a solvate, a pharmaceutically acceptable salt, or combinations thereof. Typically, pharmaceutically acceptable salts are more soluble in aqueous solutions than the corresponding free acids and bases from which the salts are produced; however, salts having lower solubility than the corresponding free acids and bases from which the salts are produced may also be formed. Pharmaceutically acceptable salts are typically counterbalanced with an inorganic base, organic base, or basic amino acid if the salts are positively charged; or the salt is counterbalanced with an inorganic acid, organic acid, or acidic amino acid if they are negatively charged. Pharmaceutically acceptable salts can also be zwitterionic in form. Salts can be formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. Other elements capable of forming salts are well-known to those skilled in the art, e.g. all elements from the main groups I to V of the Periodic Table of the Elements, as well as the elements from the subgroups I to VIII. Any chemical compound recited in this specification may alternatively be administered as a pharmaceutically acceptable salt thereof. "Pharmaceutically acceptable salts" are also inclusive of the free acid or base. Descriptions of suitable pharmaceutically acceptable salts can be found in *Handbook of Pharmaceutical Salts, Properties, Selection and Use*, Wiley VCH (2002), which is incorporated herein by reference.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the polycyclic alkaloid(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the polycyclic alkaloid(s) in aqueous or oily vehicles. The compositions may also contain formulating agents, such as suspending, stabilizing and/or dispersing agents. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen-free water, buffer, dextrose solution, etc., before use. To this end, the polycyclic alkaloid(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the polycyclic alkaloid, as is well known.

For buccal administration, the compositions may take the form of tablets or lozenges formulated in conventional manner.

For rectal and vaginal routes of administration, the polycyclic alkaloid(s) may be formulated as solutions (for retention enemas) suppositories or ointments containing conventional suppository bases such as cocoa butter or other glycerides.

For nasal administration or administration by inhalation or insufflation, the polycyclic alkaloid(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the polycyclic alkaloid and a suitable powder base such as lactose or starch.

For ocular administration, the polycyclic alkaloid(s) may be formulated as a solution, emulsion, suspension, etc. suitable for administration to the eye. A variety of vehicles suitable for administering polycyclic alkaloid to the eye are known in the art. Specific non-limiting examples of suitable formulations for administration to the eye are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the polycyclic alkaloid(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the polycyclic alkaloid(s) for percutaneous absorption may be used. To this end, permeation enhancers may be used to facilitate transdermal penetration of the polycyclic alkaloid(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver polycyclic alkaloid(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the polycyclic alkaloid(s). The pack may, for example, comprise metal or plastic foil, such as a blister pack. The pack or dispenser device may be accompanied by instructions for administration.

VIII. Effective Dosages

Embodiments of the disclosed polycyclic alkaloid(s), or compositions thereof, will generally be used in an amount effective to achieve the intended result, for example in an amount effective to treat or prevent the particular condition being treated. The polycyclic alkaloid(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a polycyclic alkaloid to a patient suffering from hypotension provides therapeutic benefit not only when the hypotension is ameliorated, but also when the patient reports a decrease in the severity or duration of the symptoms associated with the hypotension.

For prophylactic administration, the polycyclic alkaloid may be administered to a patient at risk of developing hypotension, a central nervous system condition, or a disease/disorder associated with TGR5 receptors, bile acid receptors, and/or G-protein coupled receptors. For example, the polycyclic alkaloid may be administered prior to surgery to avoid or ameliorate hypotension or a central nervous system condition. Polycyclic alkaloids may also be administered prophylactically to at-risk individuals to prevent the onset of the hypotension or a central nervous system condition.

The amount of polycyclic alkaloid administered will depend upon a variety of factors, including, for example, the particular indication being treated, the mode of administration, whether the desired benefit is prophylactic or therapeutic, the severity of the indication being treated and the age and weight of the patient, the bioavailability of the particular polycyclic alkaloid, etc. Determination of an effective dosage is well within the capabilities of those skilled in the art.

Effective dosages may be estimated initially from in vitro assays. For example, an initial dosage for use in animals may be formulated to achieve a circulating blood or serum concentration of polycyclic alkaloid that is at or above an $IC_{50}$ of the particular polycyclic alkaloid as measured in an in vitro assay. Calculating dosages to achieve such circulating blood or serum concentrations taking into account the bioavailability of the particular polycyclic alkaloid is well within the capabilities of skilled artisans. For guidance, the reader is referred to Fingl & Woodbury, "General Principles," In: Goodman and Gilman's The Pharmaceutical Basis of Therapeutics, Chapter 1, latest edition, Pagamonon Press, and the references cited therein.

Initial dosages can also be estimated from in vivo data, such as animal models. Animal models useful for testing the efficacy of polycyclic alkaloid to treat or prevent the various conditions described above are well-known in the art. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but may be higher or lower, depending upon, among other factors, the activity of the polycyclic alkaloid, its bioavailability, the mode of administration and various factors discussed above. Dosage amount and interval may be adjusted individually to provide plasma levels of the polycyclic alkaloid(s) which are sufficient to maintain therapeutic or prophylactic effect. For example, the polycyclic alkaloids may be administered once per week, several times per week (e.g., every other day), once per day, or multiple times per day, depending upon, among other things, the mode of administration, the specific indication being treated and the judgment of the prescribing physician.

Preferably, the polycyclic alkaloid(s) will provide therapeutic or prophylactic benefit without causing substantial toxicity. Toxicity of the polycyclic alkaloid(s) may be determined using standard pharmaceutical procedures. The dose ratio between toxic and therapeutic (or prophylactic) effect is the therapeutic index. Polycyclic alkaloid(s) that exhibit high therapeutic indices are preferred.

IX. Working Examples

General Experimental Procedures

NMR was performed on a Varian Mercury 300 MHz NMR. Chemical shifts were referenced to solvents. Assignments were based on chemical shifts, COSY experiments or DEPT experiments for $^{13}C$, and in some cases are tentative. Flash chromatography used J. T. Baker Silica Gel, 60-200 mesh. Radial chromatography was performed on a chromatotron (Harrison Research, Model 7924T). HPLC used a Waters 2695 Separation module equipped with a Micromass ZQ mass spectrometer operating in the electrospray mode. High resolution mass spectra were obtained on a Waters Acquity system using method A. HPLC methods: (A) Column: Kinetex C-18, 2.6 μm, 2.1×50 mm, flow rate 0.73 mL/min, gradient 95% $H_2O$ containing 0.05% $HCO_2H$/5% $CH_3CN$ to 100% $CH_3CN$ in 3 min.; (B) Phenomenex C-18 column, 3×100 mm, 5 μm. Flow rate 1.5 mL/min. Gradient containing 95% $H_2O$ with 0.05% $HCO_2H$/5% $CH_3CN$ to 100% $CH_3CN$ in 10 min. Purity was assessed by UV absorption at 254 nm or qualitatively by evaporative light scattering (ELSD). Preparative HPLC was performed on a Waters C-18 mass directed purification system. Microwave experiments were performed with a CEM Explorer microwave in closed vials with a constant temperature as indicated and a maximum power of 300 watts. Optical rotations were performed on a Rudolph Autopol IV polarimiter. Chemical names and atom numbering for compounds 88, 147, 38, 138 and 66 were provided by the Chemical Abstracts Service and the other compounds were named by analogy.

Characterization of Compounds

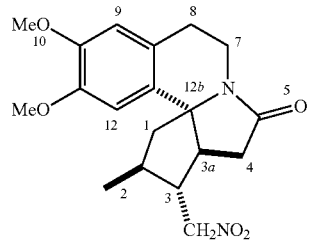

10

Cyclopenta[2,3]pyrrolo[2,1-a]isoquinoline-3-nitromethyl, 1,2,3,3a,4,5,7,8-octahydro-10,11-dimethoxy-2-methyl-5-oxo-(2S,3R,3aS,12bR)

A mixture of [1S-(1β,2α,3β)]-(+)-3-methyl-2-(nitromethyl)-5-oxocyclopentane acetic acid (Aldrich, Cat. #647497) (16) (13 g, 60 mmol), 3,4-dimethoxyphenethylamine (12.2 g, 67 mmol), N-(3-dimethylaminopropyl)-N'-ethylcarbodiimide hydrochloride (EDC) (13 g, 68 mmol), 1-Hydroxybenzotriazole hydrate (HOBt) (9 g, 67 mmol) and triethylamine (20 mL, 2.4 equiv.) were dissolved in dichloromethane (200 mL) and stirred overnight at room temperature (r.t.). The reaction mixture was washed with water, 10% hydrochloric acid (HCl) and sat. aq. sodium bicarbonate ($NaHCO_3$) solution, then dried over anhydrous sodium sulfate ($Na_2SO_4$) and concentrated under reduced pressure. The residue was stirred with 5% TFA in dichloromethane (100 mL) at r.t. for 5 h. The reaction mixture was concentrated under reduced pressure. The residue was dissolved in dichloromethane, washed with water and sat. aq. $NaHCO_3$ solution, dried with anhydrous sodium sulfate and concentrated under reduced pressure. The crude product was purified by flash column chromatography on silica gel, eluting with 2% methanol in dichloromethane to yield 10, 12.2 g (56%).

HPLC—(Method A) $t_r$=1.63 min. (Method B) $t_r$=5.92 min. (93%)

[α]$_D^{22}$=+140 (c=1.05, CHCl$_3$)

$^1$H-NMR (300 MHz, CDCl$_3$): δ=6.55 (s, 1H), 6.52 (s, 1H), 4.60-4.68 (m, 2H, CH$_2$NO$_2$,), 4.20-4.27 (m, 1H, H-7b), 3.86 (s, 3H, OMe), 3.82 (s, 3H, OMe), 3.07-3.13 (m, 1H, H-7a or H-8b), 2.95-3.02 (m, 1H, H-8b or H-7a), 2.87-2.91 (m, 1H, H-3a), 2.55-2.65 (m, 2H, H-8a and H-4b), 2.28-2.35 (m, 3H, H-4a, H-1b, and H-2), 2.01-2.07 (m, 1H, H-3), 1.74-1.81 (m, 1H, H-1a), 1.10 (d, J=5.9 Hz, 3H, 2-CH$_3$). $^{13}$C-NMR (75 MHz, CDCl$_3$): δ=171.9 (CO), 148.1 (C), 148.0 (C), 133.6 (C), 125.1 (C), 111.7 (CH), 107.0 (CH), 76.5 (CH$_2$NO$_2$), 70.3 (C-12b), 56.2 (OMe), 55.9 (OMe), 52.9 (CH), 51.5 (CH$_2$), 47.2 (CH), 37.7 (CH), 36.2 (CH$_2$), 35.9 (CH$_2$), 27.0 (CH$_2$), 17.5 (2-CH$_3$). MS (ES): C$_{19}$H$_{24}$N$_2$O$_5$. Calc.: 361.1764 [M+H]$^+$. Found: 361.1773 [M+H]$^+$.

84

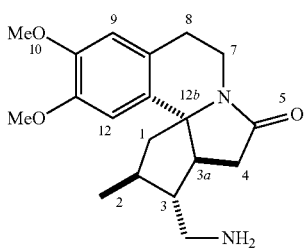

Cyclopenta[2,3]pyrrolo[2,1-a]isoquinoline-3-aminomethyl, 1,2,3,3a,4,5,7,8-octahydro-10,11-dimethoxy-2-methyl-5-oxo-(2S,3R,3aS,12bR)

Compound 10 (5.18 g, 14.4 mmol) was dissolved in methanol (200 mL) and treated with ammonium formate (7.0 g, 0.11 mol) and 10% Pd/C (9.2 g, wet, Degussa type E101 NE/W, Aldrich Cat. #330108). The mixture was heated at 80° C. until HPLC analysis showed complete consumption of the starting material (approx. 5 h). The mixture was filtered hot over Celite and the cake was washed with hot methanol. The filtrate was concentrated under reduced pressure. The residue was dissolved in a mixture of ethyl acetate (EtOAc) and methanol (MeOH) and washed with a small portion of sat. aq. sodium chloride (NaCl). The organic layer was dried over anhydrous sodium sulfate and concentrated under reduced pressure. The residue was dissolved in anhydrous MeOH and cooled on an ice bath. HCl (g) was bubbled in, followed by addition of dry Et$_2$O. Filtration and drying under vacuum gave 84 (HCl salt) as a white solid, 2.77 g (58%). HPLC-(Method B)—t$_r$=2.13 min (95%).

For analytical purposes the hydrochloride salt (2.6 g) was converted to the free base by partitioning between dichloromethane and sat. aq. K$_2$CO$_3$. Y=2.2 g. HPLC—(Method B)—t$_r$=2.13 min. (100%). (Method A)—t$_r$=1.00 min. $^1$H-NMR (300 MHz, CDCl$_3$): δ=6.67 (s, 1H), 6.45 (s, 1H), 4.09-4.17 (m, 1H, H-7b), 3.76 (s, 3H, OMe), 3.73 (s, 3H, OMe), 2.93-3.07 (m, 1H), 2.79-2.95 (m, 3H), 2.66-2.70 (m, 1H), 2.54-2.66 (m, 2H), 2.16-2.28 (m, 2H), 2.00-2.06 (m, 1H), 1.57-1.66 (m, 1H), 1.35-1.40 (m, 1H), 0.94 (d, J=6.1 Hz, 3H, 2-CH$_3$). $^{13}$C-NMR (75 MHz, CDCl$_3$): δ=172.6 (CO), 147.7 (2C), 135.0 (C), 125.0 (C), 111.5 (CH), 107.6 (CH), 70.7 (C-12b), 57.4 (CH), 56.1 (OMe), 55.8 (OMe), 52.0 (CH$_2$), 47.3 (CH), 42.6 (CH$_2$), 37.5 (CH$_2$), 36.9 (CH), 35.8 (CH$_2$), 27.1 (CH$_2$), 18.1 (2-CH$_3$). MS (ES): C$_{19}$H$_{26}$N$_2$O$_3$. Calc.: 331.2022 [M+H]$^+$. Found: 331.2016 [M+H]$^+$.

88

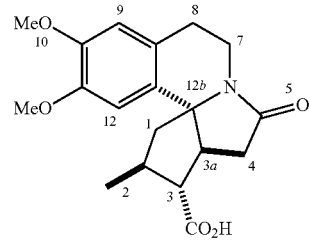

Cyclopenta[2,3]pyrrolo[2,1-a]isoquinoline-3-carboxylic acid, 1,2,3,3a,4,5,7,8-octahydro-10,11-dimethoxy-2-methyl-5-oxo-(2S,3R,3aS,12bR)

Compound 10 (12 g, 33.3 mmol) was dissolved in DMF (120 mL) and treated with NaNO$_2$ (14.9 g, 0.216 mol) and HOAc (40 g, 0.655 mol). The reaction mixture was heated at 50° C. for 7 h. The reaction mixture was poured onto ice and carefully neutralized with solid NaHCO$_3$. The mixture was extracted with Et$_2$O (discarded) and then acidified with concentrated HCl. The aqueous layer was extracted twice with EtOAc. The combined organic layers were dried over anhydrous sodium sulfate and concentrated under reduced pressure (finishing with high vacuum to remove DMF). The residue was re-dissolved in EtOAc and extracted 10 times with sat. aq. NaCl solution (necessary to completely remove residual HOAc). The organic layer was dried over anhydrous sodium sulfate and concentrated under reduced pressure to give 88 as an orange solid, 5.57 g (48%) sufficiently pure for further use. HPLC—(Method B)—t$_r$=4.12 min. (90%). An analytical sample was prepared by hplc—t$_r$=1.55 (Method A). $^1$H-NMR (300 MHz, CDCl$_3$): δ=6.87 (s, 1H), 6.55 (s, 1H), 4.21-4.28 (m, 1H, H-7b), 3.87 (s, 3H, OMe), 3.83 (s, 3H, OMe), 3.12-3.24 (m, 2H, H-7a and H-3a), 2.93-3.05 (m, 1H, H-8b), 2.58-2.70 (m, 3H, H-8a, H-4b, and H-2), 2.39-2.51 (m, 2H, H-3 and H-4a), 2.27-2.34 (dd, J=13.0, 7.0 Hz, 1H, H-1b), 1.80 (t, J=11.4 Hz, 1H, H-1a), 1.16 (d, J=6.4 Hz, 2-CH$_3$). $^{13}$C-NMR (75 MHz, CDCl$_3$): δ=177.4 (CO), 172.6 (CO), 148.5 (C), 148.4 (C), 133.8 (C), 125.3 (C), 112.3 (CH), 108.3 (CH), 71.8 (C-12b), 59.4 (CH), 56.3 (OMe), 56.0 (OMe), 51.3 (CH$_2$), 48.1 (CH), 39.2 (CH), 37.1 (CH$_2$), 36.2 (CH$_2$), 27.0 (CH$_2$), 18.4 (2-CH$_3$). MS (ES): C$_{19}$H$_{23}$NO$_5$. Calc.: 346.1654 [M+H]$^+$. Found: 346.1662 [M+H]$^+$.

90

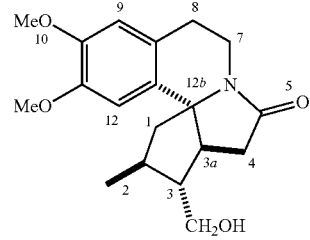

Cyclopenta[2,3]pyrrolo[2,1-a]isoquinoline-3-hydroxymethyl, 1,2,3,3a,4,5,7,8-octahydro-10,11-dimethoxy-2-methyl-5-oxo-(2S,3R,3aS,12bR)

Compound 88 (3.0 g, 8.7 mmol) was dissolved in dry THF (60 mL) and treated with 9.0 mL of 1M borane/THF at r.t. for 1.5 h. The reaction mixture was treated with 10% HCl and then extracted 3 times with a mixture of EtOAc and MeOH. The organic layer was dried over anhydrous sodium sulfate and concentrated under reduced pressure. The crude product was purified by flash chromatography on silica gel, eluting with 5% MeOH in dichloromethane to give 90, 2.26 g (79%) as a white foam. HPLC—(Method B)—$t_r$=4.11 min (95%). An analytical sample was prepared by hplc—$t_r$=1.31 min (Method A)

$[\alpha]_D^{24}$=+132.6 (c=0.91, CHCl$_3$)

$^1$H-NMR (300 MHz, DMSO-d$_6$): δ=6.79 (s, 1H), 6.61 (s, 1H), 3.74-3.98 (m, 1H, H-7b), 3.70 (s, 3H, OMe), 3.68 (s, 3H, OMe), 3.55-3.62 (m, 2H, C$\underline{H}_2$OH), 3.00-3.15 (m, 1H, H-7a), 2.70-2.77 (m, 2H, H-8b and H-3a), 2.51-2.60 (m, 1H, H-8a), 2.33-2.43 (m, 1H, H-4b), 2.12-2.25 (m, 2H, H-4a and H-2), 2.02-2.16 (m, 1H, H-1b), 1.59-1.66 (t, J=12.1 Hz, 1H, H-1a), 1.35-1.42 (m, 1H, H-3), 0.95 (d, J=6.3 Hz, 3H, 2-CH$_3$). $^{13}$C-NMR (75 MHz, DMSO-d$_6$): δ=172.5 (CO), 148.1 (2C), 135.7 (C), 125.4 (C), 112.7 (CH), 108.7 (CH), 70.6 (C-12b), 60.8 (CH$_2$), 57.7 (CH), 56.3 (OMe), 56.1 (OMe), 52.5 (CH$_2$), 46.6 (CH), 39.4 (CH$_2$), 37.5 (CH$_2$), 36.0 (CH), 27.2 (CH$_2$), 18.8 (2-CH$_3$). MS (ES): C$_{19}$H$_{25}$NO$_4$. Calc.: 332.1862 [M+H]$^+$. Found: 332.1877 [M+H]$^+$.

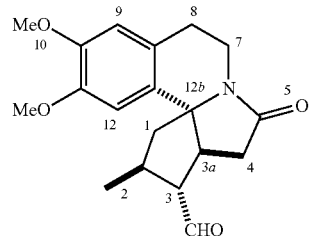

86

Cyclopenta[2,3]pyrrolo[2,1-a]isoquinoline-3-formyl-1,2,3,3a,4,5,7,8-octahydro-10,11-dimethoxy-2-methyl-5-oxo-(2S,3R,3aS,12bR)

Compound 90 (0.43 g, 1.3 mmol) was dissolved in dry dichloromethane (15 mL) and treated with NaHCO$_3$ (130 mg, 1.2 equiv.) and Dess-Martin periodinane (0.66 g, 1.2 equiv., Alfa-Aesar). After 3 h the reaction was quenched with 1M aqueous sodium thiosulfate and sat. aq. NaHCO$_3$, then extracted twice with Et$_2$O. The organic layer was dried over anhydrous sodium sulfate and concentrated under reduced pressure. The crude product was purified by radial chromatography on silica gel, eluting with 2% MeOH in dichloromethane to give 86 as a white foam, 0.19 g (44%). HPLC—(Method B)—$t_r$=4.41 min (97%). $^1$H-NMR (300 MHz, CDCl$_3$): δ=9.85 (s, 1H, CHO), 6.66 (s, 1H), 6.49 (s, 1H), 4.15-4.22 (m, 1H, H-7b), 3.82 (s, 3H, OMe), 3.80 (s, 3H, OMe), 3.10-3.20 (m, 1H), 3.04-3.08 (m, 1H), 2.88-2.98 (m, 1H), 2.49-2.66 (m, 4H), 2.22-2.28 (dd, J=17.7, 2.1 Hz, 1H), 2.13-2.20 (dd, J=13.4, 7.2 Hz, 1H), 1.78-1.87 (dd, J=13.4, 9.2 Hz, 1H), 1.14 (d, J=6.0 Hz, 3H, 2-CH$_3$). $^{13}$C-NMR (75 MHz, CDCl$_3$): δ=202.0, (CHO), 172.5 (CO), 148.3, 148.2, 133.4, 125.6, 111.8, 107.7, 72.3, 67.2, 56.4, 56.1, 50.6, 44.3, 37.5, 37.1, 36.3, 27.2, 19.4. MS (ES): C$_{19}$H$_{23}$NO$_4$. Calc.: 330.1705 [M+H]$^+$. Found: 330.1704 [M+H]$^+$.

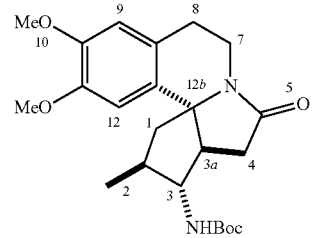

140

Cyclopenta[2,3]pyrrolo[2,1-a]isoquinoline-3-(N-t-butoxycarbonyl)amino-1,2,3,3a,4,5,7,8-octahydro-10,11-dimethoxy-2-methyl-5-oxo-(2S,3R,3aS,12bR)

Compound 88 (3.05 g, 8.8 mmol) was dissolved in dry THF (100 mL) and treated with Bu$_4$NBr (0.6 g, 1.86 mmol), NaN$_3$ (2.2 g, 33.8 mmol), di-t-butyldicarbonate (2.5 g, 11.4 mmol) and Zn(OTf)$_2$ (110 mg, 0.30 mmol) and then heated at 45° C. for 23 h. The reaction mixture was cooled to r.t. and a solution of NaNO$_2$ (8 g, 119 mmol) in water (75 mL) was added. After stirring 1 h the reaction mixture was extracted twice with EtOAc. The organic layers were washed twice with sat. aq. NH$_4$Cl, once with sat. aq. NaHCO$_3$, then dried over anhydrous sodium sulfate and concentrated under reduced pressure. The crude product was passed over a pad of silica gel, eluting with 5% MeOH in dichloromethane to give 140, 2.50 g (68%), sufficiently pure for deprotection. An analytical sample was prepared by hplc. HPLC—(Method A)—$t_r$=1.81 min. $^1$H-NMR (300 MHz, CDCl$_3$, 60° C.): δ=6.83 (s, 1H), 6.51 (s, 1H), 4.81 (m, 1H, NH), 4.17-4.24 (m, 1H, H-7b), 3.27-3.37 (m, 1H, H-3), 3.06-3.15 (m, 1H, H-7a), 2.88-3.04 (m, 1H, H-8b), 2.79 (broad m, 1H, H-4b), 2.52-2.58 (m, 3H, H-3a, H-4a and H-8a), 2.29 (broad m, 1H, H-2), 2.15-2.20 (m, 1H, H-1b), 1.65-1.75 (m, 1H, H-1a), 1.44 (s, 9H, t-Bu), 1.05 (d, J=6.4 Hz, 2-CH$_3$). $^{13}$C-NMR (75 MHz, CDCl$_3$): δ=172.7 (CO), 155.5 (CO), 148.0 (2C), 134.3 (C), 125.1 (C), 111.6 (CH), 107.7 (CH), 79.4 (C(CH$_3$)$_4$), 69.0 (C-12b), 65.6 (CH), 56.2 (OMe), 55.8 (OMe) 49.3 (2C; 1CH, 1CH$_2$), 39.5 (CH), 35.7 (CH$_2$), 28.3 (5 C overlap, C(C$\underline{H}_3$)$_4$ and 1 CH$_2$), 27.0 (CH$_2$), 17.1 (2-CH$_3$). MS (ES): C$_{23}$H$_{32}$N$_2$O$_5$. Calc.: 417.2390 [M+H]$^+$. Found: 417.2373 [M+H]$^+$.

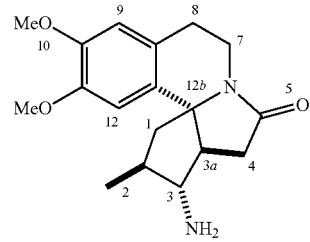

78

Cyclopenta[2,3]pyrrolo[2,1-a]isoquinoline-3-amino-1,2,3,3a,4,5,7,8-octahydro-10,11-dimethoxy-2-methyl-5-oxo-(2S,3R,3aS,12bR)

Compound 140 (2.5 g, 6.0 mmol) was dissolved in p-dioxane (10 mL) and treated with 4M HCl in dioxane (30 mL) at r.t. for 3.5 h. Dry Et$_2$O was added and the reaction mixture was filtered to give the HCl salt of 78 as an off-white solid, 2.0 g (94%). HPLC—(Method A)—$t_r$=0.93 min For nmr analysis the free base was made by partitioning the HCl salt between dichloromethane and sat. aq. K$_2$CO$_3$. HPLC—(Method B)—t$_r$=1.78 min

[α]$_D^{24}$=+182.5 (c=0.80, CHCl$_3$)

$^1$H-NMR (300 MHz, CDCl$_3$): δ=6.74 (s, 1H), 6.50 (s, 1H), 4.06-4.23 (m, H-7a), 3.85 (s, 3H, OMe), 3.80 (s, 3H, OMe), 3.03-3.09 (m, 1H), 2.98-3.00 (m, 1H), 2.61-2.65 (m, 1H), 2.47-2.58 (m, 3H), 2.34-2.44 (m, 1H), 2.13-2.22 (m, H-1b), 1.96 (m, 1H, H-2), 1.88 (broad singlet, 2H, NH$_2$), 1.66-1.74 (m, 1H, H-1a), 1.04 (d, J=6.1 Hz, 3H, 2-CH$_3$). $^{13}$C-NMR (75 MHz, CDCl$_3$): δ=173.0 (CO), 147.4 (2C overlap), 134.2, 125.2, 111.6, 107.5, 69.6, 66.2, 56.2 (OMe), 55.9 (OMe), 52.5, 49.8, 43.1, 35.7 (2C overlap), 27.1, 17.0 (2-CH$_3$). $^{13}$C-NMR (75 MHz, DMSO-d$_6$): δ=172.0 (CO), 148.2 (C), 148.1 (C) (these two aromatic carbons overlap in CDCl$_3$), 133.8 (C), 125.0 (C), 112.5 (CH), 108.6 (CH), 69.5 (C-12b), 63.8 (CH), 56.8 (OMe), 55.9 (OMe), 49.6 (CH$_2$), 47.6 (CH), 38.0 (CH), 35.6 (CH$_2$), 35.2 (CH$_2$) (these two CH$_2$'s overlap in CDCl$_3$), 26.7 (CH$_2$), 16.9 (2-CH$_3$). MS (ES): C$_{18}$H$_{24}$N$_2$O$_3$. Calc.: 317.1865 [M+H]$^+$ (HCl salt). Found: 317.1858 [M+H]$^+$.

36

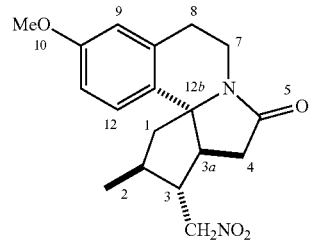

Cyclopenta[2,3]pyrrolo[2,1-a]isoquinoline-3-nitromethyl-1,2,3,3a,4,5,7,8-octahydro-10-methoxy-2-methyl-5-oxo-(2S,3R,3aS,12bR)

Compound 16 (30.6 g, 0.132 mol), 3-methoxyphenethylamine (24 g, 0.158 mol), EDC (30.4 g, 0.158 mol), HOBt (21.4 g, 0.158 mol) and triethylamine (46 mL, 2.5 equiv.) were dissolved in dichloromethane (400 mL) and stirred for 3 d at r.t. The reaction mixture was washed with water, 10% HCl and sat. aq. NaCl solution, then dried over anhydrous sodium sulfate and concentrated under reduced pressure. The residue was stirred with 5% TFA in dichloromethane (300 mL) at r.t. for 6.5 h. The reaction mixture was concentrated under reduced pressure. The residue was dissolved in dichloromethane, washed with water and sat. aq. NaHCO$_3$ solution, dried with anhydrous sodium sulfate and concentrated under reduced pressure. The crude product was purified by flash column chromatography on silica gel, eluting with 1-2% methanol in dichloromethane to yield 36, 17.2 g (39%) as a white foam. Additional impure material was also obtained. A smaller scale run on 5 g of 16 gave 36 in 46% yield. HPLC—(Method B)—t$_r$=5.45 min. (91%). An analytical sample was prepared by hplc: (Method A)—t$_r$=1.77 min.

[α]$_D^{24}$=+128.7 (c=0.55, CHCl$_3$)

$^1$H-NMR (300 MHz, CDCl$_3$/CD$_3$OD): δ=7.05 (d, J=8.5 Hz, 1H, H-12), 6.75 (dd, J=8.5, 2.0 Hz, 1H, H-11), 6.60 (d, J=2.0 Hz, 1H, H-9), 4.62-4.72 (m, 2H, CH$_2$NO$_2$), 4.06-4.13 (m, 1H, H-7b), 3.72 (s, 3H, OMe), 3.16-3.25 (m, 1H, H-7a), 2.90-3.01 (m, 1H, H-8b), 2.79-2.85 (m, 1H, H-3a), 2.67-2.73 (m, 1H, H-8a), 2.50-2.60 (m, 1H, H-4b), 2.24-2.30 (m, 1H, H-4a), 2.10-2.22 (m, 3H, H-2, H-3 and H-1b), 1.74-1.81 (m, 1H, H-1a), 1.06 (d, J=4.7 Hz, 3H, 2-CH$_3$). $^{13}$C-NMR (75 MHz, CDCl$_3$/CD$_3$OD): δ=173.2 (CO), 158.7 (C), 134.4 (C), 134.2 (C), 125.1 (CH), 114.0 (CH), 113.3 (CH), 77.4 (CH$_2$NO$_2$), 71.3 (C-12b), 55.2 (OMe), 52.8 (CH), 51.6 (CH$_2$), 48.0 (CH), 38.0 (CH), 36.6 (CH$_2$), 36.2 (CH$_2$), 27.8 (CH$_2$), 17.1 (2-CH$_3$). MS (ES): C$_{18}$H$_{22}$N$_2$O$_4$. Calc.: 331.1658 [M+H]$^+$. Found: 331.1656 [M+H]$^+$.

142

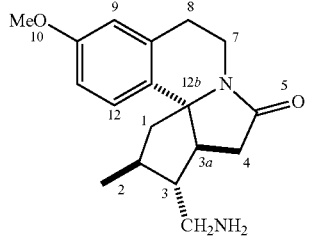

Cyclopenta[2,3]pyrrolo[2,1-a]isoquinoline-3-aminomethyl-1,2,3,3a,4,5,7,8-octahydro-10-methoxy-2-methyl-5-oxo-(2S,3R,3aS,12bR)

Compound 36 (5.17 g, 15.7 mmol) was dissolved in methanol (200 mL) and treated with ammonium formate (7.0 g, 0.11 mol) and 10% Pd/C (9.2 g), The mixture was heated at 80° C. for 6 h. The mixture was filtered hot over Celite and the cake was washed with hot methanol. The filtrate was concentrated under reduced pressure. The residue was dissolved in a mixture of EtOAc and MeOH and washed twice with small portions of sat. aq. NaCl. The organic layer was dried over anhydrous sodium sulfate and concentrated under reduced pressure. The residue was dissolved in anhydrous methanol and cooled on an ice bath. HCl (g) was bubbled in, followed by addition of dry Et$_2$O. Unfortunately a gummy residue was obtained, so the solvent was removed under reduced pressure. Trituration with Et$_2$O gave the white solid HCl salt of 142. HPLC—(Method A)—t$_r$=1.08 min. For nmr analysis the free base was made by partitioning the HCl salt between dichloromethane and sat. aq. K$_2$CO$_3$ to give 142 as a yellow oil, 1.82 g (39%). HPLC—(Method B)—t$_r$=1.78 min. $^1$H-NMR (300 MHz, CDCl$_3$): δ=6.90 (d, J=8.8 Hz, 1H, H-12), 6.51 (dd, J=8.8, 2.4 Hz, 1H, H-11), 6.32 (d, J=2.4 Hz, 1H, H-9), 3.89-3.96 (m, 1H, H-7b), 3.48 (s, 3H, OMe), 2.84-2.94 (m, 1H), 2.60-2.78 (m, 3H), 2.22-2.51 (m, 3H), 2.06-2.12 (m, 1H), 1.81-1.94 (m, 2H), 1.35-1.48 (m, 3H), 1.18 (m, 1H), 0.77 (d, J=5.8 Hz, 3H, 2-CH$_3$). $^{13}$C-NMR (75 MHz, CDCl$_3$): δ=172.5 (CO), 157.9 (C), 135.2 (C), 134.1 (C), 125.1 (CH), 113.4 (CH), 112.7 (CH), 70.4 (C-12b), 57.0 (CH), 54.9 (OMe), 52.0 (CH$_2$), 47.3 (CH), 42.6 (CH$_2$), 37.2 (CH$_2$), 36.7 (CH), 35.5 (CH$_2$), 27.7 (CH$_2$), 17.9 (2-CH$_3$). MS (ES): C$_{18}$H$_{24}$N$_2$O$_2$. Calc.: 301.1916 [M+H]$^+$ (HCl salt). Found: 301.1911 [M+H]$^+$.

143

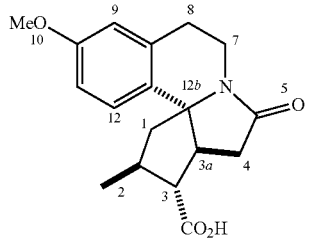

Cyclopenta[2,3]pyrrolo[2,1-a]isoquinoline-3-carboxylic acid-1,2,3,3a,4,5,7,8-octahydro-10-methoxy-2-methyl-5-oxo-(2S,3R,3aS,12bR)

Compound 36 (11.7 g, 35 mmol) was dissolved in DMF (100 mL) and treated with NaNO$_2$ (14.6 g, 0.218 mol) and HOAc (42 g, 0.688 mol). The reaction mixture was heated at 50° C. for 6.5 h. The reaction mixture was poured onto ice and carefully neutralized with solid NaHCO$_3$. The mixture was extracted with Et$_2$O (discarded) and then acidified with concentrated HCl. The aqueous layer was extracted twice with EtOAc/MeOH. The combined organic layers were extracted 10 times with sat. aq. NaCl solution. The organic layer was dried over anhydrous sodium sulfate and concentrated under reduced pressure to give 143 as an orange solid, 9.47 g (86%). An analytical sample was prepared by hplc. HPLC-(Method A)—t$_r$=1.46 min. (Method B)—t$_r$=4.53 min. $^1$H-NMR (300 MHz, DMSO-d$_6$): δ=7.20 (d, J=8.8 Hz, H-12), 6.82 (dd, J=8.8, 2.6 Hz, 1H, H-11), 6.65 (d, J=2.6 Hz, 1H, H-9), 3.89-3.97 (m, 1H, H-7b), 3.71 (s, 3H, OMe), 3.10-3.16 (m, 1H, H-7a), 2.96-3.04 (m, 1H, H-3a), 2.76-2.82 (m, 1H, H-8b), 2.62-2.72 (m, 1H, H-8a), 2.40-2.50 (m, 2H, H-2 and H-4b), 2.20-2.32 (m, 2H, H-3 and H-4, 2.04-2.11 (dd, J=13.2, 7.0 Hz, 1H, H-1), 1.79 (t, J=12.2 Hz, 1H, H-1a), 1.03 (d, J=6.2 Hz, 3H, 2-CH$_3$). $^{13}$C-NMR (75 MHz, DMSO-d$_6$): δ=175.1 (CO), 172.0 (CO), 158.6 (C), 135.3 (C), 135.2 (C), 125.7 (CH), 114.4 (CH), 113.6 (CH), 71.2 (C-12b), 59.7 (CH), 55.8 (OMe), 51.6 (CH$_2$), 48.2 (CH), 38.9 (CH), 37.1 (CH$_2$), 36.1 (CH$_2$), 27.8 (CH$_2$), 18.8 (2-CH$_3$). MS (ES): C$_{18}$H$_{21}$NO$_4$. Calc.: 316.1549 [M+H]$^+$. Found: 316.1532 [M+H]$^+$.

144

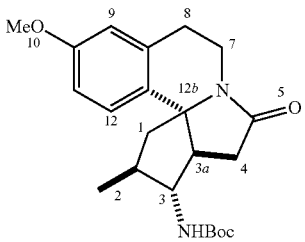

Cyclopenta[2,3]pyrrolo[2,1-a]isoquinoline-3-(N-t-butoxycarbonyl)amino-1,2,3,3a,4,5,7,8-octahydro-10-methoxy-2-methyl-5-oxo-(2S,3R,3aS,12bR)

Compound 36 (3.00 g, 9.5 mmol) was dissolved in dry THF (100 mL) and treated with Bu$_4$NBr (0.58 g, 1.80 mmol), NaN$_3$ (2.2 g, 33.8 mmol), di-t-butyldicarbonate (2.5 g, 11.4 mmol) and Zn(OTf)$_2$ (110 mg, 0.30 mmol) and then heated at 45° C. for 18 h. The reaction mixture was cooled to r.t. and a solution of NaNO$_2$ (8 g, 119 mmol) in water (75 mL) was added. After stirring 1 h the reaction mixture was diluted with EtOAc. After stirring another 20 min., the reaction mixture was extracted twice with EtOAc. The organic layers were washed twice with sat. aq. NH$_4$Cl, twice with sat. aq. NaHCO$_3$, then dried over anhydrous sodium sulfate and concentrated under reduced pressure. The crude product was passed over a pad of silica gel, eluting with 80/20 hexanes/EtOAc, then with 2% MeOH in dichloromethane to give 144, 2.82 g (77%), sufficiently pure for deprotection. An analytical sample was prepared by hplc. HPLC—(Method A)—t$_r$=1.94 min. (Method A)—t$_r$=5.99 min. $^1$H-NMR (300 MHz, CDCl$_3$, 60° C.): δ=7.14 (d, J=8.5 Hz, 1H, H-12), 6.74 (d, J=8.5 Hz, 1H, H-11), 6.57 (s, 1H, H-9), 4.87 (d, J=7.9 Hz, 1H, NH), 4.13-4.21 (m, 1H, H-7b), 3.74 (s, 3H, OMe), 3.39-3.42 (m, 1H, H-3), 3.08-3.14 (m, 1H, H-7a), 2.95-3.02 (m, 1H, H-8b), 2.45-2.69 (m, 4H, H-8a, H-4b, H-4a, H-3a), 2.10-2.16 (m, 2H, H-2 and H-1b), 1.66-1.74 (m, 1H, H-1a), 1.45 (s, 9H, t-Bu), 1.04 (d, J=5.9 Hz, 3H, 2-CH$_3$). $^{13}$C-NMR (75 MHz, CDCl$_3$): δ=172.8 (CO), 158.2 (C), 155.8 (CO), 134.7 (C), 134.4 (C), 125.1 (CH), 113.6 (CH), 113.1 (CH), 79.4 (C), 68.7 (C), 64.8 (CH), 55.2 (OMe), 50.0 (CH), 49.4 (CH$_2$), 40.1 (CH), 35.6 (CH$_2$), 28.4 (C(CH$_3$)$_4$), 27.81 (2 CH$_2$ overlap), 16.9 (2-CH$_3$). MS (ES): C$_{22}$H$_{30}$N$_2$O$_4$. Calc.: 387.2284 [M+H]$^+$. Found: 387.2284 [M+H]$^+$.

145

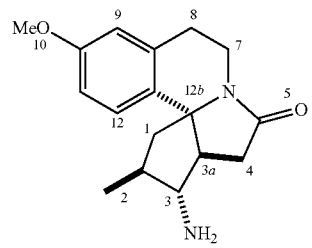

Cyclopenta[2,3]pyrrolo[2,1-a]isoquinoline-3-amino-1,2,3,3a,4,5,7,8-octahydro-10-methoxy-2-methyl-5-oxo-(2S,3R,3aS,12bR)

Compound 144 (2.4 g, 6.2 mmol) was treated with 4 M HCl in dioxane (30 mL) at r.t. for 3 h. Dry Et$_2$O was added and the reaction mixture was filtered. The solid was washed with Et$_2$O and dried under vacuum to give the HCl salt of 145 as a white solid, 1.92 g (96%). HPLC—(Method A)—t$_r$=1.09 min. (Method B)—t$_r$=2.04 min. For nmr analysis the free base was prepared by partitioning the HCl salt of 145 between dichloromethane and sat. aq. K$_2$CO$_3$.

[α]$_D^{24}$=+108.2 (c=1.45, CHCl$_3$)

$^1$H-NMR (300 MHz, CDCl$_3$): δ=7.15 (d, J=8.8 Hz, 1H, H-12), 6.73 (d, J=8.3 Hz, 1H, H=11), 6.54 (s, 1H, H-9), 4.12-4.18 (m, 1H, H-7b), 3.72 (s, 3H, OMe), 2.90-3.10 (m, 2H), 2.33-2.62 (m, 5H), 2.09-2.16 (m, 1H), 1.92 (m, 1H), 1.62-1.70 (m, 1H, H-1a), 1.47 (broad s, 2H, NH$_2$), 1.01 (d, J=6.1 Hz, 2-CH$_3$). $^{13}$C-NMR (75 MHz, CDCl$_3$): δ=172.8 (CO), 158.0 (C), 134.8 (C), 134.2 (C), 125.2 (CH), 113.5 (CH), 113.0 (CH), 69.0 (C-12b), 66.5 (CH), 55.1 (OMe), 52.5 (CH), 50.0 (CH$_2$), 42.9 (CH), 35.7 (CH$_2$), 35.4 (CH$_2$), 27.7 (CH$_2$), 16.8 (2-CH$_3$). MS (ES): C$_{17}$H$_{22}$N$_2$O$_2$. Calc.: 287.1760 [M+H]$^+$ (HCl salt). Found: 287.1767 [M+H]$^+$.

34

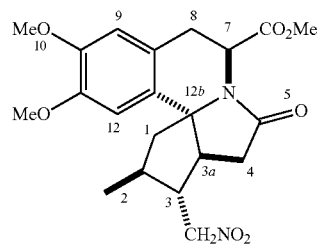

Cyclopenta[2,3]pyrrolo[2,1-a]isoquinoline-3-nitromethyl-7-carboxylic acid 1,2,3,3a,4,5,7,8-octahydro-10,11-dimethoxy-2-methyl-5-oxo-(2S,3R,3aS,7S,12bR)-Methyl ester Compound 16 (5.2 g, 22.6 mmol), L-3,4-dimethoxyphenylalanine methyl ester (5.4 g, 22.6 mmol), EDC (5.2 g, 27.1 mmol), HOBt (3.66 g, 27 mmol) and triethylamine (8 mL, 2.5 equiv.) were dissolved in dichloromethane (100 mL) and stirred o.n. at r.t. The reaction mixture was washed with water, 10% HCl and sat. aq. NaCl solution, then dried over anhydrous sodium sulfate and concentrated under reduced pressure. The residue was stirred with 5% TFA in dichloromethane (100 mL) at r.t. for 6 h. The reaction mixture was concentrated under reduced pressure. The residue was dissolved in dichloromethane, washed with water and sat. aq. NaHCO$_3$ solution, dried with anhydrous sodium sulfate and concentrated under reduced pressure. The crude product was purified by flash column chromatography on silica gel, eluting with 1-2% methanol in dichloromethane to yield 34, 6.41 g (68%) as a pale yellow foam. An analytical sample was prepared by hplc. HPLC—(Method A)—t$_r$=1.72 min. (Method B)—t$_r$=5.36 min.

[α]$_D^{24}$=+12.7 (c=0.805, CHCl$_3$)

$^1$H-NMR (300 MHz, CDCl$_3$): δ=6.74 (s, 1H), 6.64 (s, 1H), 4.62-4.72 (m, 2H, CH$_2$NO$_2$), 4.41-4.48 (dd, J=11.3, 7.1 Hz, 1H, H-7), 3.88 (s, 3H), 3.84 (s, 3H), 3.79 (s, 3H), 3.18-3.25 (m, 2H, H-3a and H-8b), 2.90-3.00 (dd, J=18.1, 10.6 Hz, 1H, H-8a), 2.68-2.78 (dd, J=18.1, 10.6 Hz, 1H, H-4b), 2.39-2.47 (dd, J=18.1, 4.2 Hz, 1H, H-4a), 2.12-2.23 (m, 2H, H-1b and H-3), 1.94-1.99 (m, 2H, H-1a and H-2), 1.07 (d, J=6.0 Hz, 3H, 2-CH$_3$). $^{13}$C-NMR (75 MHz, CDCl$_3$, 60° C.): δ=173.2 (CO), 171.9 (CO), 149.0 (C), 148.5 (C), 135.3 (C), 124.7 (C), 113.0 (CH), 107.6 (CH), 76.8 (CH$_2$NO$_2$), 70.93 (C-12b), 56.8 (OMe), 56.5 (OMe), 53.5 (CH), 52.6 (CO$_2$Me), 52.1 (CH), 50.1 (CH$_2$), 44.4 (CH), 37.0 (CH$_2$), 36.9 (CH), 30.1 (CH$_2$), 16.9 (2-CH$_3$). MS (ES): C$_{21}$H$_{26}$N$_2$O$_7$. Calc.: 419.1818 [M+H]$^+$. Found: 419.1807 [M+H]$^+$.

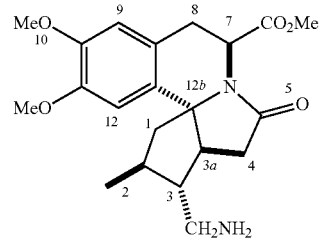

146

Cyclopenta[2,3]pyrrolo[2,1-a]isoquinoline-3-aminomethyl-7-carboxylic acid 1,2,3,3a,4,5,7,8-octahydro-10,11-dimethoxy-2-methyl-5-oxo-(2S,3R,3aS,7S,12bR)-Methyl ester Compound 34 (3.0 g, 7.2 mmol) was dissolved in methanol (100 mL) and treated with ammonium formate (4.2 g, 66 mmol) and 10% Pd/C (5.5 g), The mixture was heated at 75° C. for 3 h. The mixture was filtered hot over Celite and the cake was washed with hot methanol. The filtrate was concentrated under reduced pressure. The residue was dissolved in a mixture of ethyl acetate and methanol and washed three times with small portions of sat. aq. NaCl. The organic layer was dried over anhydrous sodium sulfate and concentrated under reduced pressure. The residue was dissolved in anhydrous methanol and cooled on an ice bath. HCl (g) was bubbled in, followed by addition of dry Et$_2$O. A solid did not form, so the mixture was concentrated under reduced pressure to give a pinkish foam of the HCl salt of 146, 2.20 g (79%). HPLC-(Method A)—t$_r$=1.09 min. (Method B)—t$_r$=2.49 min (85%)

The compound was further purified by making the free base by partitioning between dichloromethane and sat. aq. K$_2$CO$_3$, followed by flash chromatography on silica gel, eluting with 5-10% MeOH in dichloromethane and then with 10% 2M NH$_3$ in MeOH/90% dichloromethane. $^1$H-NMR (300 MHz, CDCl$_3$, 60° C.) δ=6.94 (s, 1H), 6.71 (s, 1H), 4.41-4.47 (m, 1H, H-7), 3.83 (s, 3H), 3.81 (s, 3H), 3.75 (s, 3H), 3.50-3.70 (broad s, 2H, NH$_2$), 3.07-3.19 (m, 3H, H-3a, H-8b, and CH$_a$H$_b$NH$_2$), 2.91-3.01 (m, 2H, H-8a and CH$_a$H$_b$NH$_2$), 2.67-2.77 (dd, J=18.1, 10.7 Hz, 1H, H-4-b), 2.46-2.54 (dd, J=18.1, 4.7 Hz, 1H, H-4a), 2.09-2.18 (m, 1H, H-1b), 1.80-1.91 (m, 2H, H-1a and H-2), 1.63-1.70 (m, 1H, H-3), 1.00 (d, J=5.9 Hz, 3H, 2-CH$_3$). $^{13}$C-NMR (75 MHz, CDCl$_3$, 25° C.): δ=173.7 (CO), 172.0 (CO), 147.9 (C), 147.7 (C), 136.0 (C), 124.2 (C), 111.7 (CH), 107.4 (CH), 71.0 (C-12b), 56.4 (2 C overlap, OMe and CH— at 60° C. these resonances are separated: 56.6 and 56.5 ppm), 56.1 (OMe), 52.5 (CO$_2$Me), 52.0 (CH), 50.4 (CH$_2$), 44.4 (CH), 42.5 (CH$_2$), 37.9 (CH$_2$), 36.4 (CH), 30.0 (CH$_2$), 17.3 (2-CH$_3$). MS (ES): C$_{21}$H$_{28}$N$_2$O$_5$. Calc.: 389.2076 [M+H]$^+$. Found: 389.2060 [M+H]$^+$.

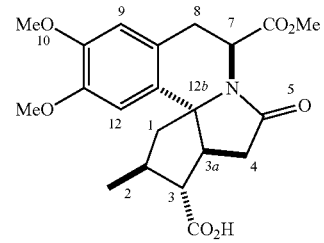

147

Cyclopenta[2,3]pyrrolo[2,1-a]isoquinoline-3,7-dicarboxylic acid 1,2,3,3a,4,5,7,8-octahydro-10,11-dimethoxy-2-methyl-5-oxo-(2S,3R,3aS,7S,12bR)-7-Methyl ester Compound 34 (3.15 g, 7.5 mmol) was dissolved in DMF (40 mL) and treated with NaNO$_2$ (3.11 g, 46 mmol) and HOAc (9 g, 0.147 mol). The reaction mixture was heated at 50° C. for 4 h. The reaction mixture was poured onto ice and carefully neutralized with solid NaHCO$_3$. The mixture was extracted with Et$_2$O and then acidified with concentrated HCl. The aqueous layer was extracted twice with a mixture of EtOAc and MeOH. The combined organic layers were extracted 10 times with sat. aq. NaCl solution. The organic layer was dried over anhydrous sodium sulfate and concentrated under reduced pressure to give 147 as a pale orange solid, 2.34 g (72%). An analytical sample was prepared by hplc. HPLC—(Method A)—t$_r$=1.42 min. (Method B)—t$_r$=4.41 min. $^1$H-NMR (300 MHz, CDCl$_3$): δ=7.14 (s, 1H), 6.74 (s, 1H), 4.40-4.47 (dd, J=11.6, 6.9 Hz, 1H, H-7), 3.89 (s, 3H), 3.86 (s, 3H), 3.81 (s, 3H), 3.46-3.51 (m, 1H, H-3a), 3.18-3.26 (dd, J=15.4, 6.9 Hz, 1H, H-8b), 2.91-3.00 (dd, J=15.1, 11.8 Hz, 1H, H-8a), 2.76-2.82 (dd, J=17.6, 10.8 Hz, 1H, H-4b), 2.50-2.60 (dd, J=17.9, 6.2 Hz, 1H, H-4a), 2.35-2.48 (m, 2H, H-2 and H-3), 2.20 (t, J=12.1 Hz, 1H, H-1b), 1.97-2.03 (m, 1H, H-1a), 1.16 (d, J=6.1 Hz, 3H, 2-CH$_3$). $^{13}$C-NMR (75 MHz, CDCl$_3$): δ=179.1 (CO), 173.0 (CO), 171.9 (CO), 148.1 (C), 147.9 (C), 135.1 (C), 123.9 (C), 111.6 (CH), 107.5 (CH), 71.6 (C-12b), 59.2 (CH), 56.2 (OMe), 56.1 (OMe), 52.6 (CO$_2$Me), 52.0 (CH), 50.0 (CH$_2$), 45.3 (CH), 39.3 (CH), 37.8 (CH$_2$), 30.0 (CH$_2$), 17.9 (2-CH$_3$). MS (ES): C$_{21}$H$_{25}$NO$_7$. Calc.: 404.1709 [M+H]$^+$. Found: 404.1720 [M+H]$^+$.

38

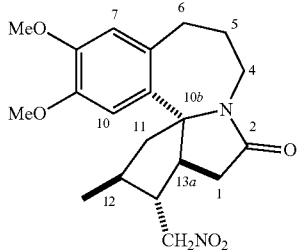

4H-Cyclopenta[2,3]pyrrolo[2,1-a][2]benzazepine-2 (1H)-one, 5,6,11,12,13,13a-hexahydro-8,9-dimethoxy-12-methyl-13-(nitromethyl)-(10bR,12S,13R,13aS)

3,4-Dimethoxycinnamonitrile (5 g) was dissolved in a mixture of EtOH (100 mL) and conc. HCl (10 mL) and hydrogenated with 10% Pd/C (wet, Degussa Type E101, Aldrich) at 65 psi on a Parr shaker for 70 h. The reaction mixture was filtered over Celite and the filtrate was concentrated to remove most of the EtOH. The residue was extracted twice with Et$_2$O (discarded) and then cooled with ice and made strongly basic with 10 M aq. NaOH solution. The basic aqueous layer was extracted with Et$_2$O and the organic layer was dried over anhydrous sodium sulfate and concentrated under reduced pressure to give 3-(3,4-dimethoxyphenyl)propylamine (5.07 g) as a pale yellow oil. $^1$H-NMR (300 MHz, CDCl$_3$): δ=6.68-6.78 (m, 3H), 3.83 (s, 3H, OMe), 3.82 (s, 3H, OMe), 2.70 (t, J=7.0 Hz, 2H), 2.58 (t, J=7.2 Hz, 2H), 1.70-1.75 (m, 2H), 1.17 (broad s, 2H, NH$_2$).

Compound 16 (6.35 g, 29.5 mmol), 3-(3,4-dimethoxyphenyl)propylamine (5.37 g, 27.5 mmol), EDC (5.3 g, 27.6 mmol), HOBt (3.7 g, 27.5 mmol) and triethylamine (5 mL, 36 mmol) were dissolved in dichloromethane (100 mL) and stirred o.n. at r.t. The reaction mixture was washed with water, 10% HCl, 1M aq. K$_2$CO$_3$ solution and sat. aq. NaCl solution, then dried over anhydrous sodium sulfate and concentrated under reduced pressure. The residue was stirred with 5% TFA in dichloromethane (100 mL) at r.t. for 7 h. The reaction mixture was concentrated under reduced pressure. The residue was dissolved in dichloromethane, washed with water and sat aq. NaHCO$_3$ solution, dried with anhydrous sodium sulfate and concentrated under reduced pressure. The crude product was purified by flash column chromatography on silica gel, eluting with 1% MeOH in dichloromethane to yield 38, 6.13 g (60%) as a pale orange foam. An analytical sample was prepared by hplc. HPLC—(Method A)—t$_r$=1.63 min. (Method B)—t$_r$=5.20 min (83%).

[α]$_D^{24}$=+133.6 (c=0.855, CHCl$_3$)

$^1$H-NMR (300 MHz, CDCl$_3$): δ=6.67 (s, 1H), 6.50 (s, 1H), 4.57-4.59 (m, 2H, CH$_2$NO$_2$), 4.18-4.26 (m, 1H, H-4b), 3.84 (s, 3H, OMe), 3.82 (s, 3H, OMe), 3.04-3.08 (m, 1H, H-4b), 2.85-2.91 (m, 1H), 2.70-2.75 (m, 1H), 2.52-2.61 (m, 2H), 2.29-2.38 (m, 2H), 2.07-2.22 (m, 2H), 1.90-1.98 (m, 2H), 1.77 (m, 1H), 1.13 (d, J=5.0 Hz, 3H, 12-CH$_3$). $^{13}$C-NMR (75 MHz, CDCl$_3$): δ=172.9 (CO), 147.4 (C), 147.3 (C), 135.8 (C), 132.6 (C), 114.0 (CH), 110.1 (CH), 76.2 (CH$_2$NO$_2$), 75.5 (C-10b), 56.3 (OMe), 55.8 (OMe), 51.6 (CH), 50.8 (CH), 47.9 (CH$_2$), 38.6 (CH), 38.0 (CH$_2$), 33.9 (CH$_2$), 32.2 (CH$_2$), 26.5 (CH$_2$), 18.1 (12-CH$_3$). MS (ES): C$_{20}$H$_{26}$N$_2$O$_5$. Calc.: 375.1920 [M+H]$^+$. Found: 375.1927 [M+H]$^+$.

148

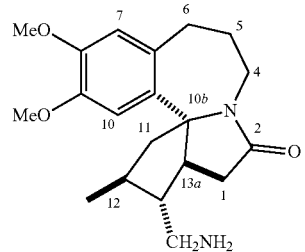

4H-Cyclopenta[2,3]pyrrolo[2,1-a][2]benzazepine-2 (1H)-one, 5,6,11,12,13,13a-hexahydro-8,9-dimethoxy-12-methyl-13-(aminomethyl)-(10bR,12S,13R,13aS)

Compound 38 (1.9 g, 5.1 mmol) was dissolved in methanol (100 mL) and treated with ammonium formate (2.0 g, 31 mmol) and 10% Pd/C (1.5 g), The mixture was heated at 75° C. for 4 h. The mixture was filtered hot over Celite and the cake was washed with hot MeOH. The filtrate was concentrated under reduced pressure. The residue was dissolved in a mixture of EtOAc and MeOH and washed three times with small portions of sat. aq. NaCl. The organic layer was dried over anhydrous sodium sulfate and concentrated under reduced pressure. The residue was purified by flash chromatography on silica gel, eluting with 5-10% MeOH in dichloromethane to give 148 as a yellow oil, 0.57 g (33%). HPLC—(Method A)—t$_r$=0.92 min. (Method B)—t$_r$=2.37 min. $^1$H-NMR (300 MHz, CDCl$_3$, 60° C.): δ=6.76 (s, 1H), 6.44 (s, 1H), 4.10-4.21 (m, 1H, H-4b), 3.77 (s, 3H, OMe), 3.74 (s, 3H, OMe), 2.95-3.04 (m, 1H, H-4a), 2.78-2.87 (m, 2H), 2.65-2.73 (m, 2H), 2.41-2.55 (m, 2H), 2.10-2.23 (m, 3H), 1.96-2.03 (m, 1H), 1.80-1.90 (m, 1H), 1.66-1.73 (m, 1H), 1.38 (broad s, 2H, NH$_2$), 1.25-1.35 (m, 1H), 1.00 (d, J=6.3 Hz, 3H, 12-CH$_3$). $^{13}$C-NMR (75 MHz, CDCl$_3$, 60° C.): δ=173.8 (CO), 147.7 (C), 147.6 (C), 137.5 (C), 133.0 (C), 114.9 (CH), 111.8 (CH), 76.3 (C-10b), 56.7 (OMe), 56.1 (OMe), 55.2 (CH), 51.8 (CH$_2$), 48.6 (CH), 42.5 (CH$_2$), 38.3 (CH$_2$), 38.0 (CH), 35.2 (CH$_2$), 32.7 (CH$_2$), 26.8 (CH$_2$), 18.9 (12-CH$_3$). MS (ES): C$_{20}$H$_{28}$N$_2$O$_3$. Calc.: 345.2178 [M+H]$^+$. Found: 345.2182 [M+H]$^+$.

149

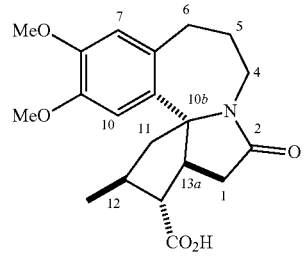

4H-Cyclopenta[2,3]pyrrolo[2,1-a][2]benzazepine-2 (1H)-one, 5,6,11,12,13,13a-hexahydro-8,9-dimethoxy-12-methyl-13-carboxylic acid-(10bR, 12S,13R,13aS)

Compound 38 (3.81 g, 10.2 mmol) was dissolved in DMF (60 mL) and treated with NaNO$_2$ (4.22 g, 63 mmol) and HOAc (12.2 g, 0.20 mol). The reaction mixture was heated at 50° C. for 5 h. The reaction mixture was poured onto ice and carefully neutralized with solid NaHCO$_3$. The mixture was extracted with Et$_2$O and then acidified with concentrated HCl. The aqueous layer was extracted twice with EtOAc. The combined organic layers were extracted 10 times with sat. aq. NaCl solution. The organic layer was dried over anhydrous sodium sulfate and concentrated under reduced pressure to give 149 as a pale yellow foam, 2.39 g (65%). HPLC—(Method A)—t$_r$=1.68 min. (Method B)—t$_r$=4.29 min (90%). (300 MHz, CDCl$_3$): δ=11.08 (broad s, CO$_2$H), 6.81 (s, 1H), 6.48 (s, 1H), 4.18-4.26 (m, 1H), 3.83 (s, 3H, OMe), 3.79 (s, 3H, OMe), 3.11-3.21 (m, 1H), 3.03-3.10 (m, 1H), 2.54-2.76 (m, 4H), 2.33-2.46 (m, 1H), 2.28-2.33 (m, 2H), 1.92-2.10 (m, 2H), 1.70-1.78 (m, 1H), 1.12 (d, J=6.4 Hz, 3H, 12-CH$_3$). $^{13}$C-NMR (75 MHz, CDCl$_3$): δ=177.2 (CO), 174.2 (CO), 147.2 (2C), 135.4 (C), 132.4 (C), 113.9 (CH), 110.2 (CH), 76.7 (C-10b), 57.5 (CH), 56.2 (OMe), 55.8 (OMe), 52.4 (CH), 47.6 (CH$_2$), 39.7 (CH), 38.5 (CH$_2$), 34.4 (CH$_2$), 32.3 (CH$_2$), 26.4 (CH$_2$), 18.7 (12-CH$_3$). MS (ES): C$_{20}$H$_{25}$NO$_5$. Calc.: 360.1811 [M+H]$^+$. Found: 360.1815 [M+H]$^+$.

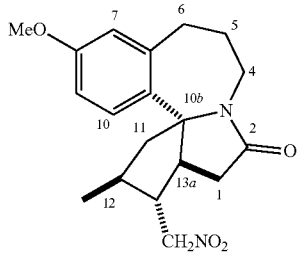

40

4H-Cyclopenta[2,3]pyrrolo[2,1-a][2]benzazepine-2 (1H)-one, 5,6,11,12,13,13a-hexahydro-8-methoxy-12-methyl-13-(nitromethyl)-(10bR,12S,13R,13aS)

3-Methoxybenzaldehyde (20.8 g, 0.15 mol) was treated with toluene (dry, 140 mL), pyridine (dry, 60 mL), ammonium acetate (0.59 g) and cyanoacetic acid (11.9 g, 0.14 mol) and then heated under reflux with a Dean-Stark trap for 71 h according to the procedure of Montgomery et. al (*J. Med. Chem.* 1993, 36, 55). The reaction mixture was concentrated under reduced pressure. The residue was dissolved in dichloromethane and washed with 10% aq. HCl, dried over anhydrous sodium sulfate and concentrated under reduced pressure. The crude product was purified by flash chromatography on silica gel, eluting with 2-5% EtOAc in hexanes to give 3-methoxycinnamonitrile, 14.65 g (60%). This material was dissolved in EtOH (75 mL) and conc. HCl (15 mL) and hydrogenated with 10% Pd/C (2.0 g) at 70 psi on a Parr shaker for 67 h. The reaction mixture was filtered over Celite. The filtrate was extracted with EtOAc, and the EtOAc layer was concentrated under vacuum to give the hydrochloride salt of 3-(3-methoxyphenyl)propylamine as a waxy white solid, 17.3 g (93%). HPLC—(Method B)—t$_r$=1.28 min. [M+H]$^+$=166.30. $^1$H-NMR (300 MHz, CDCl$_3$/CD$_3$OD): δ=7.14-7.19 (m, 1H), 6.70-6.77 (m, 3H), 4.51-4.58 (m, 2H), 3.75 (s, 3H, OMe), 2.85-2.91 (m, 2H), 2.63-2.68 (m, 2H), 1.95-2.01 (m, 2H).

Compound 16 (14.8 g, 69 mmol), 3-(3-methoxyphenyl)propylamine hydrochloride (17.3 g, 86 mmol), EDC (13.2 g, 69 mmol), HOBt (9.3 g, 69 mmol) and triethylamine (36 mL, 0.26 mol) were dissolved in dichloromethane (200 mL) and stirred o.n. at r.t. The reaction mixture was washed with water, 10% HCl, and sat. aq. NaCl solution, then dried over anhydrous sodium sulfate and concentrated under reduced pressure. The residue was stirred with 5% TFA in dichloromethane (200 mL) at r.t. for 3 h. Since the reaction had only gone 35% to completion (hplc), an additional 10 mL of TFA was added, followed by heating at reflux for 3 h. The reaction mixture was concentrated under reduced pressure. The residue was dissolved in dichloromethane, washed once with water and twice with sat aq. NaHCO$_3$ solution, dried with anhydrous sodium sulfate and concentrated under reduced pressure. The crude product was purified by flash column chromatography on silica gel, eluting with 1-5% methanol in dichloromethane to yield 40, 11.06 g (46%) as a tan foam. HPLC—(Method B)—t$_r$=5.75 min. (84%). An analytical sample was prepared by hplc. HPLC—(Method A)—t$_r$=1.89 min. $^1$H-NMR (300 MHz, CDCl$_3$/CD$_3$OD): δ=6.92 (d, J=8.8 Hz, 1H, H-10), 6.50 (dd, J=8.8, 2.8 Hz, 1H, H-9), 6.34 (d, J=2.5 Hz, 1H, H-7), 4.34-4.41 (m, 2H, CH$_2$NO$_2$), 3.90-4.00 (m, 1H, H-4b), 3.51 (s, 3H, OMe), 2.87-2.94 (m, 1H, H-4a), 2.61-2.65 (m, 1H, H-6b), 2.33-2.48 (m, 2H, H-1a and H-1b), 2.24-2.33 (dd. J=17.5, 7.9 Hz, 1H, H-6a), 1.90-2.09 (m, 3H, H-12, H-11b and H-5b), 1.72-1.85 (m, 3H, H-5a, H-11a and H-13), 1.53-1.60 (m, 1H, H-13a), 0.86 (d, J=5.8 Hz, 3H, 12-CH$_3$). The assignments are tentative, based on the COSY spectrum. $^{13}$C-NMR (75 MHz, CDCl$_3$/CD$_3$OD): δ=173.7 (CO), 158.1 (C), 141.4 (C), 135.6 (C), 127.2 (CH), 116.4 (CH), 111.8 (CH), 76.8 (CH$_2$NO$_2$), 75.9 (C-10b), 55.0 (OMe), 51.2 (CH), 50.3 (CH), 47.3 (CH$_2$), 38.7 and 38.6 (CH and CH$_2$), 33.7 (CH$_2$), 33.1 (CH$_2$), 26.2 (CH$_2$), 17.5 (12-CH$_3$). MS (ES): C$_{19}$H$_{24}$N$_2$O$_4$. Calc.: 345.1814 [M+H]$^+$. Found: 345.1821 [M+H]$^+$.

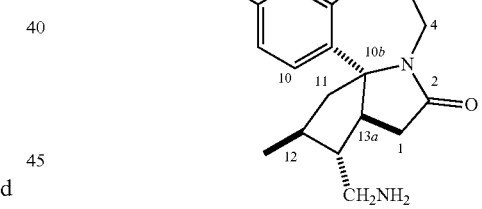

150

4H-Cyclopenta[2,3]pyrrolo[2,1-a]121 benzazepine-2 (1H)-one, 5,6,11,12,13,13a-hexahydro-8-methoxy-12-methyl-13-aminomethyl-(10bR,12S,13R,13aS)

Compound 40 (5.1 g, 14.8 mmol) was dissolved in methanol (200 mL) and treated with ammonium formate (7 g, 0.11 mol) and 10% Pd/C (9.2 g), The mixture was heated at 75° C. for 2 h. The mixture was filtered hot over Celite and the cake was washed with hot MeOH. The filtrate was concentrated under reduced pressure. The residue was dissolved in a mixture of EtOAc and MeOH and washed three times with small portions of sat. aq. NaCl. The organic layer was dried over anhydrous sodium sulfate and concentrated under reduced pressure, to give 150, 3.22 g (69%) as an pale yellow solid. HPLC—(Method A)—t$_r$=1.15 min. (Method B)—t$_r$=2.64 min (84%). $^1$H-NMR (300 MHz, CDCl$_3$): δ=7.17 (d, J=8.8 Hz, 1H, H-10), 6.67 (dd, J=8.5, 2.5 Hz, 1H, H-9), 6.51 (d, J=2.6 Hz, 1H, H-7), 4.16-4.22 (m, 1H), 3.70 (s, 3H, OMe), 3.01-3.06 (m, 1H), 2.84-2.87 (m, 2H), 2.60-2.77 (m, 3H), 2.42-2.51 (m, 1H), 2.12-2.27 (m, 3H), 1.90-1.99 (m, 2H), 1.74 (m, 1H), 1.61 (broad s, 2H, NH$_2$), 1.32 (m, 1H), 1.01 (d, J=5.9 Hz, 3H, 12-CH$_3$). $^{13}$C-NMR (75 MHz, CDCl$_3$): δ=174.1 (CO), 158.3 (C), 142.1 (C), 137.7 (C), 128.2 (CH), 116.7 (CH), 112.2 (CH), 76.2 (C-10b), 55.0 (CH), 51.5 (CH), 48.5 (CH$_2$), 42.7 (CH$_2$), 38.9 (CH$_2$), 38.0 (CH), 35.4 (CH$_2$), 34.0 (CH$_2$), 27.1 (CH$_2$), 19.3 (12-CH$_3$). MS (ES): C$_{19}$H$_{26}$N$_2$O$_2$. Calc.: 315.2072 [M+H]$^+$. Found: 315.2079 [M+H]$^+$.

151

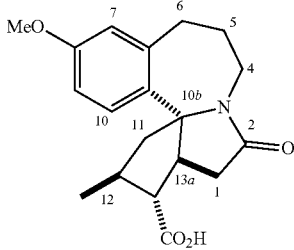

4H-Cyclopenta[2,3]pyrrolo[2,1-a][2]benzazepine-2(1H)-one, 5,6,11,12,13,13a-hexahydro-8-methoxy-12-methyl-13-carboxylic acid-(10bR,12S,13R,13aS)

Compound 40 (4.82 g, 14.0 mmol) was dissolved in DMF (60 mL) and treated with NaNO$_2$ (5.6 g, 84 mmol) and HOAc (12.2 g, 0.20 mol). The reaction mixture was heated at 50°C for 5.5 h. The reaction mixture was poured onto ice and carefully neutralized with solid NaHCO$_3$. The mixture was extracted with Et$_2$O and then acidified with concentrated HCl. The aqueous layer was extracted twice with a mixture of EtOAc and MeOH. The combined organic layers were extracted 10 times with sat. aq. NaCl solution. The organic layer was dried over anhydrous sodium sulfate and concentrated under reduced pressure. The residue was purified by flash chromatography on silica gel eluting with 5% EtOAc in hexanes to give 151 as a pale yellow foam, 2.60 g (56%). HPLC—(Method A)—t$_r$=1.57 min. (Method B)—t$_r$=4.77 min (90%). $^1$H-NMR (300 MHz, DMSO-d$_6$, 60° C.): δ=12.2 (broad s, 1H, CO$_2$H), 7.27 (d, J=8.4 Hz, 1H, H-10), 6.77 (dd, J=8.6, 2.7 Hz, 1H, H-9), 6.22 (d, J=2.5 Hz, 1H, H-7), 4.02-4.10 (m, 1H), 3.70 (s, 3H, OMe), 3.02-3.10 (m, 2H), 2.63-2.69 (m, 2H), 2.47-2.57 (m, 1H), 2.34-2.43 (m, 1H), 2.10-2.20 (m, 4H), 1.79-1.84 (m, 1H), 1.68-1.73 (m, 1H), 1.04 (d, J=6.6 Hz, 3H, 12-CH$_3$). $^{13}$C-NMR (300 MHz, DMSO-d$_6$, 60° C.): δ=175.3 (CO), 172.3 (CO), 158.3 (C), 142.2 (C), 137.1 (C), 127.9 (CH), 116.9 (CH), 112.4 (CH), 75.9 (C-10b), 57.9 (CH), 55.7 (OMe), 51.7 (CH), 47.3 (CH$_2$), 39.2 (CH), 38.6 (CH$_2$), 34.6 (CH$_2$), 33.5 (CH$_2$), 27.0 (CH$_2$), 19.0 (12-CH$_3$). MS (ES): C$_{19}$H$_{23}$NO$_4$. Calc.: 330.1705 [M+H]$^+$. Found: 330.1700 [M+H]$^+$.

114

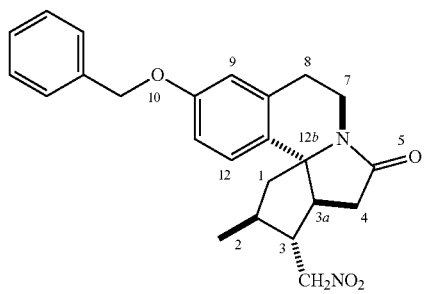

Cyclopenta[2,3]pyrrolo[2,1-a]isoquinoline-3-nitromethyl, 1,2,3,3a,4,5,7,8-octahydro-10-benzyloxy-2-methyl-5-oxo-(2S,3R,3aS,12bR)

A solution of 2-(3-hydroxyphenyl)ethyl amine (5.15 g, 29.7 mmol) in THF (65 mL) was treated with Et$_3$N (9.3 mL, 2.2 eq.) and cooled on an ice-water bath. Di-t-butyldicarbonate (6.8 g, 31.1 mmol) was added and the cooling bath was removed. After approx. 0.5 h, THF (35 mL) and Et$_3$N (5 mL) were added to improve solubility. After stirring o.n., the reaction mixture was diluted with EtOAc, washed with water and sat. aq. NaCl solution, dried over anhydrous sodium sulfate and concentrated under reduced pressure. The residue was dissolved in acetone (100 mL) and treated with benzyl bromide (3.9 mL, 33 mmol) and K$_2$CO$_3$ (4.5 g, 33 mmol). The reaction mixture was heated at 50° C. for 19 h. The solvent was removed under reduced pressure. The residue was partitioned between dichloromethane and 2 M aq. NaOH. The organic layer was washed with sat. aq. NaCl solution, dried over anhydrous sodium sulfate and concentrated under reduced pressure. The crude product, containing a small amount of residual benzyl bromide, was deprotected by treatment with p-dioxane (20 mL) and 4 M HCl in dioxane (50 mL) at r.t. for 2 h. The reaction mixture was diluted with Et$_2$O and the solid precipitate was filtered off, washed with Et$_2$O and dried to give 2-(3-benzyloxyphenyl)ethyl amine hydrochloride as a white solid, 5.49 g. HPLC—(Method A)—t$_r$=2.85 min. (94%). $^1$H-NMR (300 MHz, DMSO-d$_6$): δ=8.04 (broad s, 3H, NH$_3^+$), 7.34-7.42 (m, 4H), 7.22 (t, J=7.7 Hz, 1H), 6.80-6.91 (m, 3H), 5.07 (s, 2H, PhCH$_2$O), 3.00 (m, 2H), 2.81-2.85 (m, 2H).

Compound 16 (4.49 g, 20.9 mmol), 2-(3-benzyloxyphenyl)ethylamine hydrochloride (5.49 g, 20.9 mmol), EDC (4.4 g, 22.9 mmol), HOBt (3.1 g, 22.9 mmol) and triethylamine (12 mL, 86 mmol) were slurried in dichloromethane (100 mL) and stirred at r.t. After 1 h DMF (10 mL) was added to improve solubility. The homogeneous reaction mixture was then stirred at r.t. o.n. The reaction mixture was washed with water, 10% HCl, and sat. aq. NaCl solution, then dried over anhydrous sodium sulfate and concentrated under reduced pressure. The residue was stirred with 5% TFA in dichloromethane (100 mL) at r.t. for 4 h. The reaction mixture was concentrated under reduced pressure. The residue was dissolved in dichloromethane, washed once with water and twice with sat aq. NaHCO$_3$ solution, dried with anhydrous sodium sulfate and concentrated under reduced pressure. The crude product was purified by flash column chromatography on silica gel, eluting with 1% MeOH in dichloromethane to yield 114, 4.69 g (55%) as a foam. HPLC—(Method B)—t$_r$=6.86 min. (88%). An analytical sample was prepared by hplc. HPLC—(Method A)—t$_r$=2.71 min. $^1$H-NMR (300 MHz, CDCl$_3$): δ=7.25-7.39 (m, 5H, Ph), 7.01 (d, J=8.8 Hz, 1H, H-12), 6.83 (dd, J=8.6, 2.5 Hz, 1H, H-11), 6.68 (d, J=2.8 Hz, 1H, H-9), 5.01 (s, 2H, PhCH$_2$O), 4.50-4.69 (m, 2H, CH$_2$NO$_2$), 4.16-4.24 (m, 1H, H-7b), 3.10-3.20 (m, 1H, H-7a or H-8b), 2.95-3.06 (m, 1H, H-8b or H-7a), 2.76-2.80 (m, 1H, H-3a), 2.63-2.69 (m, 1H, H-8a), 2.52-2.62 (m, 1H, H-4b), 2.23-2.29 (m, 2H, H-4a and H-1b), 2.08-2.22 (m, 2H, H-2 and H-3), 1.73-1.82 (m, 1H, H-1a), 1.08 (d, J=5.5 Hz, 3H, 2-CH$_3$). $^{13}$C-NMR (75 MHz, CDCl$_3$): δ=172.4 (CO), 157.8 (C), 137.0 (C), 134.8 (C), 134.7 (C), 128.9 (CH), 128.2 (CH), 127.7 (CH), 125.1 (CH), 115.2 (CH), 114.1 (CH), 77.5 (CH$_2$NO$_2$), 70.6 (C-12b), 70.2 (PhCH$_2$O), 52.9 (CH), 51.8 (CH$_2$), 48.1 (CH), 38.2 (CH), 36.5 (CH$_2$), 36.1 (CH$_2$), 28.0 (CH$_2$), 17.7 (2-CH$_3$). MS (ES): C$_{24}$H$_{26}$N$_2$O$_4$. Calc.: 407.1971 [M+H]$^+$. Found: 407.1978 [M+H]$^+$.

81

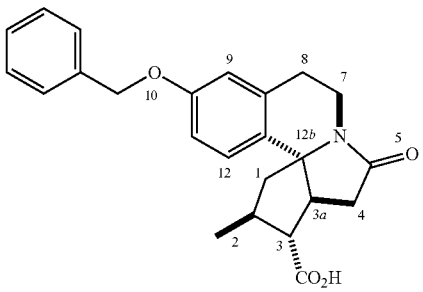

118

Cyclopenta[2,3]pyrrolo[2,1-a]isoquinoline-3-carboxylic acid, 1,2,3,3a,4,5,7,8-octahydro-10-benzyloxy-2-methyl-5-oxo-(2S,3R,3aS,12bR)

Compound 114 (4.6 g, 11.3 mmol) was dissolved in DMF (50 mL) and treated with NaNO$_2$ (4.7 g, 68 mmol) and HOAc (14 g, 0.227 mol). The reaction mixture was heated at 50° C. for 5 h. The reaction mixture was poured onto ice and carefully neutralized with solid NaHCO$_3$. The mixture was extracted with Et$_2$O and then acidified with concentrated HCl. The aqueous layer was extracted twice with a mixture of EtOAc and MeOH. The combined organic layers were extracted 10 times with sat. aq. NaCl solution. The organic layer was dried over anhydrous sodium sulfate and concentrated under reduced pressure. The residue was purified by flash chromatography on silica gel eluting with 5% MeOH in dichloromethane to give 118 as a foam, 2.13 g (48%). HPLC—(Method B)—t$_r$=6.02 min. (75% by U.V., >90% ELSD). An analytical sample was prepared by hplc. HPLC-(Method A)—t$_r$=2.32 min.

[α]$_D^{24}$=+88.5 (c=0.61, CHCl$_3$)

$^1$H-NMR (300 MHz, CDCl$_3$): δ=8.50 (broad s, 1H, CO$_2$H), 7.33-7.40 (m, 5H, Ph), 7.25 (d, J=8.5 Hz, 1H, H-12), 6.85 (dd, J=8.5, 2.2 Hz, 1H, H-11), 6.68 (d, J=2.2 Hz, 1H, H-9), 5.02 (s, 2H, PhCH$_2$O), 4.19-4.26 (m, 1H, H-7b), 3.14-3.20 (m, 2H, H-3a and H-7a), 2.99-3.08 (m, 1H, H-8b), 2.47-2.68 (m, 4H, H-8a, H-4-b, H-4a, H-2), 2.34-2.42 (t, J=10.2 Hz, 1H, H-3), 2.22-2.29 (dd, J=12.8, 7.0 Hz, 1H, H-1b), 1.72-1.81 (t, J=12.5, 1H, H-1a), 1.13 (d, J=6.3 Hz, 3H, 2-CH$_3$). $^{13}$C-NMR (75 MHz, CDCl$_3$): δ=178.3 (CO), 173.2 (CO), 157.9 (C), 137.0 (C), 134.6 (C), 134.5 (C), 128.8 (CH), 128.3 (CH), 127.7 (CH), 125.6 (CH), 115.1 (CH), 114.1 (CH), 71.8 (C-12b), 70.3 (PhCH$_2$O), 59.7 (CH), 51.9 (CH$_2$), 48.3 (CH), 39.2 (CH), 37.1 (CH$_2$), 36.3 (CH$_2$), 28.1 (CH$_2$), 18.4 (2-CH$_3$). MS (ES): C$_{24}$H$_{25}$NO$_4$. Calc.: 392.1862 [M+H]$^+$. Found: 392.1872 [M+H]$^+$.

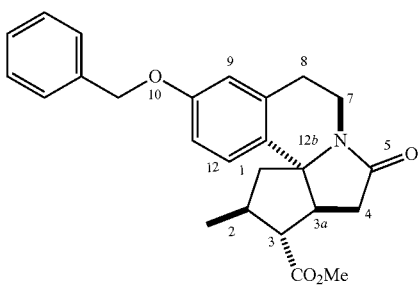

120

82

Cyclopenta[2,3]pyrrolo[2,1-a]isoquinoline-3-carboxylic acid, 1,2,3,3a,4,5,7,8-octahydro-10-benzyloxy-2-methyl-5-oxo-(2S,3R,3aS,12bR)-Methyl ester Compound 118 (1.46 g, 3.7 mmol) was dissolved in a 1/1 mixture of MeOH and dichloromethane (20 mL) and treated with excess 2M TMS diazomethane in Et$_2$O. After 0.5 h the solvent was removed under reduced pressure and the residue was purified by flash column chromatography on silica gel, eluting with 1-2% MeOH in dichloromethane to give 120 as a yellow oil, 1.29 g (85%). HPLC—(Method A)—t$_r$=2.25 min. (Method B)—t$_r$=6.86 min (100%) $^1$H-NMR (300 MHz, CDCl$_3$): δ=7.29-7.42 (m, 5H, Ph), 7.23 (d, J=8.8 Hz, 1H, H-12), 6.85 (dd, J=8.5, 2.6 Hz, 1H, H-11), 6.68 (d, J=2.6 Hz, 1H, H-9), 5.03 (s, 2H, PhCH$_2$O), 4.16-4.24 (m, 1H, H-7b), 3.77 (s, 3H, CO$_2$Me), 3.10-3.17 (m, 2H, H-7b and H-3a), 2.95-3.06 (m, 1H, H-8b), 2.65-2.69 (m, 1H, H-8a), 2.51-2.63 (m, 2H, H-4b and H-2), 2.36-2.42 (m, 2H, H-4a and H-3), 2.20-2.27 (dd, J=13.1, 7.2 Hz, 1H, H-1b), 1.72-1.80 (t, J=12.2 Hz, 1H, H-1a), 1.08 (d, J=6.5 Hz, 3H, 2-CH$_3$). $^{13}$C-NMR (75 MHz, CDCl$_3$): δ=174.4 (CO), 172.2 (CO), 157.5 (C), 136.9 (C), 134.4 (2 C), 128.5 (CH), 127.9 (CH), 127.3 (CH), 125.3 (CH), 114.8 (CH), 113.8 (CH), 71.1 (C-12b), 69.8 (PhCH$_2$O), 59.2 (CH), 51.9 (CO$_2$Me), 51.5 (CH$_2$), 48.1 (CH), 39.0 (CH), 36.7 (CH$_2$), 35.8 (CH$_2$), 27.7 (CH$_2$), 18.2 (2-CH$_3$). MS (ES): C$_{25}$H$_{27}$NO$_4$. Calc.: 406.2018 [M+H]$^+$. Found: 406.2006 [M+H]$^+$.

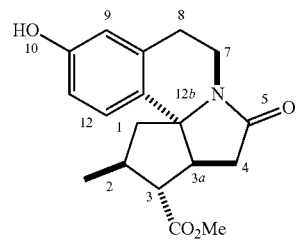

124

Cyclopenta[2,3]pyrrolo[2,1-a]isoquinoline-3-carboxylic acid, 1,2,3,3a,4,5,7,8-octahydro-10-hydroxy-2-methyl-5-oxo-(2S,3R,3aS,12bR)-Methyl ester Compound 120 (3.05 g, 7.5 mmol) was dissolved in EtOH (60 mL) and hydrogenated with 10% Pd/C (1.5 g) at 34 psi of H$_2$ in a Parr shaker for 7 h. The reaction mixture was filtered over Celite and the filtrate was concentrated under reduced pressure to give 124 as a tan solid, 2.06 g (87%). An analytical sample was purified by flash chromatography on silica gel, eluting with 2% MeOH in dichloromethane. HPLC—(Method A)—t$_r$=1.63 min. (Method B)—t$_r$=4.22 min (96%)

[α]$_D^{24}$=+124.4 (c=0.73, CHCl$_3$)

$^1$H-NMR (300 MHz, CDCl$_3$): δ=7.94 (broad s, 1H, OH), 7.13 (d, J=8.8 Hz, 1H, H-12), 6.74 (dd, J=8.5, 2.6 Hz, 1H, H-11), 6.56 (d, J=2.3 Hz, 1H, H-9), 4.12-4.20 (m, 1H, H-7b), 3.76 (s, 3H, CO$_2$Me), 3.08-3.18 (m, 2H, H-7a and H-3a), 2.89-3.00 (m, 1H, H-8b), 2.50-2.68 (m, 3H, H-4b, H-8a and H-2), 2.29-2.45 (m, 2H, H-4a and H-3), 2.19-2.26 (m, 1H, H-1b), 1.69-1.78 (t, J=12.5 Hz, 1H, H-1a), 1.06 (d, J=6.4 Hz, 3H, 2-CH$_3$). $^{13}$C-NMR (75 MHz, CDCl$_3$): δ=174.7 (CO), 173.0 (CO), 155.7 (C), 134.2 (C), 133.0 (C), 125.3 (CH), 115.4 (CH), 114.5 (CH), 71.7 (C-12b), 59.3 (CH), 52.1 (CO$_2$Me), 51.5 (CH$_2$), 48.0 (CH), 39.0 (CH), 36.8 (CH$_2$), 36.2

(CH$_2$), 27.6 (CH$_2$), 18.1 (2-CH$_3$). MS (ES): C$_{18}$H$_{21}$NO$_4$. Calc.: 316.1549 [M+H]$^+$. Found: 316.1554 [M+H]$^+$.

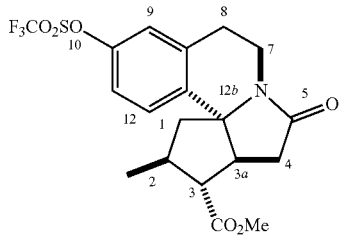

126

Cyclopenta[2,3]pyrrolo[2,1-a]isoquinoline-3-carboxylic acid, 1,2,3,3a,4,5,7,8-octahydro-10-(trifluoromethanesulfonyl)oxy-2-methyl-5-oxo-(2S,3R,3aS,12bR)-Methyl ester Compound 124 (1.14 g, 3.6 mmol) was dissolved in dry dichloromethane (20 mL), treated with Et$_3$N (1.2 mL, 8.6 mmol) and cooled on an ice-water bath. A solution of trifluoromethanesulfonic anhydride (0.73 mL, 4.3 mmol) in dichloromethane (5 mL) was added dropwise. After 1.5 h the reaction mixture was washed with sat. aq. NaHCO$_3$ and sat. aq. NaCl solutions, dried over anhydrous sodium sulfate and concentrated under reduced pressure. The residue was purified by flash column chromatography on silica gel, eluting with 1/1 hexanes/EtOAc to give 126 as a brown oil, 0.83 g (51%). HPLC—(Method A)—t$_r$=2.03 min. (Method B)—t$_r$=6.43 min. $^1$H-NMR (300 MHz, CDCl$_3$): δ=7.39 (d, J=8.5 Hz, 1H, H-12), 7.09 (dd, J=8.5, 2.5 Hz, 1H, H-11), 6.96 (d, J=2.5 Hz, 1H, H-9), 4.17-4.24 (m, 1H, H-7b), 3.74 (s, 3H, CO$_2$Me), 3.05-3.18 (m, 2H), 2.96-3.02 (m, 1H), 2.70-2.76 (m, 1H), 2.50-2.61 (m, 2H), 2.33-2.41 (m, 2H), 2.20-2.33 (m, 1H), 1.71-1.80 (t, J=12.5 Hz, 1H, H-1a), 1.07 (d, J=6.3 Hz, 3H, 2-CH$_3$). $^{13}$C-NMR (75 MHz, CDCl$_3$): δ=174.4 (CO), 172.2 (CO), 148.2, 142.5, 136.2, 126.5, 121.9, 120.0, 117.8 (q, CF$_3$, J$_{C,F}$=320 Hz), 71.4, 59.6, 52.4, 51.6, 48.6, 39.6, 37.0, 35.7, 27.9, 18.5 (2-CH$_3$). MS (ES): C$_{19}$H$_{20}$F$_3$NO$_6$S. Calc.: 448.1042 [M+H]$^+$. Found: 448.1023 [M+H]$^+$.

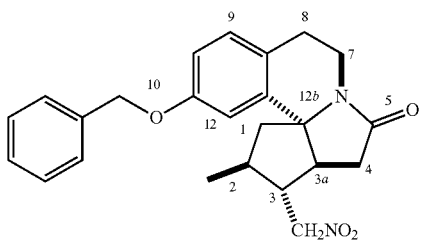

112

Cyclopenta[2,3]pyrrolo[2,1-a]isoquinoline-3-nitromethyl, 1,2,3,3a,4,5,7,8-octahydro-11-benzyloxy-2-methyl-5-oxo-(2S,3R,3aS,12bR)

A solution of tyramine (10.15 g, 74 mmol) in THF (100 mL) was treated with Et$_3$N (8.3 mL, 60 mmol) and cooled on an ice-water bath. Di-t-butyldicarbonate (14.5 g, 64 mmol) was added and the cooling bath was removed. After stirring o.n., the reaction mixture was diluted with EtOAc, washed with water and sat. aq. NaCl solution, dried over anhydrous sodium sulfate and concentrated under reduced pressure. The residue was dissolved in acetone (100 mL) and treated with benzyl bromide (8.0 mL, 67 mmol) and K$_2$CO$_3$ (9.1 g, 66 mmol). The reaction mixture was heated at 50° C. for 7.5 h. The solvent was removed under reduced pressure. The residue was partitioned between dichloromethane and 2M aq. NaOH. The organic layer was washed with sat. aq. NaCl solution, dried over anhydrous sodium sulfate and concentrated under reduced pressure to give a white solid, 17.5 g. HPLC—(Method B)—t$_r$=7.71 min (>95% purity by ELSD). [M]$^-$=326.19 (C$_{20}$H$_{25}$NO$_3$=327). $^1$H-NMR (300 MHz, CDCl$_3$): δ=7.26-7.44 (m, 4H), 7.10 (d, J=8.5 Hz, 2H), 6.91 (d, J=8.5 Hz, 2H), 5.05 (s, 2H, PhCH$_2$O), 3.33 (m, 2H), 2.70-2.75 (m, 2H), 1.43 (s, 9H, Boc).

The crude product above, 15.4 g, containing a small amount of residual benzyl bromide, was de-protected by treatment with 4 M HCl in dioxane (100 mL) at r.t. After 0.5 h, p-dioxane (50 mL) was added to facilitate stirring. After 4.5 h the reaction mixture was diluted with Et$_2$O and the solid precipitate was filtered off, washed with Et$_2$O and dried to give 2-(4-benzyloxyphenyl)ethyl amine hydrochloride as a white solid, 11.7 g. HPLC—(Method B)—t$_r$=2.72 min. (96%). $^1$H-NMR (300 MHz, DMSO-d$_6$): δ=8.06 (broad s, 3H, NH$_3^+$), 7.28-7.40 (m, 4H), 7.15 (d, J=8.5 Hz, 2H), 6.94 (d, J=8.5 Hz, 2H), 5.06 (s, 2H, PhCH$_2$O), 2.93 (m, 2H), 2.77-2.83 (m, 2H). $^{13}$C-NMR (DMSO-d$_6$): δ 17.4, 26.6, 36.1, 36.3, 38.1, 47.9, 51.6, 52.8, 70.3, 70.3, 110.7, 113.5, 125.3, 127.5 128.1, 128.7, 130.4, 136.8, 142.9, 142.9, 157.4, 171.9.

The free base was made by partitioning the solid between Et$_2$O and 2 M aq. NaOH solution. The organic layer was washed with sat. aq. NaCl solution, dried over anhydrous sodium sulfate and concentrated under reduced pressure to give 2-(4-benzyloxyphenyl)ethyl amine as a white solid, 8.92 g.

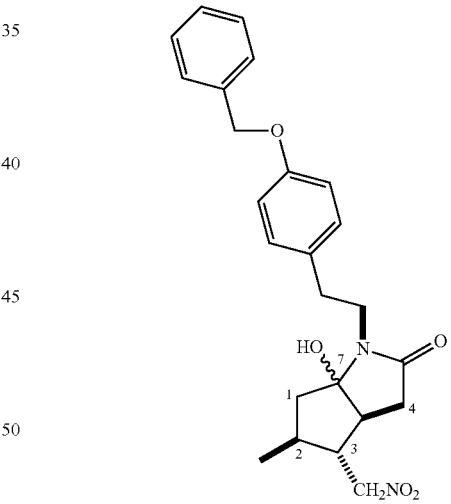

152

Compound 16 (9.07 g, 39.3 mmol), 2-(4-benzyloxyphenyl)ethylamine (8.92 g, 39.3 mmol), EDC (7.7 g, 40 mmol), HOBt (5.4 g, 40 mmol) and triethylamine (12 mL, 86 mmol) were slurried in dichloromethane (200 mL) and stirred at r.t. o.n. The now homogeneous reaction mixture was washed with water, 10% HCl, and sat. aq. NaCl solution, then dried over anhydrous sodium sulfate and concentrated under reduced pressure. The crude residue was purified by flash chromatography on silica gel to give 152, 8.44 g (51%) as a pale yellow solid. When this reaction was repeated, the chromatographed intermediate A contained approx. 15% of what appeared to be an epimer at C-7 (as judged by the ratio of two broadened singlets at 5.63 ppm (15%) and 5.53 ppm (85%) assigned to the 7-OH— both peaks exchange with D$_2$O). The 2-CH$_3$ also appears as a pair of doublets (0.61 ppm, approx 72%) and 0.58 ppm, approx 28%). HPLC—(Method B)—t$_r$=6.47 min. (90%) [M-OH]$^+$=407.28, [M]$^-$=423.21 (C$_{24}$H$_{28}$N$_2$O$_5$=424). $^1$H-NMR (300 MHz, DMSO-d$_6$): δ=7.29-7.40 (m, 5H), 7.11 (d, J=8.5 Hz, 2H), 6.92 (d, J=8.5 Hz, 2H), 5.93 (s, 1H, 7-OH, exchanges with D$_2$O), 5.04 (s, 2H, PhC$\underline{H}_2$O), 4.69-4.73 (m, 1H, C$\underline{H}_b$H$_a$NO$_2$), 4.52-4.59 (m, 1H, CH$_b\underline{H}_a$NO$_2$), 3.20-3.33 (m, 2H), 2.73-2.88 (m, 2H), 2.44-2.54 (dd, J=17.2, 9.8 Hz, 1H), 2.13-2.21 (m, 1H), 1.98-2.08 (m, 2H), 1.75-1.93 (m, 2H), 1.81 (t, J=12.0 Hz, 1H), 0.85 (d, J=6.0 Hz, 3H, 2-CH$_3$). $^{13}$C-NMR (75 MHz, DMSO-d$_6$): δ=172.5 (CO), 157.3 (C), 137.7 (C), 132.1 (C), 130.1 (CH), 128.8 (CH), 128.2 (CH), 128.0 (CH), 115.2 (CH), 98.2 (C, assigned to C-7), 78.2 ($\underline{C}$H$_2$NO$_2$), 69.6 (Ph$\underline{C}$H$_2$O), 52.1 (CH), 49.5 (CH), 47.1 (CH$_2$), 41.9 (CH$_2$), 36.5 (CH), 35.5 (CH$_2$), 33.9 (CH$_2$), 17.2 (2-CH$_3$). No peaks at >172 ppm corresponding to a ketone carbonyl were observed.

152 (1.0 g, 2.4 mmol) was stirred with 5% TFA in dichloromethane (25 mL) at r.t. for 4 h. By LCMS analysis, only unreacted 152 was present (t$_r$=6.49 min). TFA (1.25 mL) was added and the reaction mixture was heated to reflux for 5.5 h. LCMS analysis indicated 90% conversion to 112 (t$_r$=6.85 min.). After refluxing o.n., the reaction mixture was diluted with dichloromethane, washed with water and sat aq. NaHCO$_3$ solution, dried with anhydrous sodium sulfate and concentrated under reduced pressure. The crude product was purified by flash column chromatography on silica gel, eluting with 2% methanol in dichloromethane to yield 112, 0.82 g (86%) as a yellow oil. HPLC—(Method B)—t$_r$=6.85 min. (95%). An analytical sample was prepared by HPLC. HPLC—(Method A)—t$_r$=2.25 min. $^1$H-NMR (300 MHz, CDCl$_3$/CD$_3$OD): δ=7.24-7.36 (m, 5H, Ph), 6.95 (d, J=8.5 Hz, 1H, H-9), 6.79 (dd, J=8.1, 2.5 Hz, 1H, H-10), 6.61 (d, J=2.4 Hz, 1H, H-12), 5.02 (s, 2H, PhC$\underline{H}_2$O), 4.45-4.65 (m, 2H, C$\underline{H}_2$NO$_2$), 4.06-4.13 (m, 1H, H-7b), 3.08-3.18 (m, 1H, H-7a), 2.78-2.95 (m, 1H, H-8b), 2.72-2.77 (m, 1H, H-3a), 2.58-2.66 (m, 1H, H-8a), 2.49-2.55 (m, 1H, H-4b), 2.19-2.27 (m, 2H, H-4a and H-1b), 1.95-2.08 (m, 2H, H-2 and H-3), 1.66-1.75 (t, J=12.0 Hz, 1H, H-1a), 1.01 (d, J=5.5 Hz, 3H, 2-CH$_3$). $^{13}$C-NMR (75 MHz, CDCl$_3$): δ=172.0 (CO), 157.4 (C), 142.9 (C), 136.8 (C), 130.4 (CH), 128.7 (CH), 128.1 (CH), 127.5 (CH), 125.3 (C), 113.5 (CH), 110.7 (CH), 76.6 ($\underline{C}$H$_2$NO$_2$), 70.7 (C-12b), 70.3 (Ph$\underline{C}$H$_2$O), 52.8 (CH), 51.6 (CH$_2$), 47.9 (CH), 38.1 (CH), 36.3 (CH$_2$), 36.1 (CH$_2$), 26.6 (CH$_2$), 17.4 (2-CH$_3$). MS (ES): C$_{24}$H$_{26}$N$_2$O$_4$. Calc.: 407.1971 [M+H]$^+$. Found: 407.1955 [M+H]$^+$ When a new batch of intermediate A, 7.24 g was heated at reflux for 10.5 h in a mixture of dichloromethane (70 mL) and TFA (7 mL), followed by workup and silica gel chromatography, 112 was obtained as a pale yellow foam, 5.12 g (74%).

116

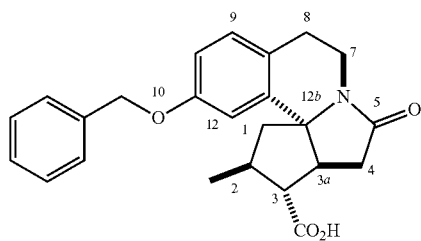

Cyclopenta[2,3]pyrrolo[2,1-a]isoquinoline-3-carboxylic acid, 1,2,3,3a,4,5,7,8-octahydro-11-benzyloxy-2-methyl-5-oxo-(2S,3R,3aS,12bR)

Compound 112 (5.12 g, 12.6 mmol) was dissolved in DMF (60 mL) and treated with NaNO$_2$ (5.22 g 75 mmol) and HOAc (15.1 g, 0.25 mol). The reaction mixture was heated at 50° C. for 4 h. The reaction mixture was poured onto ice and carefully neutralized with solid NaHCO$_3$. The mixture was extracted with Et$_2$O and then acidified with concentrated HCl. The aqueous layer was extracted twice with a mixture of EtOAc and MeOH. The combined organic layers were extracted 10 times with sat. aq. NaCl solution. The organic layer was dried over anhydrous sodium sulfate and concentrated under reduced pressure. The residue was purified by flash chromatography on silica gel eluting with 3% MeOH in dichloromethane to give 116 as a foam, 3.21 g (65%).

HPLC—(Method A)—t$_r$=1.92 min (Method B)—t$_r$=5.79 min (100% purity by ELSD)

[α]$_D^{22}$=+134.7 (c=0.95, CHCl$_3$)

$^1$H-NMR (300 MHz, CDCl$_3$): δ=7.26-7.43 (m, 5H, Ph), 6.98 (d, J=8.5 Hz, 1H, H-9), 6.92 (d, 1H, J=2.3 Hz, 1H, H-12), 6.80 (dd, J=8.5, 2.6 Hz, 1H, H-10), 5.04 (s, 2H, PhC$\underline{H}_2$O), 4.17-4.24 (m, 1H, H-7b), 3.10-3.21 (m, 2H), 2.94-3.02 (m, 1H), 2.44-2.68 (m, 4H), 2.31-2.39 (t, J=10.2 Hz, 1H), 2.19-2.26 (dd, J=13.0, 6.9 Hz, 1H), 1.69-1.78 (t, J=12.4 Hz, 1H, H-1a), 1.10 (d, J=6.5 Hz, 3H, 2-CH$_3$). $^{13}$C-NMR (75 MHz, CDCl$_3$): δ=177.1 (CO), 172.7 (CO), 157.5, 142.9, 136.8, 130.1, 128.6, 128.0, 127.6, 125.1, 113.7, 110.7, 71.8, 70.1, 59.4, 51.6, 48.0, 39.0, 36.8, 36.3, 26.7, 18.1 (2-CH$_3$). MS (ES): C$_{24}$H$_{25}$NO$_4$. Calc.: 392.1862 [M+H]$^+$. Found: 392.1860 [M+H]$^+$.

50

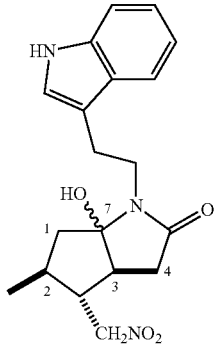

Compound 16 (6.57 g, 28.1 mmol), tryptamine (5.4 g, 33.7 mmol), EDC (6.48 g, 33.7 mmol), HOBt (4.55 g, 33.7 mmol) and triethylamine (10 mL, 72 mmol) were dissolved in a mixture of dichloromethane (100 mL) and DMF (20 mL) and stirred at r.t. o.n. The homogeneous reaction mixture was washed with water and sat. aq. NaCl solution, then dried over anhydrous sodium sulfate and concentrated under reduced pressure to give crude 50 as a solid. HPLC—(Method B)—t$_r$=5.11 min. [M+H]$^+$=340.2 [M-OH]$^+$, [M]$^-$=356.13 (84%); 4=5.31 min. [M+H]$^+$=358.19, [M]$^-$=356.13 (16%)

A portion of crude 50 was purified by radial chromatography on silica gel, eluting with 2% MeOH in dichloromethane. Two bands were collected but only the more polar band gave sufficient material for analysis. HPLC—(Method B)—t$_r$=5.06 min. [M-OH]$^+$=340.24, [M]$^-$=356.13 (84%). From the predominant loss of H$_2$O in the positive ion ESMS and the nmr spectra, it was concluded that the major species present in crude 50 was the hemiaminal as shown. $^1$H-NMR (300 MHz, DMSO-d$_6$): δ=10.80 (s, 1H, NH), 7.55 (d, J=7.7 Hz, 1H), 7.31 (d, J=8.0 Hz, 1H), 7.15 (d, J=2.2 Hz, 1H, indole-2H), 7.05 (t, J=7.6 Hz, 1H), 6.97 (t, J=7.6 Hz, 1H), 5.94 (s, 1H), 4.51-4.75 (m, 2H, CH$_2$NO$_2$), 3.30-3.86 (m, 2H), 2.91-3.00 (m, 2H), 2.48-2.56 (m, 1H), 2.15-2.19 (m, 1H), 2.03-2.10 (m, 1H), 1.92-2.00 (m, 1H), 1.85-1.91 (m, 1H), 1.70-1.84 (m, 1H), 1.27 (t, J=12.1 Hz, 1H), 0.83 (d, J=6.0 Hz, 3H, CH$_3$). $^{13}$C-NMR (75 MHz, DMSO-d$_6$): δ=172.7 (CO), 136.9 (C), 127.9 (C), 123.3 (CH), 121.7 (CH), 119.0 (CH), 112.6 (CH), 112.1 (C), 98.5 (C, assigned to C-7), 78.6 (CH$_2$NO$_2$), 52.4 (CH), 49.9 (CH), 47.4 (CH$_2$), 36.8 (CH), 35.8 (CH$_2$), 25.2 (CH$_2$), 17.4 (2-CH$_3$). No resonances greater than 172 ppm corresponding to a ketone carbonyl were observed.

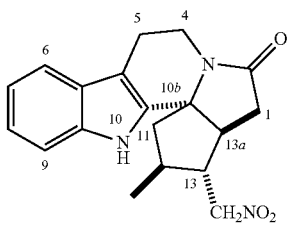

62

4H-Cyclopent[1,8a]indolizino[8,7-b]indole-13-nitromethyl, 1,2,5,10,11,12,13,13a-octahydro-12-methyl-2-oxo-(10bR,12S,13R,13aS)

Crude 50 (14 mmol) was stirred with 5% TFA in dichloromethane at r.t. for 3.5 h. The reaction mixture was concentrated under reduced pressure. The residue was dissolved in dichloromethane, washed once with water and sat aq. NaHCO$_3$ solution, dried with anhydrous sodium sulfate and concentrated under reduced pressure. The crude product was purified by flash column chromatography on silica gel, eluting with 2% MeOH in dichloromethane to yield 62, 4.10 g (86%) as a beige foam. HPLC—(Method B)—t$_r$=5.92 min. (91%, [M+H]$^+$=340.26). An analytical sample was obtained by re-purification of this material on silica gel, eluting 1-2% MeOH in dichloromethane. HPLC—(Method A)—t$_r$=1.91 min. $^1$H-NMR (300 MHz, CDCl$_3$): δ=7.95 (broad s, 1H, NH), 7.45 (d, J=7.6 Hz, 1H), 7.33 (d, J=7.9 Hz, 1H), 7.18 (t, J=7.5 Hz, 1H), 7.11 (t, J=7.5 Hz, 1H), 4.58-4.71 (m, 2H, CH$_2$NO$_2$), 4.46-4.51 (m, 1H, H-4b), 3.08-3.14 (m, 1H, H-5b), 2.93-3.00 (m, 1H, H-40, 2.83-2.91 (m, 1H, H-13a), 2.64-2.74 (m, 2H, H-1b and H-5a), 2.46-2.53 (dd, J=13.1, 6.9 Hz, 1H, H-11b), 2.32-2.39 (dd, J=17.7, 2.5 Hz, 1H, H-1a), 2.22-2.30 (m, 1H, H-12), 2.08-2.20 (m, 1H, H-13), 1.85-1.94 (m, 1H, H-11a), 1.13 (d, J=6.5 Hz, 3H, 12-CH$_3$). $^{13}$C-NMR (75 MHz, CDCl$_3$): δ=173.1 (CO), 136.4 (two non-protonated carbons overlap), 126.7 (C), 122.3 (CH), 119.9 (CH), 118.3 (CH), 111.2 (CH), 107.6 (C), 76.8 (CH$_2$NO$_2$), 69.1 (C-10b), 52.8 (CH), 49.0 (CH$_2$), 45.3 (CH), 37.7 (CH), 36.8 (2 CH$_2$ overlap), 20.5 (CH$_2$), 17.5 (12-CH$_3$). $^{13}$C-NMR (75 MHz, DMSO-d$_6$): δ=172.7 (CO), 138.1 (C), 136.6 (C), 126.8 (C), 121.7 (CH), 119.2 (CH), 118.3 (CH), 111.7 (CH), 106.2 (C), 78.5 (CH$_2$NO$_2$), 69.0 (C-10b), 52.6 (CH), 49.0 (CH$_2$), 45.8 (CH), 37.4 (CH), 36.6 (CH$_2$), 36.3 (CH$_2$), 20.5 (CH$_2$), 17.7 (12-CH$_3$). The overlapping sets of resonances in the CDCl$_3$ spectrum at 136.4 and 36.8 ppm are resolved in DMSO-d$_6$. MS (ES): C$_{19}$H$_{21}$N$_3$O$_3$. Calc.: 340.1661 [M+H]$^+$. Found: 340.1651 [M+H]$^+$ An equal portion of crude 50 (14 mmol) was refluxed in toluene (150 mL) with p-toluenesulfonic acid monohydrate (500 mg) with a Dean-Stark trap. After 3.5 h the reaction mixture was concentrated under reduced pressure. The residue was dissolved in dichloromethane, washed once with water and sat aq. NaHCO$_3$ solution, dried with anhydrous sodium sulfate and concentrated under reduced pressure. The crude product was purified by flash column chromatography on silica gel, eluting with 2% methanol in dichloromethane to yield 62, 3.48 g (73%) as a beige foam. HPLC—(Method B)—t$_r$=5.92 min. (93%, [M+H]$^+$=340.26).

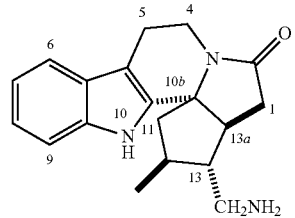

153

4H-Cyclopent[1,8a]indolizino[8,7-b]indole-13-aminomethyl, 1,2,5,10,11,12,13,13a-octahydro-12-methyl-2-oxo-(10bR,12S,13R,13aS)

Compound 62 (2.5 g, 7.4 mmol) was dissolved in methanol (100 mL) and treated with ammonium formate (3.7 g, 58 mmol) and 10% Pd/C (5.0 g), The mixture was heated at 75° C. for 4 h. The mixture was filtered hot over Celite and the cake was washed with hot MeOH. The filtrate was concentrated under reduced pressure. The residue was dissolved in a mixture of EtOAc and MeOH and washed three times with small portions of sat. aq. NaCl. The organic layer was dried over anhydrous sodium sulfate and concentrated under reduced pressure, to give 153, 2.09 g (93%) as a white foam. HPLC—(Method A)—t$_r$=1.26 min. (Method B)—t$_r$=2.83 min (93%).

$[α]_D^{23}$=+124.9 (c=1.02, CHCl$_3$)

$^1$H-NMR (300 MHz, CDCl$_3$): δ=10.10 (s, 1H, indole-NH), 7.44 (d, J=8.2 Hz, 1H), 7.28 (d, J=8.2 Hz, 1H), 7.04-7.26 (m, 2H), 4.45-4.52 (m, 1H), 3.08-3.16 (m, 1H), 3.01 (m, 2H), 2.85-2.97 (m, 1H), 2.70-2.85 (m, 3H), 2.38-2.69 (m, 3H), 1.99 (broad s, 2H), 1.72-1.82 (m, 1H), 1.60-1.62 (m, 1H), 1.10 (d, J=6.1 Hz, 3H, 12-CH$_3$). $^{13}$C-NMR (75 MHz, CDCl$_3$): δ=172.4 (CO), 138.7 (C), 136.3 (C), 126.6 (C), 121.6 (C), 119.4 (CH), 118.2 (CH), 111.2 (CH), 105.9 (CH), 69.5 (C-10b), 55.9 (CH), 48.9 (CH$_2$), 44.6 (CH), 40.8 (CH$_2$), 39.2 (CH$_2$), 36.4 (CH$_2$), 35.7 (CH), 20.8 (CH$_2$), 18.5 (CH$_3$). MS (ES): C$_{19}$H$_{23}$N$_3$O. Calc.: 310.1919 [M+H]$^+$. Found: 310.1916 [M+H]$^+$.

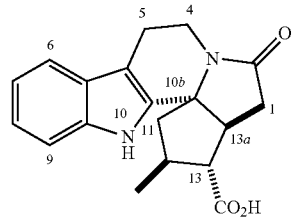

138

4H-Cyclopent[1,8a]indolizino[8,7-b]indole-13-carboxylic acid, 1,2,5,10,11,12,13,13a-octahydro-12-methyl-2-oxo-(10bR,12S,13R,13aS)

Compound 153 (1.0 g, 2.1 mmol) in a mixture of THF/MeOH (⅓, 32 mL) with Cs$_2$CO$_3$ (4.07 g, 6 eq.) was heated at 90° C. in a sealed tube for 21 h. The reaction mixture was cooled to r.t. and then poured into ice-water. The mixture was extracted with Et$_2$O and then acidified with conc. HCl. The aqueous layer was extracted twice with a mixture of EtOAc and MeOH, dried over anhydrous sodium sulfate and concentrated under reduced pressure. The residue was purified by flash chromatography on silica gel, eluting with 5% MeOH in dichloromethane to give 138 as a tan foam, 0.24 g (36%). HPLC—(Method A)—t$_r$=1.65 min. (Method B)—t$_r$=5.13 min (96%). $^1$H-NMR (300 MHz, CDCl$_3$, 60° C.): δ=8.80 (s, 1H, NH), 7.42 (d, J=7.9 Hz, 1H), 7.27 (d, J=7.9 Hz, 1H), 7.08-7.15 (m, 2H), 4.49-4.56 (m, 1H, H-4b), 3.13-3.19 (m, 2H, H-5b and H-13a), 2.89-2.95 (m, 1H, H-4a), 2.80-2.88 (m, 1H, H-1b), 2.68-2.80 (m, 2H, H-5a and H-12), 2.62-2.68 (m, 1H, H-1a), 2.45-2.60 (m, 2H, H-13 and H-11b), 1.90-1.98 (dd, J=13.5, 8.0 Hz, 1H, H-11a), 1.24 (d, J=6.5 Hz, 3H, 12-CH$_3$). $^{13}$C-NMR (75 MHz, CDCl$_3$/CD$_3$OD): δ=177.2 (CO), 174.5 (CO), 136.8 (C), 136.4 (C), 126.6 (C), 121.9 (CH), 119.4 (CH), 118.0 (CH), 111.4 (CH), 100.7 (C), 71.1 (C-10b), 59.1 (CH), 48.0 (CH$_2$), 45.8 (CH), 38.9 (CH), 37.1 (2CH$_2$), 20.5 (CH$_2$), 18.2 (12-CH$_3$). MS (ES): C$_{19}$H$_{20}$N$_2$O$_3$. Calc.: 325.1552 [M+H]$^+$. Found: 325.1541 [M+H]$^+$.

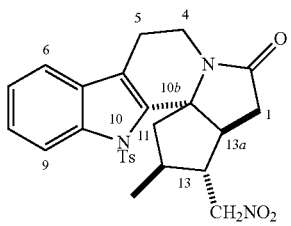

134

Compound 134—Compound 16 (9.25 g, 43 mmol), N-1-Tosyl tryptamine (10.7 g, 43 mmol), EDC (8.25 g, 43 mmol), HOBt (5.4 g, 43 mmol) and triethylamine (14 mL, 0.10 mol) were dissolved in dichloromethane (100 mL) and stirred at r.t. overnight. The reaction mixture was washed with water, 5% aq. citric acid solution, sat. aq. NaHCO$_3$ solution and sat. aq. NaCl solution, then dried over anhydrous sodium sulfate and concentrated under reduced pressure. The crude residue was treated with 5% TFA in dichloromethane (100 mL) at r.t. for 5 h. The reaction mixture was concentrated under reduced pressure. The residue was dissolved in dichloromethane, washed with 1M aq. K$_2$CO$_3$ solution, dried over anhydrous sodium sulfate and concentrated under reduced pressure. The residue was purified by flash chromatography on silica gel, eluting with 1% MeOH in dichloromethane to give 134 as a light yellow foam, 10.8 (51%). (88% HPLC purity). An analytical sample was prepared by radial chromatography on silica gel, eluting with 2% MeOH in dichloromethane. HPLC—(Method A)—t$_r$=2.26 min. (Method B)—t$_r$=7.24 min (97%). $^1$H-NMR (300 MHz, CDCl$_3$): δ=8.00 (d, J=8.0 Hz, 1H), 7.34-7.37 (m, 3H), 7.25-7.29 (m, 2H), 7.19 (d, J=8.5 Hz, 2H), 4.52-4.58 (m, 2H, CH$_2$NO$_2$), 4.30-4.35 (m, 1H, H-4b), 3.50-3.52 (m, 1H, H-13a), 3.09-3.14 (m, 1H, H-4a), 3.00-3.09 (m, 1H, H-5b), 2.75-2.83 (dd, J=14.0, 9.9 Hz, H-11b), 2.60-2.65 (m, 1H, H-5a), 2.50-2.60 (m, 1H, H-12), 2.34 (s, 3H, Ts-CH$_3$), 2.28-2.30 (m, 1H, H-13), 2.12-2.16 (m, 2H, H1a and H1b), 1.84-1.92 (dd, J=14.0, 7.7 Hz, H-11a), 1.09 (d, J=6.6 Hz, 3H, 12-CH$_3$). $^{13}$C-NMR (75 MHz, CDCl$_3$): δ=174.9 (CO), 145.3 (C), 137.7 (C), 136.8 (C), 136.6 (C), 130.3 (CH), 129.0 (CH), 126.0 (C), 125.8 (CH), 124.3 (CH), 121.1 (CH), 119.0 (CH), 115.5 (CH), 78.8 (CH$_2$NO$_2$), 73.9 (C-10b), 52.8 (CH), 47.2 (CH$_2$), 47.0 (CH$_2$), 37.5 (CH), 35.8 (CH$_2$), 35.0 (CH$_2$), 21.8 (Ts-CH$_3$), 21.1 (CH$_2$), 20.4 (12-CH$_3$). MS (ES): C$_{26}$H$_{27}$N$_3$O$_5$S. Calc.: 494.1750 [M+H]$^+$. Found: 494.1697 [M+H]$^+$.

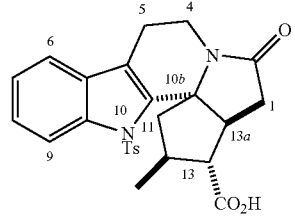

136

Compound 136—Compound 134 (2.89 g, 6.0 mmol) was dissolved in DMF (50 mL) and treated with NaNO$_2$ (2.42 g, 36 mmol) and HOAc (7.2 g, 0.116 mol). The reaction mixture was heated at 50° C. for 5 h. The reaction mixture was poured onto ice and carefully neutralized with solid NaHCO$_3$. The mixture was extracted with Et$_2$O and then acidified with concentrated HCl. The aqueous layer was extracted twice with a mixture of EtOAc and MeOH. The combined organic layers were extracted 9 times with sat. aq. NaCl solution. The organic layer was dried over anhydrous sodium sulfate and concentrated under reduced pressure to give 136 as an orange foam, 2.57 g (89%). HPLC—(Method B)—t$_r$=6.34 min (95%). An analytical sample was prepared by hplc. HPLC—(Method A)—t$_r$=2.07 min. $^1$H-NMR (300 MHz, CDCl$_3$): δ=8.06 (d, J=7.6 Hz, 1H), 7.44 (d, J=8.2 Hz, 2H), 7.32-7.36 (m, 1H), 7.26-7.32 (m, 2H), 7.17 (d, J=8.2 Hz, 2H), 4.29-4.33 (m, 1H, H-4b), 3.88-3.95 (m, 1H, H-13a), 3.00-3.14 (m, 3H, H-12, H-4a, H-5b), 2.73-2.82 (m, 1H, H-11b), 2.60-2.65 (m, 1H, H-5a), 2.48-2.52 (m, 1H, H-1b), 2.35-2.45 (m, 1H, H-13), 2.32 (s, 3H, Ts-CH$_3$), 2.10-2.19 (dd, J=17.6, 7.6 Hz, 1H, H-1a), 1.80-1.87 (dd, J=14.0, 8.8 Hz, 1H, H-11a), 1.17 (d, J=6.4 Hz, 3H, 12-CH$_3$). $^{13}$C-NMR (75 MHz, CDCl$_3$): δ=178.8 (CO), 175.4 (CO), 144.9 (C), 137.5 (C), 136.7 (C), 136.3 (C), 130.0 (CH), 128.8 (CH), 125.7 (CH and C: in DMSO-d$_6$ these two carbons are observed at 126.37 and 126.22 ppm), 123.9 (CH), 120.7 (C), 118.7 (CH), 115.3 (CH), 73.5 (C-10b), 58.2 (CH), 47.0 (CH$_2$), 46.2 (CH), 36.9 (CH), 35.5 (CH$_2$), 34.7 (CH$_2$), 21.5 (Ts-CH$_3$), 21.0 (CH$_2$), 20.2 (12-CH$_3$). MS (ES): C$_{27}$H$_{26}$N$_2$O$_5$S. Calc.: 479.1641 [M+H]$^+$. Found: 479.1666 [M+H]$^+$.

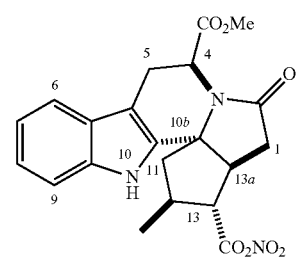

64

4H-Cyclopent[1,8a]indole-4-carboxylic acid, 1,2,5,10,11,12,13,13a-octahydro-12-methyl-13-nitromethyl,-2-oxo-Methyl ester (10bR,12S,13R,13aS)

Compound 16 (4.30 g, 20 mmol), L-tryptophan methyl ester hydrochloride (5.10 g, 20 mmol), EDC (3.9 g, 20 mmol), HOBt (2.7 g, 20 mmol) and triethylamine (11 mL, 79 mmol) were dissolved in dichloromethane (100 mL) and stirred at r.t. o.n. The reaction mixture was washed with water, 10% HCl, sat. aq. NaHCO$_3$ solution and sat. aq. NaCl solution, then dried over anhydrous sodium sulfate and concentrated under reduced pressure. The crude residue was treated with 5% TFA in dichloromethane (100 mL) at r.t. for 5 h. The reaction mixture was concentrated under reduced pressure. The residue was dissolved in dichloromethane, washed with sat. aq. NaHCO$_3$ solution, dried over anhydrous sodium sulfate and concentrated under reduced pressure. The residue was purified by flash chromatography on silica gel, eluting with 0.5% MeOH in dichloromethane to give 64 as a white foam, 2.85 g (36%). (98% HPLC purity). Another 400 mg of slightly impure material (92% HPLC) was also obtained. HPLC—(Method A)—$t_r$=1.83 min. (Method B)—$t_r$=5.82 min (98%)

$[\alpha]_D^{24}$=+99.5 (c=0.75, CHCl$_3$)

$^1$H-NMR (300 MHz, CDCl$_3$): δ=9.02 (s, 1H, NH), 7.48 (d, J=7.6 Hz, 1H), 7.31 (m, 1H), 7.10-7.14 (m, 2H), 5.49 (d, J=7.9 Hz, 1H, H-4), 4.58-4.61 (m, 2H, CH$_2$NO$_2$), 3.71 (s, 3H, CO$_2$Me), 3.44 (d, J=16.1 Hz, H-5b), 3.13-3.16 (dd, J=15.9, 7.8 Hz, H-5a), 2.75-2.90 (m, 2H, H-13a and H-1b), 2.45-2.53 (dd, J=17.0, 3.8 Hz, H-1a), 2.05-2.30 (m, 4H, H-11a, H-11b, H-12, H-13), 1.12 (d, J=5.3 Hz, 3H, 12-CH$_3$). $^{13}$C-NMR (75 MHz, CDCl$_3$): δ=173.9 (CO), 171.2 (CO), 136.4 (C), 135.9 (C), 126.4 (C), 122.6 (CH), 120.1 (CH), 118.5 (CH), 111.2 (CH), 105.3 (C), 76.8 (CH$_2$NO$_2$), 68.6 (C-10b), 53.3 (CH), 52.4 (CO$_2$Me), 50.0 (CH), 49.0 (CH$_2$), 46.2 (CH), 38.1 (CH), 37.6 (CH$_2$), 21.6 (CH$_2$), 17.4 (12-CH$_3$). $^1$H-NMR (300 MHz, DMSO-d$_6$,60° C.): δ=10.57 (s, 1H, NH), 7.40 (d, J=7.9 Hz, 1H), 7.34 (d, J=7.9 Hz, 1H), 7.05-7.12 (m, 1H), 6.95-7.02 (m, 1H), 5.28 (dd, J=7.8, 1.4 Hz, 1H, H-4), 4.82-4.89 (m, 2H, CH$_2$NO$_2$), 3.63 (s, 3H, CO$_2$Me), 3.17-3.23 (dd, J=16.1, 1.5 Hz, 1H, H-5b), 2.82-2.90 (dd, J=16.1, 7.5 Hz, 1H, H-5a), 2.65-2.75 (m, 1H, H-13a), 2.55-2.64 (m, 1H, H-1b), 2.33-2.43 (dd, J=17.5, 4.6 Hz, 1H, H-1a), 2.23-2.33 (m, 2H, H-12 and H-13), 1.98-2.02 (dd, J=12.6, 5.5 Hz, 1H, H-11b), 1.88-1.93 (t, J=12.4, 1H, H-11a), 1.02 (d, J=5.9 Hz, 3H, 12-CH$_3$). MS (ES): C$_{21}$H$_{23}$N$_3$O$_5$. Calc.: 398.1716 [M+H]$^+$. Found: 398.1694 [M+H]$^+$.

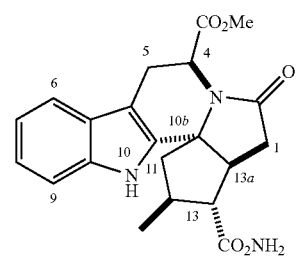

154

4H-Cyclopent[1,8a]indolizino[8,7-b]indole-4-carboxylic acid, 1,2,5,10,11,12,13,13a-octahydro-12-methyl-13-aminomethyl,-2-oxo-Methyl ester (10bR, 12S,13R,13aS)

Compound 64 (3.08 g, 7.7 mmol) was dissolved in methanol (100 mL) and treated with ammonium formate (6 g, 94 mmol) and 10% Pd/C (6 g). The mixture was heated at 80° C. for 3 h. The mixture was filtered hot over Celite and the cake was washed with hot MeOH. The filtrate was concentrated under reduced pressure. The residue was dissolved in a mixture of EtOAc and MeOH and washed with a small portion of sat. aq. NaCl. The organic layer was dried over anhydrous sodium sulfate and concentrated under reduced pressure. The residue was purified by flash chromatography on silica gel, eluting with 5-10% MeOH in dichloromethane to give 154 as a white foam, 1.85 g (65%). HPLC-(Method A)—$t_r$=1.12 min—(Method A)—$t_r$=5.13 min (97%)

$[\alpha]_D^{24}$=+57.6 (c=0.74, CHCl$_3$)

$^1$H-NMR (300 MHz, CDCl$_3$) δ=11.19 (s, 1H, NH), 7.49 (m, 1H), 7.28 (m 1H), 7.08-7.13 (m, 2H), 5.36 (dd, J=8.4, 1.9 Hz, 1H, H-4), 3.72 (s, 3H, CO$_2$Me), 3.44-3.51 (dd, J=16.0, 1.8 Hz, H-5b), 3.06-3.14 (dd, J=16.0, 8.4 Hz, 1H, H-5a), 3.00 (broad s, 2H, CH$_2$NH$_2$), 2.80-2.89 (dd, J=16.5, 10.6 Hz, H-1b), 2.63-2.69 (m, 1H, H-13a), 2.45-2.58 (m, 2H, H-1a, H-12), 2.17-2.23 (dd, J=12.5, 6.2 Hz, H-11b), 1.95-2.04 (t, J=12.6, 1H, H-11a), 1.74 (broad s, 2H, NH$_2$, exchanges with D$_2$O), 1.61 (m, 1H, H-13), 1.09 (d, J=6.4 Hz, 3H, 12-CH$_3$). $^{13}$C-NMR (75 MHz, CDCl$_3$): δ=173.0 (CO), 171.7 (CO), 138.5 (C), 136.4 (C), 126.4 (C), 121.6 (CH), 119.4 (CH), 118.4 (CH), 111.3 (CH), 103.4 (C), 68.6 (C-10b), 55.5 (CH), 52.4 (CO$_2$Me), 49.0 (CH), 48.6 (CH$_2$), 46.0 (CH), 40.4 (CH$_2$), 40.0 (CH$_2$), 35.4 (CH), 21.6 (CH$_2$), 18.6 (12-CH$_3$). MS (ES): C$_{21}$H$_{25}$N$_3$O$_3$. Calc.: 368.1974 [M+H]$^+$. Found: 368.1958 [M+H]$^+$.

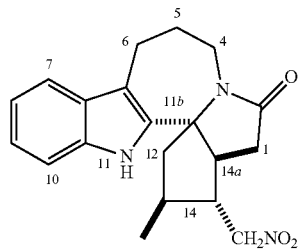

66

Cyclopenta[2',3']pyrrolo[1'2':1,2]azepino[3,4-b]indole-14-nitromethyl, 1,2,5,10,11,12,13,13a-octahydro-13-methyl-2-oxo-, (10bR,12S,13R,13aS)

Compound 16 (4.00 g, 18.5 mmol), 3-(3-aminopropyl) indole (3.6 g, 18.4 mmol), EDC (4.0 g, 20.8 mmol), HOBt (2.8 g, 20.7 mmol) and triethylamine (7.2 mL, 52 mmol) were dissolved in dichloromethane (100 mL) and stirred at r.t. o.n. The reaction mixture was washed with water, 10% HCl, sat. aq. NaHCO$_3$ solution and sat. aq. NaCl solution, then dried over anhydrous sodium sulfate and concentrated under reduced pressure. The crude residue was treated with 5% TFA in dichloromethane (100 mL) at r.t. for 4 h. The reaction mixture was concentrated under reduced pressure. The residue was dissolved in dichloromethane, washed with sat. aq. NaHCO$_3$ solution, dried over anhydrous sodium sulfate and concentrated under reduced pressure. The residue was purified by flash chromatography on silica gel, eluting with 2-5% MeOH in dichloromethane to give 66 as a white foam, 3.06 g (47%). An analytical sample was prepared by hplc. HPLC—(Method A)—$t_r$=1.99 min. (Method B)—$t_r$=6.06 min. $^1$H-NMR (300 MHz, CDCl$_3$): δ=8.05 (s, 1H, NH), 7.45-7.48 (m, 1H), 7.25-7.28 (m, 1H), 7.09-7.14 (m, 2H), 4.58-4.62 (m, 2H, CH$_2$NO$_2$), 4.34-4.40 (m, 1H, H-4b), 3.13-3.18 (m, 1H, H-4a), 2.98-3.05 (m, 1H, H-14a), 2.80-2.88 (m, 2H, H-6a and H-6b), 2.60-2.70 (dd, J=17.6, 8.8 Hz, 1H, H-1b), 2.38-2.46 (dd, 1H, J=17.6, 7.6 Hz, H-12b), 2.25-2.29 (m, 2H, H-13, H-1a), 2.08-2.11 (m, 1H, H-5b), 1.91-2.08 (m, 3H, H-5a, H-12a, and H-14), 1.11 (d, J=6.0 Hz, 3H, 13-CH$_3$). Assignments are tentative, based on the COSY spectrum. $^{13}$C-NMR (75 MHz, CDCl$_3$): δ=173.1 (CO), 137.9 (C), 135.7 (C), 128.4 (C), 122.4 (CH), 119.8 (CH), 118.5 (CH), 113.3 (C), 111.0 (CH), 76.7 (CH$_2$NO$_2$), 72.5 (C-11b), 51.4 (CH), 47.5 (CH), 47.0 (CH$_2$), 40.5 (CH$_2$), 37.9 (CH), 35.0 (CH$_2$), 27.6 (CH$_2$), 22.0 (CH$_2$), 17.9 (13-CH$_3$). MS (ES): C$_{20}$H$_{23}$N$_3$O$_4$. Calc.: 354.1818 [M+H]$^+$. Found: 354.1810 [M+H]$^+$.

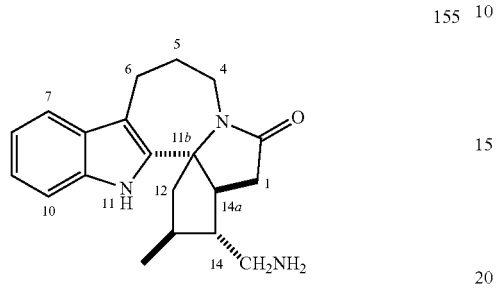

155

Cyclopenta[2',3']pyrrolo[1',2':1,2]azepino[3,4-b]indole-14-aminomethyl, 1,2,5,10,11,12,13,13a-octahydro-13-methyl-2-oxo-, (10bR,12S,13R,13aS)

Compound 66 (2.04 g, 5.7 mmol) was dissolved in methanol (80 mL) and treated with ammonium formate (4.3 g, 67 mmol) and 10% Pd/C (4.05 g). The mixture was heated at 80° C. for 3 h. The mixture was filtered hot over Celite and the cake was washed with hot MeOH. The filtrate was concentrated under reduced pressure. The residue was dissolved in a mixture of EtOAc and MeOH and washed with a small portion of sat. aq. NaCl. The organic layer was dried over anhydrous sodium sulfate and concentrated under reduced pressure. The residue was purified by flash chromatography on silica gel, eluting with 5% MeOH in dichloromethane, then 10% 2M NH$_3$ in MeOH/90% dichloromethane to give 155 as a white foam, 0.52 g (28%). HPLC—(Method A)—t$_r$=1.55 min. (Method B)—t$_r$=3.05 min (92%).

[α]$_D^{24}$+45.6 (c=0.61 CHCl$_3$)

$^1$H-NMR (300 MHz, CDCl$_3$, 60° C.): δ=10.44 (broad s, 1H, NH), 7.46 (m, 1H), 7.25-7.30 (m, 1H), 7.02-7.07 (m, 2H), 4.33-4.42 (m, H-4b), 3.22 (broad s, 2H), 3.02-3.23 (m, 3H), 2.80-3.00 (m, 3H), 2.64-2.73 (m, 1H), 2.20-2.36 (m, 3H), 1.97-2.07 (m, 2H), 1.71-1.78 (m, 1H), 1.39-1.45 (m, 1H), 0.99 (d, J=6.1 Hz, 3H, 13-CH$_3$). $^{13}$C-NMR (75 MHz, CDCl$_3$, 60° C.): δ=173.1 (CO), 139.8 (C), 135.3 (C), 128.3 (C), 121.4 (CH), 119.0 (CH), 118.1 (CH), 111.4 (CH), 110.8 (C), 73.0 (C-11b), 55.6 (CH), 48.2 (CH$_2$), 45.6 (CH), 41.5 (CH$_2$), 40.7 (CH$_2$), 37.2 (CH$_2$). 35.4 (CH), 27.8 (CH$_2$), 22.9 (CH$_2$), 18.1 (13-CH$_3$). MS (ES): C$_{20}$H$_{25}$N$_3$O. Calc.: 324.2076 [M+H]$^+$. Found: 324.2086 [M+H]$^+$.

General Procedure for Compounds 96-108

Compound 151 (800 mg, 2.4 mmol) was dissolved in a mixture of dichloromethane (15 mL) and THF (5 mL) and 1.3 mL (0.156 mmol) of this stock solution was aliquoted to seven glass vials. The appropriate amine (0.2 mmol) was added to each vial, followed by 1.0 mL of a stock solution prepared from 1-hydroxy-7-azabenzotriazole (1.22 g, 9 mmol), EDC (1.72 g, 9 mmol) and Et$_3$N (3.8 mL, 27 mmol) in dry dichloromethane (45 mL). The vials were shaken at r.t. for 48 h. The mixtures were diluted with dichloromethane and washed either with sat. aq. NaCl solution or 10% HCl as appropriate. After concentration under reduced pressure, the crude residues were purified by C-18 rp-HPLC to give 96-108 in the yields indicated.

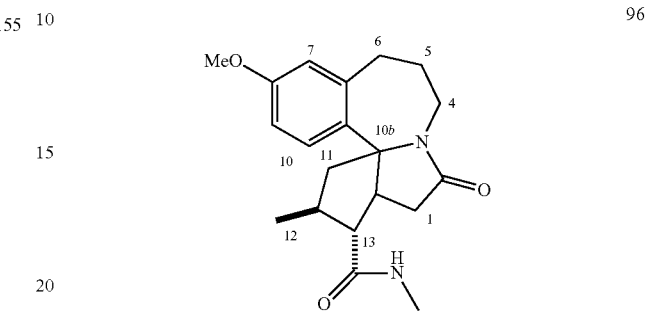

96

Compound 96 (white solid, 39.9 mg, 75%). HPLC—(Method A)—t$_r$=1.52 min. $^1$H-NMR (300 MHz, CDCl$_3$): δ=7.36 (d, J=8.5 Hz, 1H, H-10), 6.80 (broad s, 1H, NH), 6.72 (dd, J=8.5, 2.3 Hz, 1H, H-9), 6.56 (d, J=2.2 Hz, 1H, H-7), 4.22-4.27 (m, 1H, H-4b), 3.76 (s, 3H, OMe), 3.27-3.31 (m, 1H), 3.10-3.14 (m, 1H), 2.82 (d, J=4.7 Hz, NHCH$_3$), 2.70-2.80 (m, 3H), 2.45 (dd, J=17.0, 7.7 Hz, 1H), 2.12-2.29 (m, 2H), 1.92-2.02 (m, 3H), 1.75-1.85 (m, 1H), 1.04 (d, J=6.0 Hz, 3H, 12-CH$_3$). $^{13}$C-NMR (75 MHz, CDCl$_3$): δ=173.5 (2 CO), 158.2, 141.7, 136.3, 128.0, 116.6, 111.7, 76.3 (C-10b), 60.0, 55.4, 51.9, 47.4, 39.6, 38.9, 34.4, 33.7, 26.6, 18.5 (12-CH$_3$). MS (ES): C$_{20}$H$_{26}$N$_2$O$_3$. Calc.: 343.2022 [M+H]$^+$. Found: 343.2032 [M+H]$^+$.

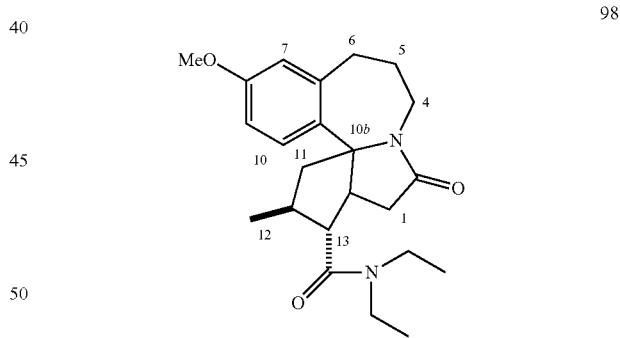

98

Compound 98 (white solid, 44.6 mg, 74%). HPLC—(Method A)—t$_r$=2.00 min. $^1$H-NMR (300 MHz, CDCl$_3$): δ=7.43 (d, J=8.5 Hz, 1H, H-10), 6.71 (dd, J=8.7, 2.6 Hz, 1H, H-9), 6.56 (d, J=2.6 Hz, 1H, H-7), 4.22-4.40 (m, 1H, H-4b), 3.76 (s, 3H, OMe), 3.35-3.52 (m, 5H, 2 NCH$_2$CH$_3$ and 1H), 3.05-3.15 (m, 1H), 2.70-2.80 (m, 3H), 2.45-2.57 (m, 2H), 2.24-2.31 (dd, J=13.5, 7.7 Hz, 1H), 1.96-2.13 (m, 3H), 1.75-1.85 (m, 1H), 1.15-1.21 (m, 6H, 2 NCH$_2$CH$_3$), 1.03 (d, J=6.6 Hz, 3H, 12-CH$_3$). $^{13}$C-NMR (75 MHz, CDCl$_3$): δ=173.4 (CO), 172.6 (CO), 158.1, 141.7, 136.5, 128.2, 116.4, 111.7, 76.2 (C-10b), 55.4, 53.7, 52.9, 47.6, 42.2, 41.1, 38.9, 34.4, 33.7, 26.7, 18.5, 15.6, 13.4. MS (ES): C$_{23}$H$_{32}$N$_2$O$_3$. Calc.: 385.2491 [M+H]$^+$. Found: 385.2493 [M+H]$^+$.

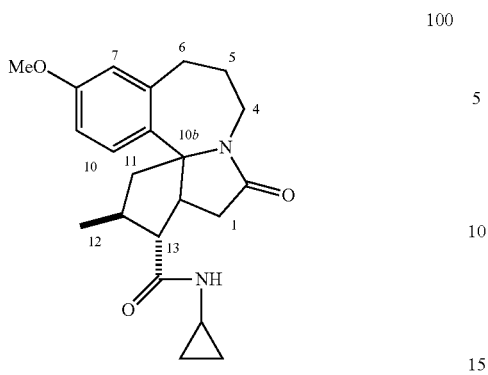

Compound 100 (white solid, 42.7 mg, 74%). HPLC—(Method A)—$t_r$=1.72 min. $^1$H-NMR (300 MHz, CDCl$_3$): δ=7.36 (d, J=8.8 Hz, 1H, H-10), 6.92 (d, J=3.0 Hz, 1H, NH), 6.72 (dd, J=8.5, 2.7 Hz, 1H, H-9), 6.56 (d, J=2.7 Hz, 1H, H-7), 4.18-4.25 (m, 1H, H-4b), 3.76 (s, 3H, OMe), 3.27-3.33 (m, 1H), 3.05-3.10 (m, 1H), 2.72-2.82 (m, 4H), 2.41-2.50 (dd, J=17.0, 7.7 Hz, 1H), 2.21-2.29 (dd, J=13.6, 8.1 Hz, 1H), 2.13 (d, J=17.0 Hz, 1H), 1.88-1.98 (m, 3H), 1.75-1.85 (m, 1H), 1.03 (d, J=6.6 Hz, 3H, 12-CH$_3$), 0.74-0.78 (m, 2H, CH$_2$-cyclopropyl), 0.47-0.50 (m, 2H, CH$_2$-cyclopropyl). $^{13}$C-NMR (75 MHz, CDCl$_3$): δ=173.9 (CO), 173.0 (CO), 157.8, 141.3, 135.9, 127.7, 116.3, 111.5, 76.1 (C-10b), 59.4, 55.3, 51.8, 47.3, 42.8, 39.4, 38.7, 34.2, 33.5, 26.5, 22.9, 18.4 (12-CH$_3$), 6.7 (2-cyclopropyl CH$_2$). MS (ES): C$_{22}$H$_{28}$N$_2$O$_3$. Calc.: 369.2178 [M+H]$^+$. Found: 369.2187 [M+H]$^+$.

Compound 104 (white solid, 31.3 mg, 55%). HPLC—(Method A)—$t_r$=1.73 min. $^1$H-NMR (300 MHz, CDCl$_3$): δ=8.42 (broadened t, 1H, NH), 7.33 (d, J=8.8 Hz, 1H, H-10), 6.74 (dd, J=8.7, 2.7 Hz, 1H, H-9), 6.59 (d, J=2.5 Hz, 1H, H-7), 4.22-4.26 (m, 1H, H-4b), 4.15-4.20 (m, 2H, α-CH$_2$), 3.77 (s, 3H, OMe), 3.24-3.28 (m, 1H), 3.15-3.20 (m, 1H), 2.70-2.77 (m, 3H), 2.50-2.54 (dd, J=17.0, 7.7 Hz, 1H), 2.25-2.33 (m, 1H), 2.09-2.20 (m, 1H), 1.97-2.20 (m, 3H), 1.80-1.85 (m, 1H), 1.08 (d, J=6.3 Hz, 3H, 12-CH$_3$). $^{13}$C-NMR (75 MHz, CDCl$_3$): δ=173.6 (CO), 173.5 (CO), 158.3, 141.6, 135.7, 127.9, 116.7, 116.5, 111.9, 76.7 (C-10b), 59.0, 55.5, 52.2, 47.4, 39.7, 39.0, 34.4, 33.6, 27.6, 26.6, 18.4 (12-CH$_3$). MS (ES): C$_{21}$H$_{25}$N$_3$O$_3$. Calc.: 368.1974 [M+H]$^+$. Found: 368.1997 [M+H]$^+$.

Compound 102 (white solid, 44.6 mg, 64%). HPLC—(Method A)—$t_r$=1.72 min. $^1$H-NMR (300 MHz, CDCl$_3$): δ=7.37 (s, 1H, NH), 7.33 (d, J=8.5 Hz, 1H, H-10), 6.72 (dd, J=8.6, 2.5 Hz, 1H, H-9), 6.55 (d, J=2.5 Hz, 1H, H-7), 4.65-4.69 (dd, J=9.0, 2.5 Hz, 1H, H-α), 4.24-4.34 (m, 2H, H-β and H-4b), 3.76 (s, 3H, OMe), 3.26-3.31 (m, 1H), 3.10-3.16 (m, 1H), 2.70-2.75 (m, 3H), 2.47-2.50 (dd, J=17.4, 7.4 Hz, 1H), 2.30-2.41 (m, 1H), 2.10-2.18 (t, J=10.8 Hz, 1H), 1.99-2.05 (m, 2H), 1.79-1.90 (m, 1H), 1.21 (d, J=6.3 Hz, 3H, CH(OH)CH$_3$), 1.11 (d, J=6.3 Hz, 12-CH$_3$). $^{13}$C-NMR (75 MHz, CDCl$_3$): δ=174.1 (CO), 173.5 (CO), 171.6 (CO), 158.2, 141.6, 136.0, 128.0, 116.6, 111.9, 76.8 (C-10b), 68.1, 60.0, 58.1, 55.4, 52.7, 52.3, 47.7, 39.8, 39.0, 34.3, 33.5, 26.5, 20.5, 18.5 (12-CH$_3$). MS (ES): C$_{24}$H$_{32}$N$_2$O$_6$. Calc.: 445.2339 [M+H]$^+$. Found: 445.2357 [M+H]$^+$.

Compound 106 (oil, 54.5 mg, 69%). HPLC—(Method A)—$t_r$=2.40 min. $^1$H-NMR (300 MHz, CDCl$_3$): δ=7.41 (d, J=8.6 Hz, 1H, H-10), 7.14-7.18 (m, 1H), 6.74 (dd, J=8.5, 2.8 Hz, 1H, H-9), 6.57 (d, J=2.8 Hz, H-7), 6.44-6.54 (m, 3H), 4.25-4.30 (m, 1H, H-4b), 3.79 (s, 3H, OMe), 3.76 (s, 3H, OMe), 3.70-4.00 (m, 4H), 3.46-3.52 (t, J=8.5 Hz, 1H), 3.11-3.20 (m, 6H), 2.65-2.75 (m, 3H), 2.46-2.57 (dd, J=17.0, 8.0 Hz, 1H), 2.27-2.34 (dd, J=13.6, 7.3 Hz, 1H), 1.98-2.08 (m, 3H), 1.80-1.85 (m, 1H), 1.05 (d, J=6.0 Hz, 3H, 12-CH$_3$). $^{13}$C-NMR (75 MHz, CDCl$_3$): δ=173.4 (CO), 172.1 (CO), 160.9, 158.2, 152.2, 141.8, 136.3, 130.2, 128.1, 116.5, 111.8, 109.5, 105.7, 103.4, 76.3 (C-10b), 55.5, 55.4, 53.4, 52.7, 50.4, 49.9, 47.6, 46.1, 42.5, 41.0, 38.9, 34.6, 33.7, 26.7, 18.7 (12-CH$_3$). MS (ES): C$_{30}$H$_{37}$N$_3$O$_4$. Calc.: 504.2862 [M+H]$^+$. Found: 504.2820 [M+H]$^+$.

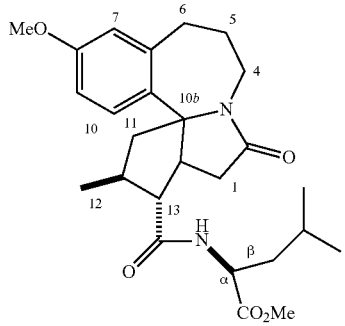

Compound 108 (white solid, 42.5 mg, 60%). HPLC—(Method A)—$t_r$=2.24 min. $^1$H-NMR (300 MHz, CDCl$_3$): δ=7.34 (d, J=8.8 Hz, 1H, H-10), 6.71 (dd, J=8.8, 2.6 Hz, 1H, H-9), 6.57 (d, J=2.9 Hz, 1H, H-7), 6.49 (d, J=8.3 Hz, 1H, NH), 4.63-4.70 (m, 1H, H-α), 4.23-4.31 (m, 1H, H-4b), 3.76 (s, 3H), 3.74 (s, 3H), 3.28-3.35 (m, 1H), 3.06-3.15 (m, 1H), 2.67-2.77 (m, 3H), 2.45-2.54 (dd, J=17.0, 7.7 Hz, 1H), 2.23-2.30 (dd, J=13.6, 8.1 Hz, 1H), 2.09-2.19 (m, 1H), 1.51-1.70 (m, 3H), 1.95-2.06 (m, 3H), 1.80-1.84 (m, 1H), 1.10 (d, J=6.6 Hz, 3H, 12-CH$_3$), 0.93 (d, J=6.0 Hz, 6H, CH(CH$_3$)$_2$). $^{13}$C-NMR (75 MHz, CDCl$_3$): δ=173.6 (CO), 173.2 (CO), 172.9 (CO), 158.2, 141.8, 136.2, 127.9, 116.6, 111.7, 76.2 (C-10b), 59.8, 55.4, 52.5, 51.9, 51.1, 47.5, 41.5, 39.9, 38.8, 34.3, 33.7, 26.7, 25.2, 23.1, 21.9, 18.4 (12-CH$_3$). MS (ES): C$_{26}$H$_{36}$N$_2$O$_5$. Calc.: 457.2702 [M+H]$^+$. Found: 457.2693 [M+H]$^+$.

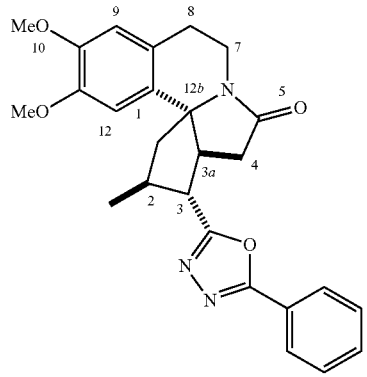

Compound 72. Compound 48 (100 mg, 0.29 mmol) was treated with benzoic hydrazide (1.1 eq., 44 mg), polymer supported triphenylphosphine (570 mg, 3 eq., Polymer Systems 1.52 mmol/g) and dry CH$_3$CN (3 mL). Then Cl$_3$CCN (60 μl, 2 eq.) was added followed by irradiation in the microwave at 150° C. for 20 min. The reaction mixture was filtered and the resin was washed with MeOH. The filtrate was concentrated under reduced pressure and the residue was purified by hplc to give 72 as an oil, 12 mg. HPLC—(Method A)—$t_r$=1.75 min. (Method B)—$t_r$=5.57 min. $^1$H-NMR (300 MHz, CDCl$_3$): δ=8.03-8.08 (m, 2H, Ph), 7.45-7.57 (m, 3H, Ph), 6.86 (s, 1H), 6.56 (s, 1H), 4.25-4.33 (m, 1H), 3.90 (s, 3H, OMe), 3.86 (s, 3H, OMe), 3.32-3.40 (m, 1H), 3.15-3.24 (m, 1H), 2.96-3.09 (m, 2H), 2.75-2.86 (m, 1H, H-2), 2.46-2.72 (m, 3H), 2.39-2.46 (dd, J=13.2, 7.0 Hz, 1H, H-1b), 1.90-1.99 (t, J=11.4 Hz, 1H, H-1a), 1.22 (d, J=6.5 Hz, 3H, 2-CH$_3$). $^{13}$C-NMR (75 MHz, CDCl$_3$): δ=172.2 (CO), 167.2, 165.2, 148.2, 148.1, 133.1, 131.9, 129.2, 128.8, 125.3, 123.7, 111.8, 107.2, 71.3 (C-12b), 56.2, 55.9, 51.4, 51.3, 49.3, 40.3, 36.7, 36.1, 27.0, 18.3 (2-CH$_3$). MS (ES): C$_{26}$H$_{27}$N$_3$O$_4$. Calc.: 446.2080 [M+H]$^+$. Found: 446.2063 [M+H]$^+$.

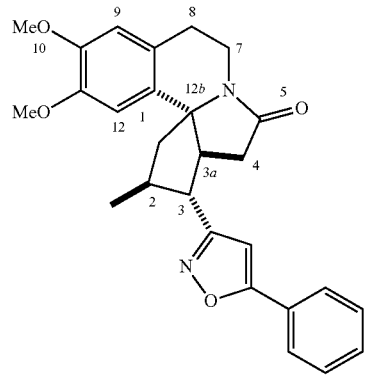

Compound 74—To a solution of phenyl acetylene (305 μL, 5 eq.), DMAP (15 mg), di-t-butyldicarbonate (220 mg, 1 mmol, 1.8 eq.) in dry CH$_3$CN (5 ml) was added 10 (200 mg, 0.56 mmol). The reaction mixture stirred at r.t. overnight whereupon it was concentrated under reduced pressure. The residue was dissolved in dichloromethane, washed with sat. aq. NaCl, dried over anhydrous sodium sulfate and concentrated under vacuum. The crude product was purified by radial chromatography on silica gel, eluting with 1-2% MeOH in dichloromethane to give 74 as a white foam, 74 mg (30%). HPLC—(Method A)—$t_r$=2.03 min. (Method B)—$t_r$=6.47 min (100%). $^1$H-NMR (300 MHz, CDCl$_3$): δ=7.75-7.81 (m, 2H, Ph), 7.44-7.51 (m, 3H, Ph), 6.84 (s, 1H), 6.55 (s, 1H), 6.46 (s, 1H), 4.25-4.31 (m, 1H, H-7b), 3.91 (s, 3H, OMe), 3.85 (s, 3H, OMe), 3.08-3.18 (m, 2H, H-7a and H-8b), 2.98-3.05 (m, 1H, H-3a), 2.77-2.81 (m, 1H, H-3), 2.56-2.68 (m, 3H, H-8a, H-2 and H-4b), 2.35-2.42 (m, 2H, H-4a and H-1b), 1.85-1.93 (t, J=12.8 Hz, 1H, H-1a), 1.12 (d, J=6.1 Hz, 3H, 2-CH$_3$). Assignments are tentative, based on the COSY spectrum. $^{13}$C-NMR (75 MHz, CDCl$_3$): δ=172.6 (CO), 170.3, 164.6, 148.1, 133.8, 130.3, 129.0, 127.3, 125.8, 125.4, 111.7, 107.6, 105.0, 98.5, 71.0 (C-12b), 56.3, 55.9, 52.6, 51.6, 50.2, 41.0, 36.5, 36.0, 27.1, 18.0 (2-CH$_3$). MS (ES): C$_{27}$H$_{28}$N$_2$O$_4$. Calc.: 445.2127 [M+H]$^+$. Found: 445.2122 [M+H]$^+$.

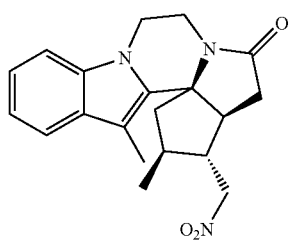

Compound 156—1-(2-Aminoethyl)-3-methylindole (prepared according to the method of Katritzky, J. Org. Chem., 69, 4938 (2003)), 3.7 g (21.2 mMol) and [1S-(1β,2α,3β)-(+)-3-Methyl-2-(nitromethyl)-5-oxocyclopentaneacetic acid, 4.62 g (21.5 mMol) were dissolved in dichloromethane (100 mL) and treated with HOBt (2.70 g, 20 mMol) and EDC hydrochloride (3.92 g, 20 mMol) and triethylamine (5.6 mL, 40 mMol). The reaction mixture was then stirred at room temperature overnight. The reaction mixture was washed sequentially with water, 10% aq. HCl, saturated aq. sodium bicarbonate solution and then dried over anhyd. sodium sulfate and concentrated onto silica gel under vacuum. The residue was purified on the Combiflash system, 220 gm of silica, eluting with hexanes/ethyl acetate.

$^1$H NMR (CDCl$_3$): 7.19 (d, J=7.9, 1H), 6.92 (t, 1H), 6.87 (t, 1H), 6.78 (t, 1H), 6.50 (s, 1H), 4.17-4.26 (m, 1H), 4.06 (dd, J=4.6, 11.7, 1H), 3.90-3.98 (m, 1H), 3.81-3.89 (m, 1H), 3.21-3.27 (m, 1H), 3.09-3.19 (m, 1H), 2.32 (dd, J=17.6, 9.4, 1H), 1.96 (s, 3H), 1.66-1.83 (m, 2H), 1.39-1.48 (m, 2H), 1.05-1.11 (m, 1H), 0.34 (d, J=5.8, 3H), 0.00-0.09 (m, 1H). $^{13}$C NMR (CDCl$_3$): 174.1, 136.5, 128.6, 125.2, 122.0, 119.3, 119.0, 111.2, 109.1, 98.9, 77.6, 52.1, 50.1, 45.5, 42.8, 41.5, 36.3, 35.2, 16.3, 9.51. The lack of a ketone carbonyl indicates that the compound exists as a cyclic hemiketal.

The intermediate amide was dissolved in dry toluene (100 mL), treated with p-toluenesulfonic acid monohydrate (0.40 g) and heated at reflux (135° C. bath) with a Dean Stark trap for 17.5 hours. The reaction mixture was diluted with ethyl acetate, and then washed with saturated aq. sodium bicarbonate solution, dried over anhyd. sodium sulfate and concentrated onto silica gel under vacuum. The residue was purified on the Combiflash system, 220 gm of silica, eluting with hexanes/ethyl acetate to give 156 as a fluffy white solid, 1.90 g.

$^1$H NMR (CDCl$_3$): 7.52 (m, 1H), 7.20 (m, 2H), 7.14 (m, 1H), 4.54-4.69 (AB of ABX, CH$_2$NO$_2$, 2H), 4.44-4.48 (m, 1H), 3.95-4.14 (m, 2H), 3.36-3.44 (m, 1H), 3.22-3.34 (m, 1H), 2.53-2.62 (m, 2H), 2.40-2.44 (m, 1H), 2.36 (s, 3H), 2.15-2.29 (m, 1H), 1.92-2.03 (M, 1H), 1.24-1.29 (m, 1H), 1.15 (d, J=6.4, 3H). $^{13}$C NMR (CDCl$_3$): 172.91, 135.6, 133.6, 128.9, 122.0, 119.8, 118.4, 108.6, 104.3, 77.5, 69.4, 52.4, 49.5, 45.7, 40.3, 38.1, 35.7, 35.3, 18.0, 9.8. HRMS (electrospray): C$_{20}$H$_{23}$N$_3$O$_3$ requires [M+H]$^+$=354.1818. Found: 354.1829.

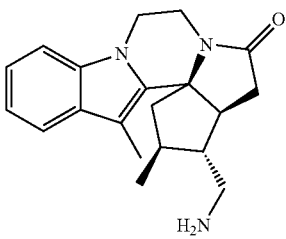

157

Compound 157: 156 (1.60 g) was dissolved in methanol (60 mL) and treated with 10% palladium on carbon (3.30 g) and ammonium formate (2.20 g). The mixture was heated to reflux for 4 hours. After cooling to rt the mixture was filtered over Celite. The filtrate was concentrated under reduced pressure. The residue was dissolved in ethyl acetate, and then washed once with water and twice with saturated aq. sodium chloride solution. The organic layer was dried over anhyd. sodium sulfate and concentrated under vacuum to give 76 as a white foam, 1.89 g. $^1$H NMR (CDCl$_3$): 7.51 (d, J=7.5, 1H), 7.19 (m, 2H), 7.09-7.19 (m, 1H), 4.46 (dd, J=13.2, 5.0, 1H), 3.92-4.14 (m, 3H), 3.34-3.44 (m, 1H), 3.15-3.22 (m, 1H), 2.93-3.10 (m, 2H), 2.56-2.65 (m, 1H), 2.39 (s, 3H), 2.31-2.38 (m, 1H), 1.84-1.92 (m, 1H), 1.51-1.58 (m, 1H), 1.24-1.30 (m, 1H), 1.26 (d, J=5.8, 3H). $^{13}$C NMR (CDCl$_3$): 173.8, 135.3, 134.8, 128.8, 121.6, 119.6, 118.3, 108.5, 104.1, 69.8, 56.7, 50.3, 45.5, 42.8, 40.6, 37.2, 37.0, 35.4, 18.8, 10.1. ESMS: [M+H]$^+$=324. C$_{20}$H$_{25}$N$_3$O=323.

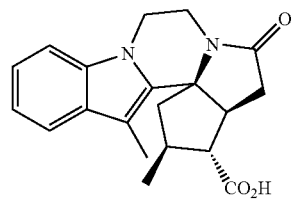

158

Compound 158: 156 (3.04 g, 8.6 mMol) was dissolved in DMF (25 mL) and treated with sodium nitrite (3.56 g, 6 eq.) and acetic acid (10.3 g, 20 eq.). The reaction mixture was then heated at 50° C. for 17 hours. The reaction was poured onto a mixture of ice and water and carefully basified with solid sodium bicarbonate. The mixture was then extracted twice with ether (discarded). The cold aqueous layer was acidified with concentrated hydrochloric acid and extracted thoroughly with a mixture of ethyl acetate and methanol. The organic layers were dried over anhyd. sodium sulfate and concentrated under vacuum. The oily product was then crystallized from dichloromethane/hexanes to give 158 as an orange foam, 1.74 g.

$^1$H NMR (CDCl$_3$): 7.54 (m, 1H), 7.20 (m, 2H), 7.10-7.18 (m, 1H), 4.50 (dd, J=13.2, 5.0, 1H), 4.08-4.14 (m, 1H), 3.93-4.03 (m, 1H), 3.62-3.69 (m, 1H), 3.36-3.47 (m, 1H), 2.82-2.92 (m, 1H), 2.52-2.72 (m, 2H), 2.48 (s, 3H), 2.39-2.48 (m, 2H), 1.90-1.99 (m, 1H), 1.21 (d, J=6.5, 3H). $^{13}$C NMR (CDCl$_3$): 178.0, 173.7, 135.4, 133.4, 128.8, 122.0, 119.8, 118.5, 108.6, 104.8, 70.3, 59.1, 50.0, 46.0, 42.8, 40.6, 38.9, 36.3, 18.7, 10.0. ESMS: [M+H]$^+$=339. C$_{20}$H$_{22}$N$_2$O$_3$=338.

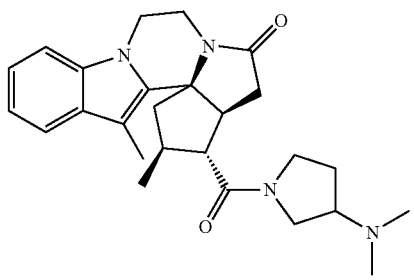

159

Compound 159: A solution of 158 (80 mg, 0.24 mMol) was dissolved in 1 mL of dichloromethane. To this was added 1.1 equivalent of racemic 3-dimethylaminopyrrolidine, triethylamine (110 µl, 3.3 eq.) and 1 mL of a solution of EDC hydrochloride (50 mg, 0.25 mMol) and HOBt (34 mg, 0.25 mMol). The reaction was shaken at rt for 60 hours. The reaction mixture was diluted with dichloromethane, washed with sat. aqueous sodium bicarbonate solution and then concentrated under vacuum. The crude product was purified by preparative HPLC as a mixture of diastereomers.

$^1$H NMR (CDCl$_3$): 7.52 (d, J=7.6, 1H), 7.11-7.16 (m, 2H), 7.07-7.10 (m, 1H), 4.46 (dd, J=13.5, 4.9, 1H), 3.79-4.09 (m, 4H), 3.39-3.58 (m, 4H), 3.11 (m, 1H), 2.89 (m, 1H), 2.56-2.67 (m, 2H), 2.54 (s, 3H), 2.47 (broad s, 3H), 2.46 (broad s, 3H), 2.45-2.50 (m, 2H), 2.20-2.31 (m, 2H), 1.89-1.98 (m, 1H), 1.10 (d, J=6.7, 3H). ESMS: [M+H]$^+$=437. C$_{25}$H$_{37}$N$_4$O$_2$=436.

Biological Assays

In particular disclosed embodiments, a cAMP HTRF assay may be used to test the activity of the compound disclosed herein. The disclosed assay may be used to measure TGR5 activation and therefore may be used to determine the ability of embodiments of the disclosed compound to treat and/or prevent one or more of the diseases/disorders disclosed herein. Methods for conducting the assay are provided below.

Reagents:

The following reagents may be used to conduct the cAMP HTRF assay.

HEK293 TGR5 cell line (Poole et al. *Neurogastroenterol Motil.* 2010 July; 22(7): 814-e228)
LANCE Ultra cAMP kit (Cat # TRF0263, PerkinElmer)
Cell Dissociation Solution (Cat # C5789, Sigma)
IBMX (Cat#15879, Sigma)
OptiPlate-384, White Opaque 384-well Microplate (Cat #6007290, PerkinElmer)
SpectraMax® PARADIGM™ Multimode Microplate Plate Reader (Molecular Devices)

Positive Controls:

In particular disclosed embodiments, a positive control may be used in order to determine the relative activity of the disclosed compound.

TLCA (Cat# L6250, Sigma)
Forskolin (Cat# F3917, Sigma)

Cell Growth:

Cells are grown using the following method.
Cells are grown in DMEM 10% FBS with 100 ug/ml Hygromycin for selection of cAMP vector.
Split cells every other day with trypsin in T175 with a seeding density of 4×E6 in 15 mls.

HTRF Assay:

When cells are 80% confluent, they are washed with PBS and incubated with 3 mls of Cell Dissociation Solution for 5 minutes at room temperature. The cells are then pipetted to get single cell suspension and then neutralized with growth media. The cells are then spun down at 1 k rpm for 10 minutes and washed in PBS. The spinning step is repeated and the cells are resuspended in Stimulation Buffer (DMEM with 0.1% BSA and 0.1 mM IBMX) containing 4× Ulight-anti-cAMP at a density of 500 cells/uL. About 10 ul of cells is added to each well of the 384 well-plate, and about 10 ul of the particular compound is added to each well of the 384 well-plate and incubated for 20 minutes in incubator. The reaction is terminated by adding 20 uL 2× Eu-cAMP in Detection Buffer. The well-plate is then incubated for 20 minutes or overnight. The HTRF signal is then read in SpectraMax Paradigm.

Compound Dilution:

Disclosed embodiments of the compound may be diluted according to the following dilution protocol.
2 ul of 10 mM compound is dissolved in 8 ul DMSO (1:5 dilution)
A 1:3 serial dilution of 4 ul of the compound in 8 ul of DMSO is carried out
The compounds are then diluted 1:100 in Stimulation Buffer (DMEM with 0.1% BSA and 0.1 mM IBMX) and 10 ul is added to the reaction giving a 10 uM final concentration.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a formula

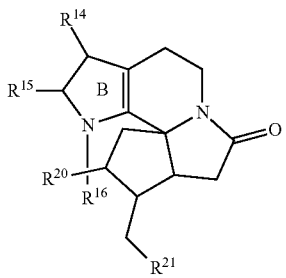

wherein
$R^{14}$ and $R^{15}$ are selected to form, together with the atom to which each is attached, a six-membered aromatic ring;
$R^{16}$ is selected from hydrogen, lower alkyl, or sulfonyl;
$R^{20}$ is lower alkyl; and
$R^{21}$ is selected from lower alkyl, amine, or nitro.

2. The compound according to claim 1 wherein $R^{16}$ is sulfonyl.

3. The compound according to claim 1 wherein $R^{21}$ is nitro.

4. The compound according to claim 1 wherein the compound has a formula

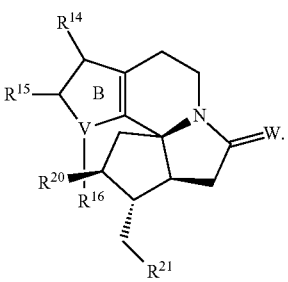

5. The compound according to claim 1 wherein the compound is selected from

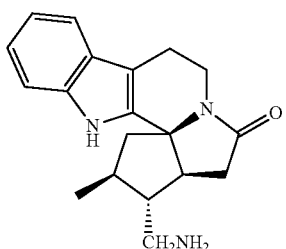

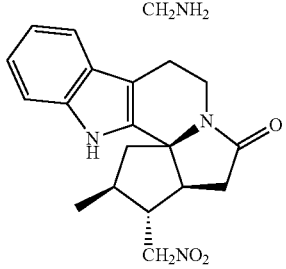

-continued

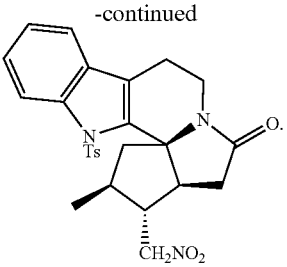

6. The compound according to claim 1 having the structure

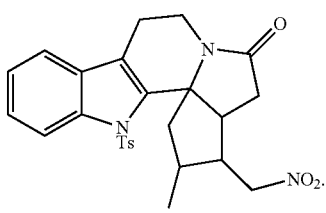 [SMILES: Cc1ccc(S(=O)(=O)n2c3c(c4ccccc42)CCN2C(=O)CC4C(C[N+](=O)[O-])C(C)CC342)cc1]

7. The compound according to claim 6 wherein the compound has a formula

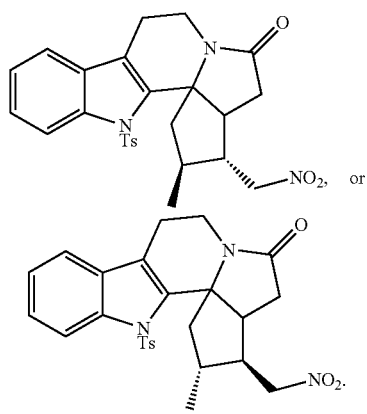

8. A method for making a polycyclic alkaloid, comprising:
providing an aromatic amine compound having a formula

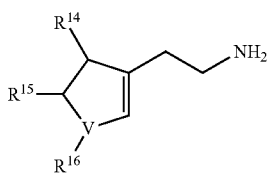

and a carboxylic acid intermediate having a formula

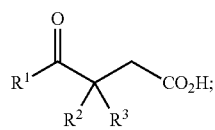

exposing the aromatic amine compound and the carboxylic acid compound to reaction conditions sufficient to form a hemiaminal intermediate having a formula

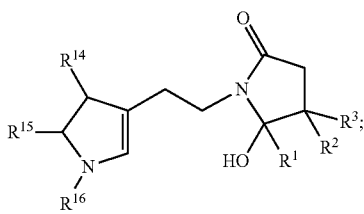

exposing the hemiaminal intermediate to an acid to form a polycyclic alkaloid having a formula

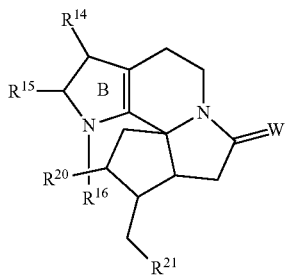

wherein
$R^1$ is bound to either $R^2$ or $R^3$ to form a five-membered cyclic lower alkyl;
$R^2$ and $R^3$ independently are selected from hydrogen or lower alkyl and bound to $R^1$;
$R^{14}$ and $R^{15}$ are selected to form, together with the atom to which each is attached, a six-membered aromatic ring;
$R^{16}$ is selected from hydrogen, lower alkyl, or sulfonyl;
$R^{20}$ is lower alkyl;
$R^{21}$ is selected from lower alkyl, amine, or nitro; and
V is N.

9. The method according to claim 8 wherein the aromatic amine compound is

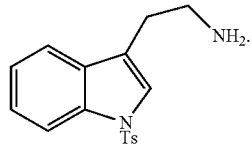 [SMILES: Cc1ccc(S(=O)(=O)n2cc(CCN)c3ccccc32)cc1]

10. The method according to claim 8 wherein the carboxylic acid compound is

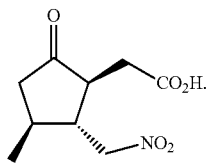

11. The method according to claim 8 wherein the conditions sufficient to form the hemiaminal intermediate comprise one or more activating reagent, a base, and a solvent.

12. The method according to claim 11 wherein the one or more activating reagents are selected from N-ethyl-N'-(3-dimethylaminopropyl)carbodiimide, 1-ethyl-3-(3-dimethylaminopropyl)carbodiimide hydrochloride, dicyclohexylcarbodiimide, carbonyl diimidazole, 1-hydroxybenzotriazole, 1-hydroxy-7-aza-benzotriazole, and o-(7-azabenzotriazol-1-yl)-N,N,N',N'-tetramethyluronium hexafluorophosphate, and any combination thereof, the base is selected from triethylamine, 1,8-diazabicycloundec-7-ene, 1,4-diazabicyclo[2.2.2]octane, and diisopropylethylamine, and the solvent is dichloromethane.

13. The method according to claim 8 wherein the hemi-aminal intermediate is

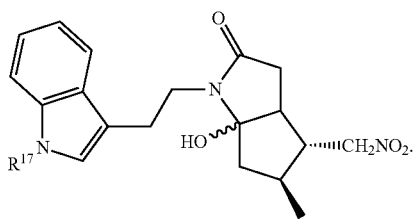

14. The method according to claim 8 wherein the acid is selected from para-toluenesulfonic acid, trifluoroacetic acid, and camphorsulfonic acid.

15. The method according to claim 8 wherein the polycyclic alkaloid is selected from

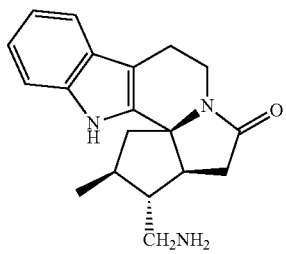

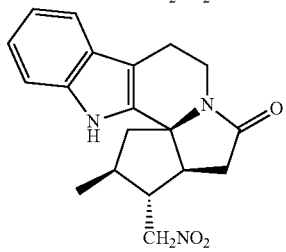

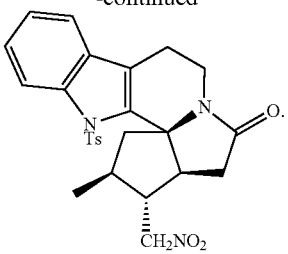

16. A pharmaceutical composition, comprising an effective amount of a compound of formula I according to claim 1, or a pharmaceutically acceptable salt thereof, and a pharmaceutically acceptable carrier, diluent or excipient.

17. A compound selected from

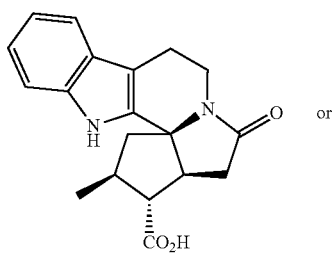

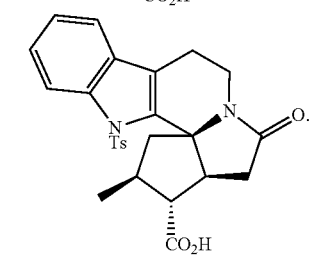

* * * * *

UNITED STATES PATENT AND TRADEMARK OFFICE
CERTIFICATE OF CORRECTION

PATENT NO. : 8,927,564 B2  
APPLICATION NO. : 13/789289  
DATED : January 6, 2015  
INVENTOR(S) : Dane Goff et al.

Page 1 of 1

It is certified that error appears in the above-identified patent and that said Letters Patent is hereby corrected as shown below:

In the Claims:

Column 104, compound shown at line 17, " 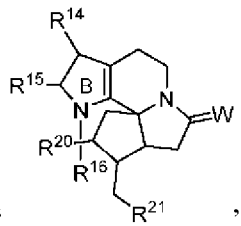 " should read

-- 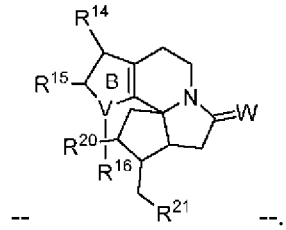 --.

Signed and Sealed this  
Third Day of May, 2016

Michelle K. Lee  
*Director of the United States Patent and Trademark Office*